United States Patent
Sakamoto et al.

(10) Patent No.: US 11,203,716 B2
(45) Date of Patent: *Dec. 21, 2021

(54) COMPOUND, POLYMERIZABLE COMPOUND, MIXTURE, POLYMERIZABLE LIQUID CRYSTAL COMPOSITION, POLYMER, OPTICAL FILM, OPTICALLY ANISOTROPIC PRODUCT, POLARIZING PLATE, FLAT PANEL DISPLAY DEVICE, ORGANIC ELECTROLUMINESCENCE DISPLAY DEVICE, AND ANTI-REFLECTION FILM

(71) Applicant: ZEON CORPORATION, Tokyo (JP)

(72) Inventors: Kei Sakamoto, Tokyo (JP); Kumi Okuyama, Tokyo (JP); Satoshi Kiriki, Tokyo (JP)

(73) Assignee: ZEON CORPORATION, Tokyo (JP)

(*) Notice: Subject to any disclaimer, the term of this patent is extended or adjusted under 35 U.S.C. 154(b) by 197 days.

This patent is subject to a terminal disclaimer.

(21) Appl. No.: 16/410,062

(22) Filed: May 13, 2019

(65) Prior Publication Data

US 2019/0264107 A1    Aug. 29, 2019

Related U.S. Application Data

(62) Division of application No. 15/598,379, filed on May 18, 2017, now abandoned.

(30) Foreign Application Priority Data

May 18, 2016 (JP) .................. 2016-100009

(51) Int. Cl.
C09K 19/38 (2006.01)
C07C 69/67 (2006.01)
(Continued)

(52) U.S. Cl.
CPC .......... *C09K 19/3861* (2013.01); *C07C 69/67* (2013.01); *C07C 69/75* (2013.01);
(Continued)

(58) Field of Classification Search
CPC ...................................................... C09K 19/38
See application file for complete search history.

(56) References Cited

U.S. PATENT DOCUMENTS 5,179,171 A   1/1993   Minami et al.
5,202,388 A   4/1993   Iio et al.
(Continued)

FOREIGN PATENT DOCUMENTS

CN   105524625 A   4/2016
EP   0854127 A1   7/1998
(Continued)

OTHER PUBLICATIONS

Jul. 29, 2019, Communication pursuant to Article 94(3) EPC issued by the European Patent Office in the corresponding European Patent Application No. 17171326.6.
(Continued)

*Primary Examiner* — Chanceity N Robinson
(74) *Attorney, Agent, or Firm* — Kenja IP Law PC

(57) ABSTRACT

Disclosed is a mixture containing polymerizable compounds having Formulas (III) and (IV) wherein $Ar^1$ and $Ar^2$ are divalent aromatic hydrocarbon or heteroaromatic ring group having D1 or D2 as a substituent; $D^1$ and $D^2$ are C1-C20 organic group having at least one aromatic ring selected from the group consisting of aromatic hydrocarbon ring and heteroaromatic ring; $A^{11}$-$A^{22}$ and $B^{11}$-$B^{22}$ are alicyclic or aromatic group which may have a substituent, $Y^{11}$-$Y^{22}$ and $L^{11}$-$L^{22}$ are single bond, —O—, —CO—, —CO—O—, —O—CO—, —$NR^{21}$—CO—, —CO—$NR^{22}$—,
(Continued)

—O—CO—O—, —NR²³—CO—O—, —O—CO—NR²⁴— or —NR²⁵—CO—NR²⁶— where $R^{21}$—$R^{26}$ are hydrogen or C1-C6 alkyl group; $R^4$—$R^9$ are hydrogen, methyl group or chlorine; one of f and k is integer of 1 to 3 with the other being integer of 0 to 3; g, j, m and q are integer of 1 to 20; and h, i, n and p are 0 or 1.

(III)

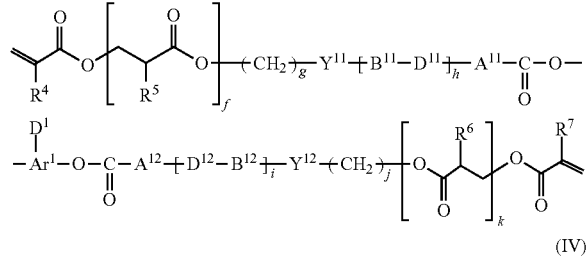

(IV)

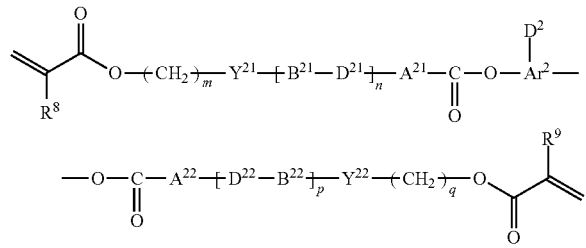

5 Claims, 2 Drawing Sheets

(51) Int. Cl.
  C07C 69/75      (2006.01)
  G02B 5/30       (2006.01)
  C07D 277/82     (2006.01)
  C08F 222/24     (2006.01)
  C08F 238/00     (2006.01)
  C09K 19/34      (2006.01)
  G02F 1/1335     (2006.01)
  H01L 51/00      (2006.01)
  H01L 51/52      (2006.01)
  G02F 1/13363    (2006.01)
  C09K 19/04      (2006.01)

(52) U.S. Cl.
  CPC .......... C07D 277/82 (2013.01); C08F 222/24 (2013.01); C08F 238/00 (2013.01); C09K 19/3497 (2013.01); G02B 5/30 (2013.01); G02B 5/3016 (2013.01); G02F 1/133528 (2013.01); H01L 51/004 (2013.01); H01L 51/0043 (2013.01); H01L 51/5281 (2013.01); C07C 2601/14 (2017.05); C09K 2019/0448 (2013.01); G02F 1/13363 (2013.01); G02F 1/133541 (2021.01); G02F 1/133638 (2021.01)

(56)         References Cited

U.S. PATENT DOCUMENTS

| 2014/0072730 A1 | 3/2014 | Hwang et al. |
| 2014/0142266 A1 | 5/2014 | Sakamoto et al. |
| 2015/0175564 A1* | 6/2015 | Sakamoto ............ C07D 513/04 526/257 |
| 2015/0277007 A1 | 10/2015 | Matsuyama et al. |
| 2016/0108315 A1* | 4/2016 | Matsuyama ....... C09K 19/3823 428/421 |

FOREIGN PATENT DOCUMENTS

| EP | 1026189 A1 | 8/2000 |
| EP | 2871192 A1 | 5/2015 |
| JP | H0597978 A | 4/1993 |
| JP | H05310845 A | 11/1993 |
| JP | H1180081 A | 3/1999 |
| JP | H11124429 A | 5/1999 |
| JP | 2003055661 A | 2/2003 |
| JP | 2003253265 A | 9/2003 |
| JP | 2004182949 A | 7/2004 |
| JP | 2007002208 A | 1/2007 |
| JP | 2009173893 A | 8/2009 |
| JP | 2009274984 A | 11/2009 |
| JP | 2010024438 A | 2/2010 |
| JP | 2010030979 A | 2/2010 |
| JP | 2010031223 A | 2/2010 |
| JP | 2011006360 A | 1/2011 |
| JP | 2015200877 A | 11/2015 |
| WO | 9920676 A1 | 4/1999 |
| WO | 2014010325 A1 | 1/2014 |

OTHER PUBLICATIONS

Jan. 2, 2019, Communication pursuant to Article 94(3) EPC issued by the European Patent Office in the corresponding European Patent Application No. 17171326.6.
Jun. 28, 2016, Notification of Reasons for Refusal issued by the Japan Patent Office in the corresponding Japanese Patent Application No. 2016-100009.
Michael B. Smith, et al., "March's Advanced Organic Chemistry : Reactions, Mechanisms, and Structure", Jan. 16, 2007, Sixth Edition, pp. 528-533, pp. 1040-1043, pp. 1276-1279, pp. 1284-1285, pp. 1410-1419, pp. 1528-1533, John Wiley & Sons, Inc.
Oct. 18, 2017, Extended European Search Report issued by the European Patent Office in the corresponding European Patent Application No. 17171326.6.
Oct. 4, 2016, Decision to Grant a Patent issued by the Japan Patent Office in the corresponding Japanese Patent Application No. 2016-100009.
Sandler, Stanley R. et al., "Organic functional group preparations", Mar. 25, 1976, pp. 34-69, pp. 82-181, pp. 208-317, pp. 334-405, Hirokawa Publishing Co.
Wen-Liang Tsai et al., "Fast Switching Ferroelectric Liquid Crystal Side Chain Polymer", Journal of Polymer Research, Apr. 1994, vol. 1, No. 2, pp. 191-196, Polymer Society.

* cited by examiner

COMPOUND, POLYMERIZABLE COMPOUND, MIXTURE, POLYMERIZABLE LIQUID CRYSTAL COMPOSITION, POLYMER, OPTICAL FILM, OPTICALLY ANISOTROPIC PRODUCT, POLARIZING PLATE, FLAT PANEL DISPLAY DEVICE, ORGANIC ELECTROLUMINESCENCE DISPLAY DEVICE, AND ANTI-REFLECTION FILM

CROSS-REFERENCE TO RELATED APPLICATION

This application is a divisional application of U.S. application Ser. No. 15/598,379 filed May 18, 2017, which claims priority based on Japanese Patent Application No. 2016-100009 filed May 18, 2016. The disclosures of the prior applications are hereby incorporated by reference herein in their entirety.

TECHNICAL FIELD

The present disclosure is directed to optical films and optically anisotropic products capable of uniform polarized light conversion over a wide wavelength range, and to polarizing plates, flat panel display devices, organic electroluminescence display devices and anti-reflection films which include the optically anisotropic product.

The present disclosure is also directed to polymers which may be used for the preparation of the optical films and optically anisotropic products, polymerizable compounds which may be used for the preparation of the polymers, mixtures and polymerizable liquid crystal compositions containing the polymerizable compounds, and compounds which may be used for the preparation of the polymerizable compounds and mixtures containing the compounds.

BACKGROUND

Phase difference plates used in flat panel display devices and other like devices include quarter-wave plates that convert linearly polarized light into circularly polarized light, and half-wave plates that rotate the plane of vibration of linearly polarized light by 90 degrees. These phase difference plates can achieve exact $\lambda/4$ or $\lambda/2$ phase difference for particular monochromatic light.

However, the conventional phase difference plates have the drawback of undesirably converting the polarized light emitting from the phase difference plate into colored one. The cause of this is that the material of the phase difference plate has wavelength dispersion of phase difference and white light, or composite waves which include different rays in the visible range, shows a distribution of polarization states at different wavelengths and hence incident light cannot be converted into polarized light having its phase retarded by exactly $\lambda/4$ or $\lambda/2$ over the entire wavelength range.

To address such a drawback, studies have been made for wide-band phase difference plates which may provide uniform phase difference over a wide wavelength range, i.e., phase difference plates having reversed wavelength dispersion.

Improvements in the function of portable information terminals such as mobile PCs and cellular phones and their widespread use are increasingly requiring that flat panel display devices be thinned as much as possible. Correspondingly, it is also required to make thinner the phase difference plates which constitute the flat panel display devices.

The method of making thinner phase difference plates which is deemed most effective in recent years involves applying polymerizable compositions containing low-molecular weight polymerizable compounds on film substrates to form optical films. This led to many developments of polymerizable compounds or polymerizable compositions containing the polymerizable compounds that allow for the manufacture of optical films that have superior reverse wavelength dispersion.

PTL 1 and PTL 2, for example, propose polymerizable compounds and polymerizable compositions that not only allow for the manufacture of optical films with superior reverse wavelength dispersion but can be easily applied on substrates for their low melting points suitable for processing, as well as show a wide temperature range of liquid crystallinity and can be synthesized at low costs.

CITATION LIST

Patent Literature

PTL 1: WO2014/010325A
PTL 2: JP2015200877A

SUMMARY

Manufacture of optical films or optically anisotropic products (hereinafter occasionally collectively referred to as "optical film, etc.") on an industrial scale using polymerizable compositions containing polymerizable compounds requires a wide process margin.

In particular, it is difficult to completely make uniform the temperature in the drying furnace and time conditions when polymerizable compositions are applied over large areas for the manufacture of optical film etc. Thus, a margin for the manufacturing conditions such as temperature and time greatly affects the yield of optical film etc.

The conventional polymerizable compounds and polymerizable compositions, however, are not sufficient in terms of process margin as optical film etc. cannot be obtained which can retain liquid crystal phase more stably over long periods of time. Accordingly, there has been a need in the art to provide polymerizable liquid crystal compositions containing polymerizable compounds which allow for the formation of optical film etc. which can retain liquid crystal phase more stably over long periods of time.

The present disclosure was made in light of the foregoing drawbacks pertinent in the art. It would therefore be helpful to provide polymerizable liquid crystal compositions which have low melting points suitable for practical use, can be produced at low costs, and allow for the formation of optical film etc. which are capable of uniform polarized light conversion over a wide wavelength range and of retaining crystal phase more stably over long periods of time.

It would also be helpful to provide polymerizable compounds useful for the preparation of the polymerizable liquid crystal compositions and mixtures containing the polymerizable compounds, and compounds useful for the preparation of the polymerizable compounds and mixtures containing the compounds.

The inventors made extensive studies to address the foregoing drawback and completed the present disclosure by establishing that the use of a mixture of specific polymerizable compounds having Formulas (III) and (IV) given below results in polymerizable liquid crystal compositions at low costs which allow for the formation of optical film etc. which can retain liquid crystal phase more stably over long periods of time, have less coating unevenness, and have superior reverse wavelength dispersion.

The present disclosure thus provides the compounds, polymerizable compounds, mixtures, polymerizable liquid crystal compositions, polymers, optical film, optically anisotropic product, polarizing plate, flat panel display device, organic electroluminescence display device, and anti-reflection film given below.

[1] A compound having the following Formula (I):

$$\text{(I)}$$

where $A^1$ and $B^1$ represent each independently alicyclic group which may have a substituent, or aromatic group which may have a substituent, $Y^1$ and $L^1$ represent each independently single bond, —O—, —CO—, —CO—O—, —O—CO—, —NR$^{21}$—CO—, —CO—NR$^{22}$—, —O—CO—O—, —NR$^{23}$—CO—O—, —O—CO—NR$^{24}$— or —NR$^{25}$—CO—NR$^{26}$—, where $R^{21}$ to $R^{26}$ represent each independently hydrogen or C1-C6 alkyl group, $R^1$ and $R^2$ represent each independently hydrogen, methyl group or chlorine, $FG^1$ represents hydroxyl group, carboxyl group or amino group, a represents an integer of 1 to 3, b represents an integer of 1 to 20, and c is 0 or 1.

[2] The compound of [1], wherein $FG^1$ is hydroxyl group, and c is 0.

[3] The compound of [1], wherein $FG^1$ is carboxyl group, and c is 1.

[4] A mixture including:

the compound of any one of [1] to [3]; and a compound having the following Formula (II):

$$\text{(II)}$$

where $A^2$ and $B^2$ represent each independently alicyclic group which may have a substituent, or aromatic group which may have a substituent, $Y^2$ and $L^2$ represent each independently single bond, —O—, —CO—, —CO—O—, —O—CO—, —NR$^{21}$—CO—, —CO—NR$^{22}$—, —O—CO—O—, —NR$^{23}$—CO—O—, —O—CO—NR$^{24}$— or —NR$^{25}$—CO—NR$^{26}$—, where $R^{21}$ to $R^{26}$ represent each independently hydrogen or C1-C6 alkyl group, $R^3$ represents hydrogen, methyl group or chlorine, $FG^2$ represents hydroxyl group, carboxyl group or amino group, d represents an integer of 1 to 20, and e is 0 or 1.

[5] The mixture of [4], wherein $FG^1$ and $FG^2$ are hydroxyl groups, and c and e are 0.

[6] The mixture of [4], wherein $FG^1$ and $FG^2$ are carboxyl groups, and c and e are 1.

[7] The mixture of any one of [4] to [6], wherein a mass ratio of the compound having Formula (I) to the compound having Formula (II) (compound having Formula (I):compound having Formula (II)) is 1:1,000 to 20:100.

[8] A polymerizable compound having the following Formula (III):

$$\text{(III)}$$

where $Ar^1$ represents divalent aromatic hydrocarbon ring group having $D^1$ as a substituent, or divalent heteroaromatic ring group having $D^1$ as a substituent, $D^1$ represents C1-C20 organic group having at least one aromatic ring selected from the group consisting of an aromatic hydrocarbon ring and a heteroaromatic ring, $Z^1$ and $Z^{12}$ represent each independently —CO—O—, —O—CO—, —NR$^{31}$—CO— or —CO—NR$^{32}$—, where $R^{31}$ and $R^{32}$ represent each independently hydrogen or C1-C6 alkyl group, $A^{11}$, $A^{12}$, $B^{11}$ and $B^{12}$ represent each independently alicyclic group which may have a substituent, or aromatic group which may have a substituent, $Y^{11}$, $Y^{12}$, $L^{11}$ and $L^{12}$ represent each independently single bond, —O—, —CO—, —CO—O—, —O—CO—, —NR$^{21}$—CO—, —CO—NR$^{22}$—, —O—CO—O—, —NR$^{23}$—CO—O—, —O—CO—NR$^{24}$— or —NR$^{25}$—CO—NR$^{26}$—, where $R^{21}$ to $R^{26}$ represent each independently hydrogen or C1-C6 alkyl group, $R^4$ to $R^7$ represent each independently hydrogen, methyl group or chlorine, one of f and k is an integer of 1 to 3 with the other being an integer of 0 to 3, g and j represent each independently an integer of 1 to 20, and h and i are each independently 0 or 1.

[9] The polymerizable compound of [8], wherein $Ar^1$-$D^1$ is a divalent group having the following Formula (V):

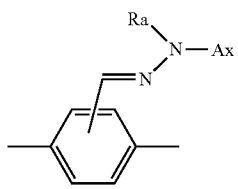

(V)

where Ax represents C2-C20 organic group having at least one aromatic ring selected from the group consisting of an aromatic hydrocarbon ring and a heteroaromatic ring, and Ra represents hydrogen or C1-C20 organic group which may have a substituent.

[10] The polymerizable compound of [9], wherein Ax is a group having the following Formula (VI):

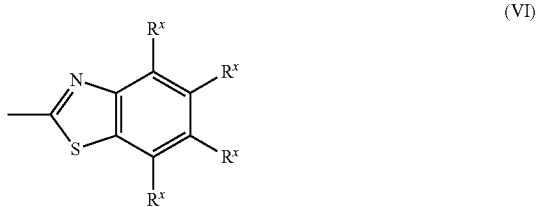

(VI)

where $R^x$ represents hydrogen, halogen, C1-C6 alkyl group, cyano group, nitro group, C1-C6 fluoroalkyl group, C1-C6 alkoxy group, or —C(=O)—O—$R^b$, where $R^b$ represents C1-C20 alkyl group which may have a substituent, C2-C20 alkenyl group which may have a substituent, C3-C12 cycloalkyl group which may have a substituent, or C5-C12 aromatic hydrocarbon ring group which may have a substituent, each $R^x$ may be the same or different, and at least one C—$R^x$ constituting the ring may be replaced by nitrogen.

[11] The polymerizable compound of [9] or [10], wherein Ra is C1-C20 alkyl group which may have a substituent, C2-C20 alkenyl group which may have a substituent, C2-20 alkynyl group which may have a substituent, or C6-C18 aromatic group which may have a substituent.

[12] A mixture including:

the polymerizable compound of any one of [8] to [11]; and a polymerizable compound having the following Formula (IV):

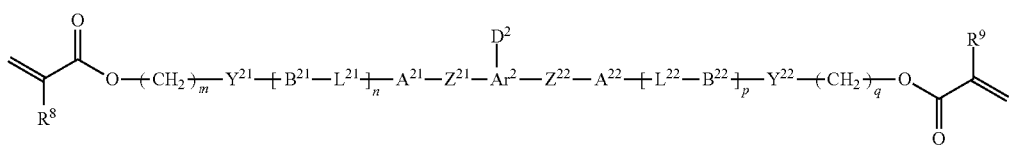

(IV)

where $Ar^2$ represents divalent aromatic hydrocarbon ring group having $D^2$ as a substituent, or divalent heteroaromatic ring group having $D^2$ as a substituent, $D^2$ represents C1-C20 organic group having at least one aromatic ring selected from the group consisting of an aromatic hydrocarbon ring and a heteroaromatic ring, $Z^{21}$ and $Z^{22}$ represent each independently —CO—O—, —O—CO—, —NR$^{31}$—CO—, or —CO—NR$^{32}$—, where $R^{31}$ and $R^{32}$ represent each independently hydrogen or C1-C6 alkyl group, $A^{21}$, $A^{22}$, $B^{21}$ and $B^{22}$ represent each independently alicyclic group which may have a substituent, or aromatic group which may have a substituent, $Y^{21}$, $Y^{22}$, $L^{21}$ and $L^{22}$ represent each independently single bond, —O—, —CO—, —CO—O—, —O—CO—, —NR$^{21}$—CO—, —CO—NR$^{22}$—, —O—CO—O—, —NR$^{23}$—CO—O—, —O—CO—NR$^{24}$— or —NR$^{25}$—CO—NR$^{26}$—, where $R^{21}$ to $R^{26}$ represent each independently hydrogen or C1-C6 alkyl group, $R^8$ and $R^9$ represent each independently hydrogen, methyl group or chlorine, m and q represent each independently an integer of 1 to 20, and n and p are each independently 0 or 1.

[13] The mixture of [12], wherein $Ar^1$-$D^1$ is a divalent group having the following Formula (V):

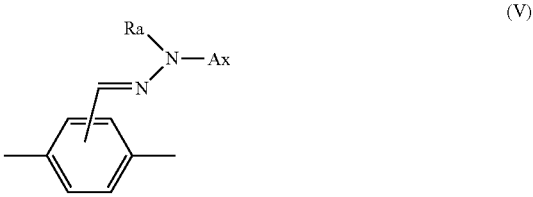

(V)

where Ax represents C2-C20 organic group having at least one aromatic ring selected from the group consisting of an aromatic hydrocarbon ring and a heteroaromatic ring, and Ra represents hydrogen or C1-C20 organic group which may have a substituent, and wherein $Ar^2$-$D^2$ is a divalent group having the following Formula (VII):

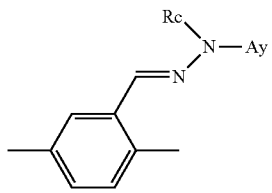
(VII)

where Ay represents C2-C20 organic group having at least one aromatic ring selected from the group consisting of an aromatic hydrocarbon ring and a heteroaromatic ring, and Rc represents hydrogen or C1-C20 organic group which may have a substituent.

[14] The mixture of [13], wherein Ax and Ay are each independently a group having the following Formula (VI):

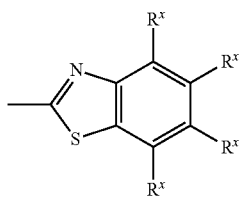
(VI)

where $R^x$ represents hydrogen, halogen, C1-C6 alkyl group, cyano group, nitro group, C1-C6 fluoroalkyl group, C1-C6 alkoxy group, or —C(=O)—O—$R^b$, where $R^b$ represents C1-C20 alkyl group which may have a substituent, C2-C20 alkenyl group which may have a substituent, C3-C12 cycloalkyl group which may have a substituent, or C5-C12 aromatic hydrocarbon ring group which may have a substituent, each $R^x$ may be the same or different, and at least one C—$R^x$ constituting the ring may be replaced by nitrogen.

[15] The mixture of [13] or [14], wherein Ra is C1-C20 alkyl group which may have a substituent, C2-C20 alkenyl group which may have a substituent, C2-20 alkynyl group which may have a substituent, or C6-C18 aromatic group which may have a substituent, and Rc is C1-C20 alkyl group which may have a substituent, C2-C20 alkenyl group which may have a substituent, C2-20 alkynyl group which may have a substituent, or C6-C18 aromatic group which may have a substituent.

[16] The mixture of any one of [12] to [15], wherein a mass ratio of the polymerizable compound having Formula (III) to the polymerizable compound having Formula (IV) (polymerizable compound having Formula (III):polymerizable compound having Formula (IV)) is 1:1,000 to 20:100.

[17] A polymerizable liquid crystal composition including:
the mixture of any one of [12] to [16]; and
a polymerization initiator.

[18] A polymer obtainable by polymerization of the mixture of any one of [12] to [16].

[19] A polymer obtainable by polymerization of the polymerizable liquid crystal composition of [17].

[20] An optical film including the polymer of [18] or [19] as a constituent material.

[21] An optically anisotropic product including a layer which comprises the polymer of [18] or [19] as a constituent material.

[22] A polarizing plate including:
the optically anisotropic product of [21]; and
a polarizing film.

[23] A flat panel display device including:
the polarizing plate of [22]; and
a liquid crystal panel.

[24] An organic electroluminescence display device including:
the polarizing plate of [22]; and
an organic electroluminescence panel.

[25] An anti-reflection film including the polarizing plate of [22].

The present disclosure provides polymerizable liquid crystal compositions which can retain liquid crystal phase more stably over long periods of time, have low melting points suitable for practical use, and allow for low-cost manufacture of optical film etc. which are capable of uniform polarized light conversion over a wide wavelength range with a wide process margin.

The present disclosure also provides polymerizable compounds useful for the preparation of the polymerizable liquid crystal compositions and mixtures containing the polymerizable compounds, and compounds useful for the preparation of the polymerizable compounds and mixtures containing the compounds.

The present disclosure further provides optical films and optically anisotropic products capable of uniform polarized light conversion over a wide wavelength range, and polarizing plates, flat panel display devices, organic electroluminescence (EL) display devices and anti-reflection films including the optical film or optically anisotropic product.

BRIEF DESCRIPTION OF THE DRAWINGS

In the accompanying drawings:

FIG. 1A is a cross sectional schematic of the laminate, and FIG. 1B is an explanatory schematic of the relationship between absorption axis and slow axis; FIG. 2A is a picture of a laminate having an optically anisotropic product without coating unevenness (evaluation index: 5), and FIG. 2B is a picture of a laminate having an optically anisotropic product with coating unevenness (evaluation index: 1).

DETAILED DESCRIPTION

Figure 1A:
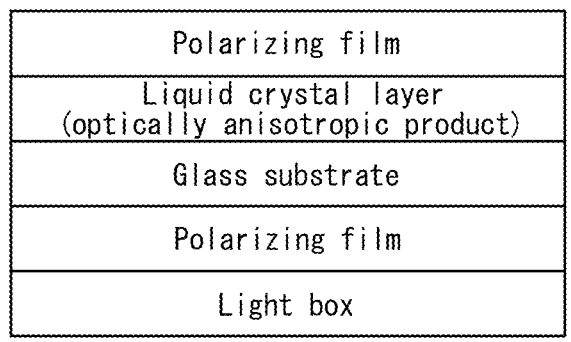
FIGS. 1A and 1B illustrate a configuration of a laminate used for a stability evaluation test of a liquid crystal phase, where

The present disclosure will now be described in detail. By the phrase "may have a substituent" as used herein is meant "substituted or unsubstituted." Further, it is defined herein that when organic groups such as alkyl group and aromatic hydrocarbon ring group in the general formula have a substituent, the number of carbon atoms of the organic groups having a substituent excludes the number of carbon atoms of the substituent. For example, when a C6-C20 aromatic hydrocarbon ring group has a substituent, the number of carbon atoms of the C6-C20 aromatic hydrocarbon ring group excludes the number of carbon atoms of such a substituent.

The disclosed compound and mixture containing the compound can be used in any application, e.g., for the preparation of the disclosed polymerizable compound.

The disclosed polymerizable compound and mixture containing the polymerizable compound can be used in any application, e.g., for the preparation of the disclosed polymerizable liquid crystal composition.

The disclosed polymerizable liquid crystal composition can be used in any application, e.g., for the preparation of the disclosed polymer.

The disclosed polymer can be used in any application, e.g., as the constituent material of the disclosed optical film and as the constituent material of a layer of the disclosed optically anisotropic product. The disclosed optically anisotropic product can be used in any application, e.g., for the disclosed polarizing plate. The disclosed polarizing plate can be used in any application, e.g., for the disclosed flat panel display device, organic electroluminescence display device and anti-reflection film.

(1) Compound

The disclosed compound has Formula (I) given below (hereinafter occasionally referred to as "compound (I)") and is useful as an intermediate for the production of polymerizable compound (III) later described.

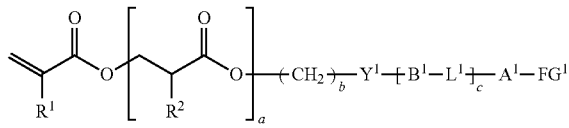

(I)

In Formula (I), a is an integer of 1 to 3, b is an integer of 1 to 20, preferably an integer of 2 to 12, more preferably an integer of 4 to 8, and c is 0 or 1.

$FG^1$ is hydroxyl group, carboxyl group or amino group. When c is 0, $FG^1$ is preferably hydroxyl group, and when c is 1, $FG^1$ is preferably carboxyl group.

$A^1$ is alicyclic group which may have a substituent or aromatic group which may have a substituent. In particular, when c is 0, $A^1$ is preferably aromatic group which may have a substituent, and when c is 1, $A^1$ is preferably alicyclic group which may have a substituent.

The alicyclic group which may have a substituent is a substituted or unsubstituted divalent alicyclic group, where the divalent alicyclic group is a divalent aliphatic group having cyclic structure and typically having 5 to 20 carbon atoms.

Specific examples of the divalent alicyclic group include C5-C20 cycloalkanediyl group such as cyclopentane-1,3-diyl, cyclohexane-1,4-diyl, 1,4-cycloheptane-1,4-diyl, and cyclooctane-1,5-diyl; and C5-C20 bicycloalkanediyl group such as decahydronaphthalene-1,5-diyl and decahydronaphthalene-2,6-diyl.

The aromatic group which may have a substituent is a substituted or unsubstituted divalent aromatic group, where the divalent aromatic group is a divalent aromatic group having aromatic ring structure and typically having 2 to 20 carbon atoms.

Specific examples of the divalent aromatic group include C6-C20 divalent aromatic hydrocarbon ring group such as 1,4-phenylene group, 1,4-naphthylene group, 1,5-naphthylene group, 2,6-naphthylene group, and 4,4'-biphenylene group; and C2-C20 divalent heteroaromatic ring group such as furan-2,5-diyl, thiophene-2,5-diyl, pyridine-2,5-diyl, and pyrazine-2,5-diyl.

Examples of the substituents on the divalent alicyclic group and divalent aromatic group described above include halogens such as fluorine, chlorine and bromine; C1-C6 alkyl group such as methyl group and ethyl group; C1-C5 alkoxy group such as methoxy group and isopropoxy group; nitro group; and cyano group. The alicyclic group and aromatic group may have at least one substituent selected from the substituents described above. When more than one substituent occurs, each substituent may be the same or different.

When c is 1, $L^1$ is single bond, —O—, —CO—, —CO—O—, —O—CO—, —$NR^{21}$—CO—, —CO—$NR^{22}$—, —O—CO—O—, —$NR^{23}$—CO—O—, —O—CO—$NR^{24}$— or —$NR^{25}$—CO—$NR^{26}$—, where $R^{21}$ to $R^{26}$ represent each independently hydrogen or C1-C6 alkyl group. In particular, $L^1$ is preferably —O—, —CO—O— or —O—CO—.

Examples of the C1-C6 alkyl group for $R^{21}$ to $R^{26}$ include methyl group, ethyl group, propyl group, and isopropyl group.

When c is 1, $B^1$ is alicyclic group which may have a substituent or aromatic group which may have a substituent. In particular, $B^1$ is preferably aromatic group which may have a substituent.

The alicyclic group which may have a substituent is a substituted or unsubstituted divalent alicyclic group, where the divalent alicyclic group is a divalent aliphatic group having cyclic structure and typically having 5 to 20 carbon atoms.

Specific examples of the divalent alicyclic group for $B^1$ are the same as those exemplified for $A^1$.

The aromatic group which may have a substituent is a substituted or unsubstituted divalent aromatic group, where the divalent aromatic group is a divalent aromatic group having aromatic ring structure and typically having 2 to 20 carbon atoms.

Specific examples of the divalent aromatic group for $B^1$ are the same as those exemplified for $A^1$.

Examples of the substituents on the divalent alicyclic group and divalent aromatic group for $B^1$ are the same as those exemplified for the divalent alicyclic group and divalent aromatic group for $A^1$.

$Y^1$ is single bond, —O—, —CO—, —CO—O—, —O—CO—, —$NR^{21}$—CO—, —CO—$NR^{22}$—, —O—CO—O—, —$NR^{23}$—CO—O—, —O—CO—$NR^{24}$— or —$NR^{25}$—CO—$NR^{26}$—, where $R^{21}$ to $R^{26}$ represent each independently hydrogen or C1-C6 alkyl group. In particular, $Y^1$ is preferably —O—, —CO—O— or —O—CO—.

Examples of the C1-C6 alkyl group for $R^{21}$ to $R^{26}$ include methyl group, ethyl group, propyl group, and isopropyl group.

$R^2$ is hydrogen, methyl group or chlorine, preferably hydrogen or methyl group.

$R^1$ is hydrogen, methyl group or chlorine, preferably hydrogen or methyl group. More preferably, $R^1$ and $R^2$ are the same, and even more preferably, $R^1$ and $R^2$ are hydrogen.

Compound (I) described above can be synthesized by combining synthesis reactions known in the art. Specifically, compound (I) can be synthesized with reference to methods described in various literatures, e.g., March's Advanced Organic Chemistry (Wiley), and S. R. Sandler and W. Karo "Organic Functional Group Preparations."

A preferred example of compound (I) where c is 0 includes, but not limited to, a compound having the following Formula (Ia) (hereinafter occasionally referred to as "compound (Ia)":

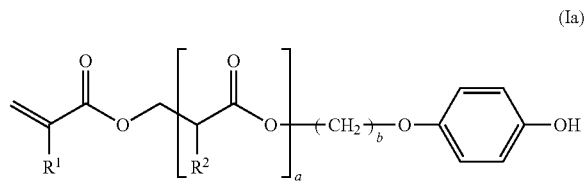

where $R^1$, $R^2$, a and b are as defined above in Formula (I).

Compound (Ia) can be produced by any method, e.g., by the method described below.

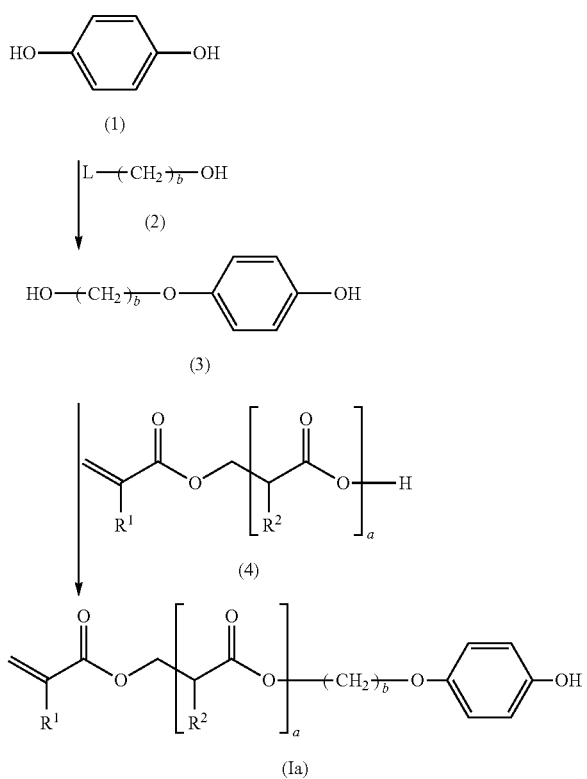

where $R^1$, $R^2$, a and b are as defined above in Formula (I), and L represents leaving group.

More specifically, first, hydroquinone having Formula (1) and a compound having Formula (2) (hereinafter referred to as "compound (2)") are reacted to give a monoether compound having Formula (3) (hereinafter referred to as "monoether compound (3)").

In Formula (2), the leaving group represented by L is any leaving group commonly used in organic chemistry. Examples of L include halogens such as chlorine, bromine, and iodine.

As regards the amounts of hydroquinone and compound (2) used, typically 1.0 to 5.0 moles, preferably 1.2 to 1.5 moles of hydroquinone is used per 1 mole of compound (2).

The use of too little hydroquinone results in increased production of the by-product diether compound and therefore the yield and purity of monoether compound (3) tend to decrease. On the other hand, the use of too much hydroquinone tends to make it difficult to perform efficient purification treatment after completion of the reaction.

The reaction between hydroquinone and compound (2) may be carried out in inert solvent in the presence of a base, or in a two-phase solvent system of alkaline aqueous solution/hydrophobic organic solvent. The latter method is preferred because the target product can be obtained in higher yield.

Examples of inert solvents used in this reaction include amide solvents such as N-methylpyrrolidone, and N,N-dimethylformamide; ether solvents such as tetrahydrofuran, 1,3-dimethoxyethane, and anisole; sulfur-containing solvents such as dimethyl sulfoxide; aliphatic hydrocarbon solvents such as n-pentane, n-hexane, n-heptane, and cyclohexane; aromatic hydrocarbon solvents such as benzene, toluene, and xylene; and mixture solvents of two or more of the foregoing.

Any amount of solvent can be used and the amount can be determined as appropriate in light of, for example, the types of compounds used or reaction scale. Typically, 1 to 50 parts by mass of solvent are used per 1 part by mass of compound (2).

Examples of bases used include organic bases such as pyridine, trimethylamine, triethylamine, aniline, picoline, 1,8-diazabicyclo[5.4.0]-7-undecene, 1,4-diazabicyclo[2.2.2]octane, imidazole, and N,N-diisopropylethylamine; metal alcoholates such as sodium methoxide, sodium ethoxide, and potassium t-butoxide; metal hydrides such as sodium hydride and calcium hydride; metal hydroxides such as sodium hydroxide, potassium hydroxide, and calcium hydroxide; and metal carbonates such as sodium carbonate, potassium carbonate, and magnesium carbonate.

Typically, 1 to 5 equivalents, preferably 1 to 2 equivalents of base are used with respect to compound (2).

The alkaline aqueous solution used in the latter method can be obtained by dissolving an inorganic base in water.

Examples of the inorganic base include alkali metal carbonates such as sodium carbonate and potassium carbonate; alkali earth metal carbonates such as magnesium carbonate and calcium carbonate; alkali metal hydrogen carbonates such as sodium hydrogen carbonate and potassium hydrogen carbonate; alkali earth metal hydrogen carbonates such as magnesium hydrogen carbonate and calcium hydrogen carbonate; alkali metal hydroxides such as sodium hydroxide and potassium hydroxide; and alkali earth metal hydroxides such as magnesium hydroxide and calcium hydroxide.

The inorganic bases can be used alone or in combination.

The amount of inorganic base in the alkaline aqueous solution is typically 1.00 to 2.00 moles, preferably 1.05 to 1.50 moles, per 1 mole of compound (2). When the inorganic base content is too small, there are concerns of reduced yield of the monoether compound, low reaction rate, or high abundance of residual compound (2). On the other hand, when too much inorganic base is used, an additional neutralization step is required after the reaction.

Any amount of alkaline aqueous solution can be used so long as hydroquinone and compound (2) are dissolved therein.

The alkaline aqueous solution is used at an amount of typically 1 to 10 parts by mass, preferably 3 to 6 parts by mass, per 1 part by mass of compound (2). When too much alkaline aqueous solution is used, there are concerns of low reaction rate or low productivity. On the other hand, when too little alkaline aqueous solution is used, there are concerns of precipitation of source compounds, or reduced reaction rate due to increased level of solution viscosity.

Hydrophobic organic solvents refer to organic solvents having a solubility of 10 g or less in 100 g of water at 25° C.

Examples of the hydrophobic organic solvent include aromatic hydrocarbon solvents such as benzene, toluene, xylene, and mesitylene; aliphatic hydrocarbon solvents such as n-pentane, n-hexane, n-heptane, and cyclohexane; ether solvents such as anisole, cyclopentyl methyl ether (CPME), diethyl ether, and diisopropyl ether; C4 or higher alcohol solvents such as 1-butanol and 1-hexanol; and halogenated hydrocarbon solvents such as dichloromethane, dichloroethane, and chlorobenzene.

Of these hydrophobic organic solvents, preferred are aromatic hydrocarbon solvents, ether solvents or C4 or higher alcohol solvents for example because of their high azeotropic points with water that enable reactions at high temperatures and selective production of the target monoether compound (3) is facilitated, with toluene, xylene, anisole, cyclopentyl methyl ether, or 1-hexanol being more preferred.

The hydrophobic organic solvents can be used alone or in combination.

The hydrophobic organic solvent is used at an amount of typically 0.2 to 10 parts by mass, preferably 0.5 to 2 parts by mass, per 1 part by mass of compound (2). When too much hydrophobic organic solvent is used, there are concerns of low reaction rate or low productivity. On the other hand, when too little hydrophobic organic solvent is used, there are concerns that the monoether compound can be selectively synthesized only with difficulty because the effect of using the hydrophobic organic solvent is not easily obtained.

The reaction between hydroquinone and compound (2) is carried out in inert gas atmosphere such as in nitrogen or argon gas.

The reaction can be carried out at any temperature, and reaction temperature is typically 20° C. to 200° C., preferably 60° C. to 150° C., more preferably 80° C. to 120° C.

Reaction time is typically 1 to 24 hours, although it depends on the reaction temperature and other conditions.

After completion of the reaction, the reaction solution can be cooled to precipitate crystals of target monoether compound (3).

The purity of monoether compound (3) (ratio of the monoether compound to the total of the monoether compound and diether compound) is typically 70 mass % or higher, preferably 80 mass % or higher.

The resulting crystals of monoether compound (3) can be directly used in the subsequent step without purification or, where necessary, can be purified by column chromatography, re-crystallization, re-precipitation or other methods known in the art to give a more pure monoether compound for use in the subsequent step.

The structure of monoether compound (3) can be determined by NMR spectroscopy, IR spectroscopy, mass spectroscopy, or elemental analysis.

Next, the resulting monoether compound (3) and a carboxylic compound having Formula (4) (hereinafter referred to as "compound (4)") are subjected to a dehydration condensation reaction to give target compound (Ia).

The dehydration condensation reaction is carried out in proper solvent in the presence of an acid catalyst.

Examples of acid catalysts used include, but not limited to, mineral acids such as hydrochloric acid, sulfuric acid, phosphoric acid, and nitric acid; heteropoly acids such as phosphotungstic acid; and organic acids such as p-toluenesulfonic acid.

The acid catalyst is used at an amount of typically 0.01 to 20 mass %, preferably 0.05 to 10 mass %, more preferably 0.1 to 5 mass %, with respect to monoether compound (3). Alternatively, the acid catalyst is used at an amount of typically 0.01 to 1.0 mole, preferably 0.01 to 0.5 moles, per 1 mole of monoether compound (3).

Examples of solvents used include ether solvents such as tetrahydrofuran, 1,3-dimethoxyethane, and anisole; aliphatic hydrocarbon solvents such as n-pentane, n-hexane, n-heptane, and cyclohexane; aromatic hydrocarbon solvents such as benzene, toluene, and xylene; and mixture solvents of two or more of the foregoing.

Of these solvents, preferred are aromatic hydrocarbon solvents, with toluene being more preferred.

For a better yield of the target compound, the dehydration condensation reaction is preferably carried out while removing the generated water out of the system. One exemplary method for that purpose is to use a Dean-Stark trap or other like device to remove the generated water out of the system during reaction.

Further, the dehydration condensation reaction may be carried out in the presence of an antioxidant to stabilize the ether compound. Examples of antioxidants used include 2,6-di-(t-butyl)-4-methylphenol (BHT), 2,2'-methylenebis (6-t-butyl-p-cresol), and triphenyl phosphite.

When an antioxidant is used, it is used at an amount of typically 0.1 to 10 parts by mass, preferably 0.5 to 5 parts by mass, per 100 parts by mass of the ether compound.

The dehydration condensation reaction can be carried out at any temperature, and reaction temperature is typically 20° C. to 200° C., preferably 40° C. to 150° C., more preferably 60° C. to 150° C.

Reaction time is typically 1 to 24 hours, although it depends on the reaction temperature and other conditions.

After completion of the reaction, post-treatment operations commonly used in synthetic organic chemistry are performed, and where desired, the reaction product can be purified by isolation/purification methods known in the art, such as distillation, column chromatography, re-crystallization or re-precipitation, for efficient isolation of the target compound (Ia).

The structure of the target compound can be identified by NMR spectroscopy, IR spectroscopy, mass spectroscopy or other analysis methods.

Compound (4) can be obtained by dimerization, trimerization and tetrameriztion of acrylic acid. In this case, compound (4) is typically obtained as a mixture containing, in addition to 2-carboxyethyl acrylate (dimer), acrylic acid itself and a trimer or higher oligomer of acrylic acid.

Compound (4) can be used as a separate compound isolated by purifying the mixture obtained in this way.

Further, as will be described later, when the resulting mixture contains acrylic acid and compound (4), this mixture (hereinafter occasionally referred to as "mixture (D)") can be used instead of compound (4). Mixture (D) preferably contains 0.01 to 20 mass % of compound (4).

A commercially available compound can also be directly used as compound (4).

A preferred example of compound (I) where c is 1 includes, but not limited to, a compound having the following Formula (IIIa) (hereinafter occasionally referred to as "compound (IIIa)":

(IIIa)

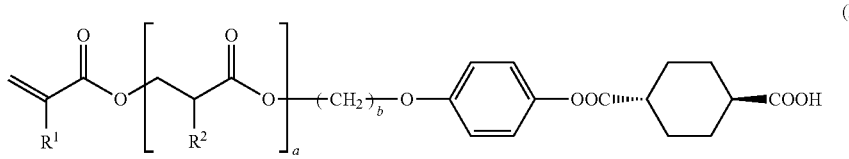

where $R^1$, $R^2$, a and b are as defined above in Formula (I).

Compound (IIIa) can be produced by any method, e.g., by the method described below where compound (Ia) is reacted with trans-1,4-cyclohexanedicarboxylic acid having the following Formula (5):

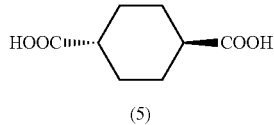

(5)

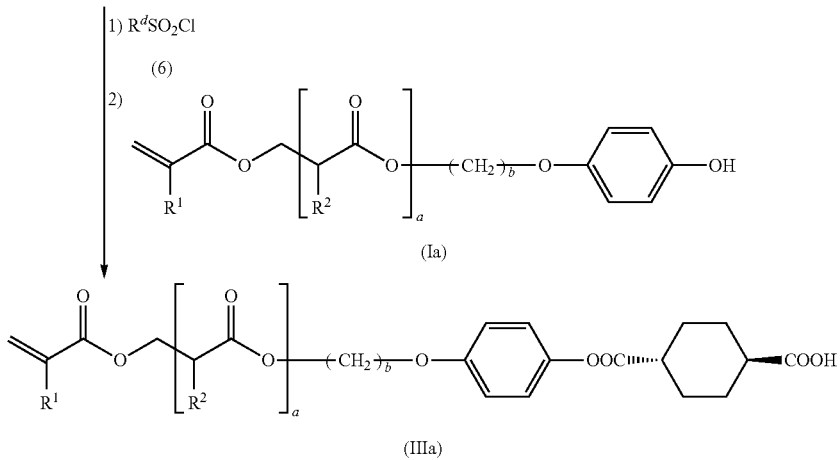

where $R^1$, $R^2$, a and b are as defined above in Formula (I), and $R^d$ represents C1-C6 alkyl group such as methyl group and ethyl group, or C6-C20 aromatic hydrocarbon ring group which may have a substituent, such as phenyl group, 4-methyl phenyl group and 4-methoxy phenyl group.

More specifically, first, compound (5) is reacted with a sulfonyl chloride having Formula (6) in proper solvent in the presence of a first base.

To the resulting reaction mixture are added compound (Ia) and a second base for further reaction.

The sulfonyl chloride compound is used at an amount of typically 0.5 to 2.1 equivalents, preferably 0.5 to 1.1 equivalents, per 1 equivalent of compound (5).

Compound (Ia) is used at an amount of typically 0.5 to 1.0 equivalent per 1 equivalent of compound (5).

The first and second bases are used at amounts of typically 0.5 to 2.1 equivalents, preferably 0.5 to 1.1 equivalents, per 1 equivalent of compound (5).

Examples of the first and second bases include triethylamine, N,N-diisopropylethylamine, and 4-(dimethylamino)pyridine.

Reaction temperature can range from −10° C. to 30° C., and reaction time can be several minutes to several hours, although it depends on the reaction scale and other conditions.

Examples of solvents used in the reaction described above include the same solvents as those exemplified for the production of compound (Ia), and halogenated solvents such as methylene chloride and chloroform. Of these solvents, preferred are ether solvents.

Any amount of solvent can be used and the amount can be determined as appropriate in light of, for example, the types of compounds used or reaction scale. Typically, 1 to 50 parts by mass of solvent are used per 1 part by mass of compound (Ia).

After completion of the reaction, post-treatment operations commonly used in synthetic organic chemistry are performed, and where desired, the reaction product can be purified by isolation/purification methods known in the art, such as column chromatography, re-crystallization, distillation or re-precipitation, for isolation of the target compound.

The structure of the target compound can be identified by NMR spectroscopy, IR spectroscopy, mass spectroscopy, elemental analysis or other analysis methods.

(2) Mixture Containing Compounds

The disclosed mixture is a mixture containing compound (I) and a compound having the following Formula (II) (hereinafter referred to as "compound (II)") and can be used for example for the production of polymerizable compound (III) described later.

From the perspective of enhancing reverse wavelength dispersion of the resulting optical film etc. while broadening the process margin upon formation of the optical film etc. using a mixture or polymerizable liquid crystal composition containing polymerizable compound (III) prepared using the mixture, the mass ratio of compound (I) to compound (II) (compound (I):compound (II)) in the mixture is preferably 1:1,000 to 20:100, more preferably 1:100 to 20:100.

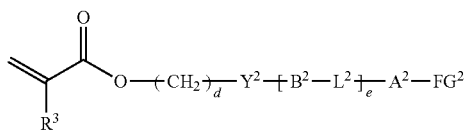

(II)

In Formula (II) d is an integer of 1 to 20, preferably an integer of 2 to 12, more preferably an integer of 4 to 8, and e is 0 or 1.

$FG^2$ is hydroxyl group, carboxyl group or amino group. When e is 0, $FG^2$ is preferably hydroxyl group, and when e is 1, $FG^2$ is preferably carboxyl group.

$A^2$ is alicyclic group which may have a substituent or aromatic group which may have a substituent. In particular, when e is 0, $A^2$ is preferably aromatic group which may have a substituent, and when e is 1, $A^2$ is preferably alicyclic group which may have a substituent.

The alicyclic group which may have a substituent is a substituted or unsubstituted divalent alicyclic group, where the divalent alicyclic group is a divalent aliphatic group having cyclic structure and typically having 5 to 20 carbon atoms.

Specific examples of the divalent alicyclic group for $A^2$ are the same as those exemplified for $A^1$.

The aromatic group which may have a substituent is a substituted or unsubstituted divalent aromatic group, where the divalent aromatic group is a divalent aromatic group having aromatic ring structure and typically having 2 to 20 carbon atoms.

Specific examples of the divalent aromatic group for $A^2$ are the same as those exemplified for $A^1$.

Examples of the substituents on the divalent alicyclic group and divalent aromatic group for $A^2$ are the same as those exemplified for the divalent alicyclic group and divalent aromatic group for $A^1$.

When e is 1, $L^2$ is single bond, —O—, —CO—, —CO—O—, —O—CO—, —$NR^{21}$—CO—, —CO—$NR^{22}$—, —O—CO—O—, —$NR^{23}$—CO—O—, —O—CO—$NR^{24}$— or —$NR^{25}$—CO—$NR^{26}$—, where $R^{21}$ to $R^{26}$ represent each independently hydrogen or C1-C6 alkyl group. In particular, $L^2$ is preferably —O—, —CO—O— or —O—CO—.

Examples of the C1-C6 alkyl group for $R^{21}$ to $R^{26}$ include methyl group, ethyl group, propyl group, and isopropyl group.

When c is 1, $B^2$ is alicyclic group which may have a substituent or aromatic group which may have a substituent. In particular, $B^2$ is preferably aromatic group which may have a substituent.

The alicyclic group which may have a substituent is a substituted or unsubstituted divalent alicyclic group, where the divalent alicyclic group is a divalent aliphatic group having cyclic structure and typically having 5 to 20 carbon atoms.

Specific examples of the divalent alicyclic group for $B^2$ are the same as those exemplified for $A^1$.

The aromatic group which may have a substituent is a substituted or unsubstituted divalent aromatic group, where the divalent aromatic group is a divalent aromatic group having aromatic ring structure and typically having 2 to 20 carbon atoms.

Specific examples of the divalent aromatic group for $B^2$ are the same as those exemplified for $A^1$.

Examples of the substituents on the divalent alicyclic group and divalent aromatic group for $B^2$ are the same as those exemplified for the divalent alicyclic group and divalent aromatic group for $A^1$.

$Y^2$ is single bond, —O—, —CO—, —CO—O—, —O—CO—, —$NR^{21}$—CO—, —CO—$NR^{22}$—, —O—CO—O—, —$NR^{23}$—CO—O—, —O—CO—$NR^{24}$— or —$NR^{25}$—CO—$NR^{26}$—, where $R^{21}$ to $R^{26}$ are each independently hydrogen or C1-C6 alkyl group. In particular, $Y^2$ is preferably —O—, —CO—O— or —O—CO—.

Examples of the C1-C6 alkyl group for $R^{21}$ to $R^{26}$ include methyl group, ethyl group, propyl group, and isopropyl group.

$R^3$ is hydrogen, methyl group or chlorine, preferably hydrogen or methyl group.

Compound (II) described above can be synthesized by combining synthesis methods known in the art. Specifically, compound (II) can be synthesized with reference to methods described in various literatures, e.g., March's Advanced Organic Chemistry (Wiley), and S. R. Sandler and W. Karo "Organic Functional Group Preparations."

From the perspective of enhancing reverse wavelength dispersion of optical film etc., in the disclosed mixture, $FG^1$, $A^1$, $L^1$, $B^1$, $Y^1$, $R^1$, b and c of compound (I) are preferably the same as $FG^2$, $A^2$, $L^2$, $B^2$, $Y^2$, $R^3$, d and e of compound (II), respectively. Specifically, compound (II) preferably has the same structure as compound (I) except for the absence of —$(CH_2CHR^1COO)_a$-between $CH_2CR^1COO$— and —$(CH_2)_b$—.

The mixture can be prepared for example by mixing compounds (I) and (II) at desired ratios.

Further, a mixture of compound (I) where c is 0 and compound (II) where e is 0 can be obtained by any method, e.g., by reacting mixture (D) with a compound having the following formula:

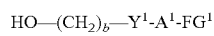

where $Y^1$, $A^1$, $FG^1$ and b are as defined in Formula (I).

Further, a mixture of compound (I) where c is 1 and compound (II) where e is 1 can be obtained by any method, e.g., by reacting a mixture containing compound (I) where c is 0 and compound (II) where e is 0 with a compound having the following formula:

$L^3$-$A^1$-$FG^3$ where $L^3$ represent a group which may form —O—, —CO—, —CO—O—, —O—CO—, —NR$^{21}$—CO—, —CO—NR$^{22}$—, —O—CO—O—, —NR$^{23}$—CO—O—, —O—CO—NR$^{24}$— or —NR$^{25}$—CO—NR$^{26}$— by reaction with $FG^1$ of compound (I) where c is 0 and $FG^2$ of compound (II) where e is 0, with the proviso that $R^{21}$ to $R^{26}$ are each independently hydrogen or C1-C6 alkyl group; $A^1$ is as defined in Formula (I); and $FG^3$ represents hydroxyl group, carboxyl group or amino group.

The mixture of compound (I) where c is 1 and compound (II) where e is 1 may further contain a compound having Formula (a) shown below. The amount of the compound having Formula (a) is 0.05 to 60 mass %, preferably 0.05 to 50 mass %, more preferably 0.05 to 35 mass %, of the total amount of compound (I) where c is 1 and compound (II) where e is 1.

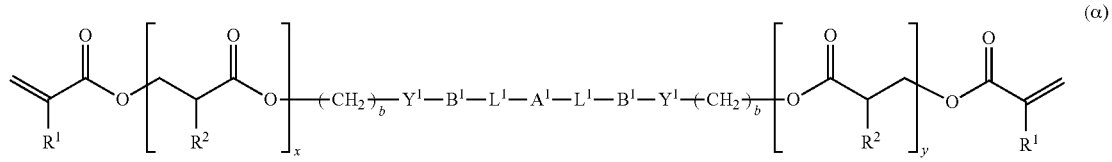

(α)

where $Y^1$, $B^1$, $L^1$, $A^1$, $R^1$, $R^2$ and b are as defined in Formula (I), and x and y represent each independently an integer of 0 to 3.

A preferred example of compound (II) where e is 0 includes, but not limited to, a compound having the following Formula (IIa) (hereinafter occasionally referred to as "compound (IIa)"):

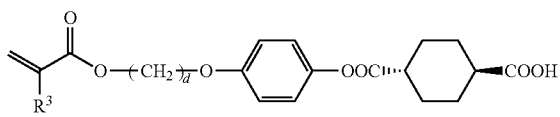

(IIa)

where $R^3$ and d are as defined in Formula (II).

Compound (IIa) can be produced by any of the methods known in the art, e.g., by the method described in PTL 1.

The mixture containing compounds (Ia) and (IIa) can be prepared for example by mixing compounds (Ia) and (IIa) at desired ratios.

The mixture containing compounds (Ia) and (IIa) can also be obtained for example by replacing compound (4) by mixture (D) in the above-described method of producing compound (Ia) as shown below.

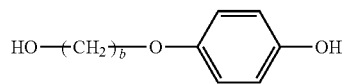

(3)

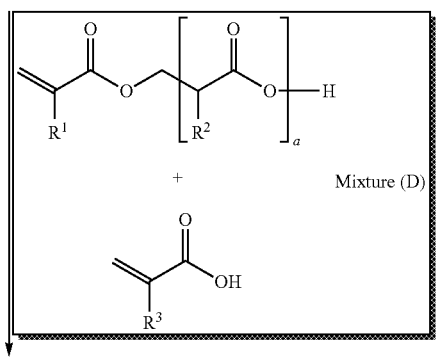

Mixture (D)

-continued

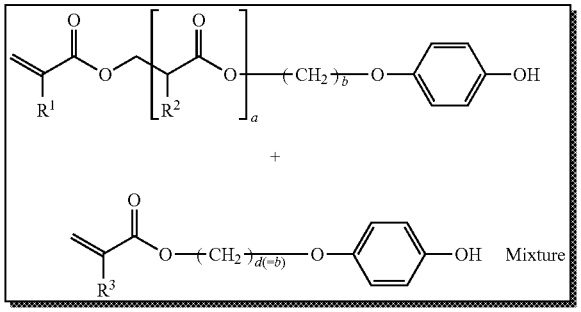

Mixture where $R^1$, $R^2$, a and b are as defined in Formula (I), and $R^3$ and d(=b) are as defined in Formula (II).

A preferred example of compound (II) where e is 1 includes, but not limited to, a compound having the following Formula (IVa) (hereinafter occasionally referred to as "compound (IVa)"):

(IVa)

where $R^3$ and d are as defined in Formula (II).

Compound (IVa) can be produced by any of the methods known in the art, e.g., by the method described in PTL 1.

The mixture containing compounds (IIIa) and (IVa) can be prepared for example by mixing compounds (IIIa) and (IVa) at desired ratios.

The mixture containing compounds (IIIa) and (IVa) can also be obtained for example by replacing compound (Ia) with the mixture containing compounds (Ia) and (IIa) in the above-described method of producing compound (IIIa) as shown below.

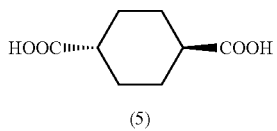

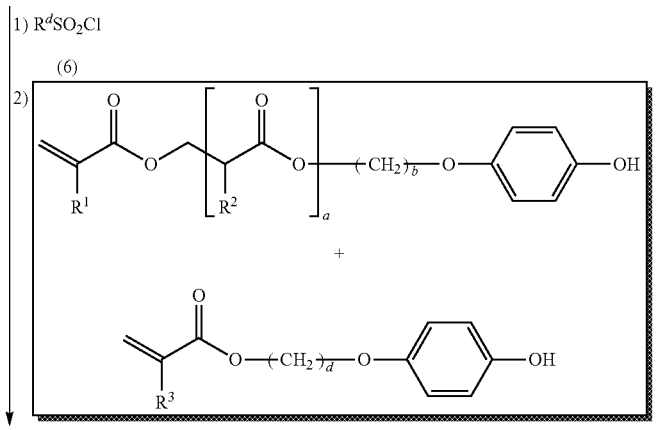

where $R^1$, $R^2$, a and b are as defined in Formula (I), $R^3$ and d are as defined in Formula (II), and $R^d$ is as defined in Formula (6).

(3) Polymerizable Compound

The disclosed polymerizable compound is a compound having Formula (III) shown below (hereinafter occasionally referred to as "polymerizable compound (III)") and can be advantageously used for the preparation of a polymer, an optical film and an optically anisotropic product which are described later.

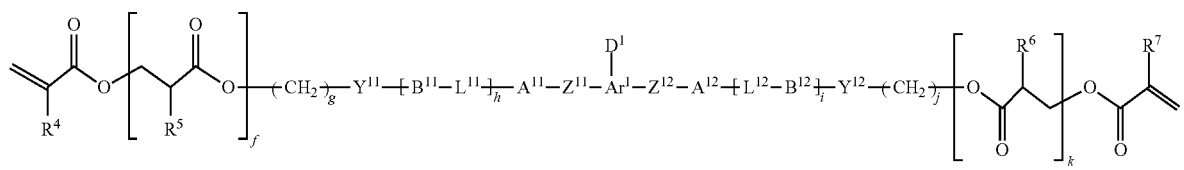

(III)

As will be described later, the use of a mixture of polymerizable compound (III) and polymerizable compound (IV) (compound having Formula (IV)) to be described in detail later makes it possible to obtain a polymerizable liquid crystal composition which can retain liquid crystal phase more stably over long periods of time, has a wide process margin, has a low melting point suitable for practical use, has superior solubility in common solvents, and allows for the low-cost manufacture of optical film etc. which are capable of uniform polarized light conversion over a wide wavelength range.

A possible but still uncertain reason for this is that polymerizable compound (III) has a moiety represented by $-(CH_2CHR^5COO)_f-$ and/or a moiety represented by $-(OCOCHR^6CH_2)_k-$ and hence the use of a mixture of polymerizable compounds (III) and (IV) results in the formation of a liquid crystal layer that easily turns into liquid crystal phase at lower temperatures (i.e., easily becomes supercooling state at room temperature) compared to cases where only polymerizable compound (IV) is used while ensuring optical characteristics (especially reverse wavelength dispersion), so that optical film etc. having a polymer as the constituent material can be obtained.

It should be noted that polymerizable compound (III) also can be used alone for the preparation of polymerizable liquid crystal compositions, polymers, and optical film etc. containing the polymer as the constituent material, without being mixed with polymerizable compound (IV).

In Formula (III), one of f and k is an integer of 1 to 3 and the other is an integer of 0 to 3, g and j are each independently an integer of 1 to 20, preferably an integer of 2 to 12, more preferably an integer of 4 to 8, and h and i are each independently 0 or 1, preferably 1.

$Ar^1$ is divalent aromatic hydrocarbon ring group having $D^1$ as a substituent or divalent heteroaromatic ring group having $D^1$ as a substituent. $D^1$ is C1-C20 organic group having at least one aromatic ring selected from the group consisting of an aromatic hydrocarbon ring and a heteroaromatic ring.

The divalent aromatic hydrocarbon ring group having $D^1$ as a substituent or divalent heteroaromatic ring group having $D^1$ as a substituent refers to a group obtained by removing, from the ring moiety of the aromatic hydrocarbon ring or heteroaromatic ring to which $D^1$ is bound, two hydrogens attached to carbon atoms other than the carbon atom to which $D^1$ is bound.

Examples of the divalent aromatic hydrocarbon ring group for $Ar^1$ include 1,4-phenylene group, 1,3-phenylene group, 1,4-naphthylene group, 2,6-naphthylene group, 1,5-naphthylene group, anthracenyl-9,10-diyl group, anthracenyl-1,4-diyl group, and anthracenyl-2,6-diyl group.

Of these divalent aromatic hydrocarbon ring groups, preferred is 1,4-phenylene group, 1,4-naphthylene group or 2,6-naphthylene group.

Examples of the divalent heteroaromatic ring group for $Ar^1$ include benzothiazole-4,7-diyl group, 1,2-benzisothiazole-4,7-diyl group, benzoxazole-4,7-diyl group, indonyl-4,7-diyl group, benzimidazole-4,7-diyl group, benzopyrazole-4,7-diyl group, 1-benzofuran-4,7-diyl group, 2-benzofuran-4,7-diyl group, benzo[1,2-d:4,5-d']dithiazolyl-4,8-diyl group, benzo[1,2-d:5,4-d']dithiazolyl-4,8-diyl group, benzothiophenyl-4,7-diyl group, 1H-isoindole-1,3(2H)-dione-4,7-diyl group, benzo[1,2-b:5,4-b']dithiophenyl-4,8-diyl group, benzo[1,2-b:4,5-b']dithiophenyl-4,8-diyl group, benzo[1,2-b:5,4-b']difuranyl-4,8-diyl group, benzo[1,2-b:4,5-b']difuranyl-4,8-diyl group, benzo[2,1-b:4,5-b']dipyrrole-4,8-diyl group, benzo[1,2-b:5,4-b']dipyrrole-4,8-diyl group, and benzo[1,2-d:4,5-d']diimidazole-4,8-diyl group.

Of these divalent heteroaromatic ring groups, preferred is benzothiazole-4,7-diyl group, benzoxazole-4,7-diyl group, 1-benzofuran-4,7-diyl group, 2-benzofuran-4,7-diyl group, benzo[1,2-d:4,5-d']dithiazolyl-4,8-diyl group, benzo[1,2-d:5,4-d']dithiazolyl-4,8-diyl group, benzothiophenyl-4,7-diyl group, 1H-isoindole-1,3(2H)-dione-4,7-diyl group, benzo[1,2-b:5,4-b']dithiophenyl-4,8-diyl group, benzo[1,2-b:4,5-b']dithiophenyl-4,8-diyl group, benzo[1,2-b:5,4-b']difuranyl-4,8-diyl group or benzo[1,2-b:4,5-b']difuranyl-4,8-diyl group.

The divalent aromatic hydrocarbon ring group and divalent heteroaromatic ring group for $Ar^1$ may have, in addition to $D^1$, at least one substituent selected from C1-C6 alkyl group such as methyl group, ethyl group, propyl group, isopropyl group, butyl group, sec-butyl group, and tert-butyl group. When more than one substituent occurs, each substituent may be the same or different. Preferred for the divalent aromatic hydrocarbon ring group and divalent heteroaromatic ring group other than $D^1$ is at least one substituent selected from methyl group, ethyl group, propyl group, sec-butyl group, and tert-butyl group.

By the term "aromatic ring" used in "C1-C20 organic group having at least one aromatic ring selected from the group consisting of an aromatic hydrocarbon ring and a heteroaromatic ring" for $D^1$ is meant a cyclic structure that has aromaticity in a broad sense following Huckel's rule, i.e., a cyclic conjugated structure having (4n+2) π electrons, as well as a cyclic structure that exhibits aromaticity due to involvement of a lone electron pair of a hetero atom such as sulfur, oxygen or nitrogen with the π electron system, as represented by the cyclic structure of thiophene, furan, benzothiazole or the like.

The aromatic ring of D1 may have one or more substituents.

The total number of π electrons in $Ar^1$ and $D^1$ is typically 12 or more, preferably 12 to 22, more preferably 12 to 20.

Examples of the aromatic hydrocarbon ring for $D^1$ include benzene ring, naphthalene ring, anthracene ring, phenanthrene ring, pyrene ring, and fluorine ring.

Of these aromatic hydrocarbon rings, preferred are benzene ring and naphthalene ring.

Examples of the heteroaromatic ring for $D^1$ include 1H-isoindole-1,3(2H)-dione ring, 1-benzofuran ring, 2-benzofuran ring, acridine ring, isoquinoline ring, imidazole ring, indole ring, oxadiazole ring, oxazole ring, oxazolopyrazine ring, oxazolopyridine ring, oxazolopyridazyl ring, oxazolopyrimidine ring, quinazoline ring, quinoxaline ring, quinoline ring, cinnoline ring, thiadiazole ring, thiazole ring, thiazolopyrazine ring, thiazolopyridine ring, thiazolopyridazine ring, thiazolopyrimidine ring, thiophene ring, triazine ring, triazole ring, naphthyridine ring, pyrazine ring, pyrazole ring, pyranone ring, pyran ring, pyridine ring, pyridazine ring, pyrimidine ring, pyrrole ring, phenanthridine ring, phthalazine ring, furan ring, benzo[c]thiophene ring, benzisoxazole ring, benzisothiazole ring, benzimidazole ring, benzoxadiazole ring, benzoxazole ring, benzothiadiazole ring, benzothiazole ring, benzothiophene ring, benzotriazine ring, benzotriazole ring, benzopyrazole ring, benzopyranone ring, dihydropyran ring, tetrahydropyran ring, dihydrofuran ring, and tetrahydrofuran ring.

Of these heteroaromatic rings, preferred are benzothiazole ring, benzoxazole ring, 1-benzofuran ring, 2-benzofuran ring, benzothiophene ring, 1H-isoindole-1,3(2H)-dione ring, thiophene ring, furan ring, benzo[c]thiophene ring, oxazole ring, thiazole ring, oxadiazole ring, pyran ring, benzisoxazole ring, thiadiazole ring, benzoxadiazole ring, and benzothiadiazole ring.

Examples of the C1-C20 organic group having at least one aromatic ring selected from the group consisting of an aromatic hydrocarbon ring and a heteroaromatic ring for $D^1$ include, but not limited to, an aromatic hydrocarbon ring group which may have a substituent, a heteroaromatic ring group which may have a substituent, and a group having the formula —$R^f$C(=N—NR$^g$R$^h$).

In the formula, $R^f$ represents hydrogen or C1-C6 alkyl group such as methyl group, ethyl group, propyl group or isopropyl group.

In the formula, $R^g$ represents hydrogen or C1-C20 organic group which may have a substituent. Specific examples of the C1-C20 organic group and substituents thereon for $R^g$ are the same as those exemplified for Ra described later.

In the formula, $R^h$ represents C2-C20 organic group having at least one aromatic ring selected from the group consisting of an aromatic hydrocarbon ring and a heteroaromatic ring. Specific examples of the C2-C20 organic group and substituents thereon for $R^h$ are the same as those exemplified for Ax described later.

More specifically, examples of the aromatic hydrocarbon ring group which serves as $D^1$ include phenyl group, naphthyl group, anthracenyl group, phenanthrenyl group, pyrenyl group, and fluorenyl group.

Of these aromatic hydrocarbon ring groups, preferred are phenyl group and naphthyl group.

Examples of the heteroaromatic ring group which serves as $D^1$ include phthalimide group, 1-benzofuranyl group, 2-benzofuranyl group, acrydinyl group, isoquinolinyl group, imidazolyl group, indolinyl group, furazanyl group, oxazolyl group, oxazolopyrazinyl group, oxazolopyridinyl group, oxazolopyridazinyl group, oxazolopyrimidinyl group, quinazolinyl group, quinoxalinyl group, quinolyl group, cinnolinyl group, thiadiazolyl group, thiazolyl group, thiazolopyrazinyl group, thiazolopyridyl group, thiazolopyridazinyl group, thiazolopyrimidinyl group, thienyl group, triazinyl group, triazolyl group, naphthyridinyl group, pyrazinyl group, pyrazolyl group, pyranonyl group, pyranyl group, pyridyl group, pyridazinyl group, pyrimidinyl group, pyrrolyl group, phenanthridinyl group, phthalazinyl group, furanyl group, benzo[c]thienyl group, benzisoxazolyl group, benzisothiazolyl group, benzimidazolyl group, benzoxazolyl group, benzothiadiazolyl group, benzothiazolyl group, benzothienyl group, benzotriadinyl group, benzotriazolyl group, benzopyrazolyl group, benzopyranonyl group, dihydropyranyl group, tetrahydropyranyl group, dihydrofuranyl group, and tetrahydrofuranyl group.

Of these heteroaromatic ring groups, preferred are furanyl group, thienyl group, oxazolyl group, thiazolyl group, benzothiazolyl group, benzoxazolyl group, 1-benzofuranyl group, 2-benzofuranyl group, benzothienyl group, and thiazolopyridyl group.

The aromatic hydrocarbon ring group and heteroaromatic ring group which serve as $D^1$ may have at least one substituent selected from C1-C20 aliphatic hydrocarbon group such as methyl group, ethyl group, propyl group, isopropyl group, butyl group, and sec-butyl group; halogens such as fluorine and chlorine; cyano group; substituted-amino group such as dimethylamino group; C1-C6 alkoxy group such as methoxy group, ethoxy group, and isopropoxy group; nitro group; C3-C8 cycloalkyl group such as cyclopentyl group and cyclohexyl group; C1-C6 halogenated alkyl group such as trifluoromethyl group; —C(=O)—$R^{b'}$; —C(=O) —OR$^{b'}$; —SR$^{b'}$; —SO$_2$R$^{d'}$; and hydroxyl group, where $R^{b'}$ represents C1-C20 alkyl group which may have a substituent, C2-C20 alkenyl group which may have a substituent, C3-C12 cycloalkyl group which may have a substituent, or C5-C12 aromatic hydrocarbon ring group which may have a substituent, and $R^{d'}$ represents C1-C6 alkyl group such as methyl group and ethyl group; or C6-C20 aromatic hydrocarbon ring group which may have a substituent, such as phenyl group, 4-methyl phenyl group and 4-methoxyphenyl group. When the aromatic hydrocarbon ring group and heteroaromatic ring group have more than one substituent, each substituent may be the same or different.

Examples of the substituents on the C1-C20 alkyl, C2-C20 alkenyl and C5-C12 aromatic hydrocarbon ring groups which may have a substituent for $R^{b'}$ include halogens such as fluorine and chlorine; cyano group; C1-C20 alkoxy group such as methoxy group, ethoxy group, isopropoxy group, and butoxy group; nitro group; C6-C20 aromatic hydrocarbon ring group such as phenyl group and naphthyl group; C2-20 heteroaromatic ring group such as furanyl group and thiophenyl group; C3-C8 cycloalkyl group such as cyclopropyl group, cyclopentyl group, and cyclohexyl group; and C1-C12 fluoroalkyl group at least one hydrogen of which is replaced by fluorine, such as trifluoromethyl group, pentafluoroethyl group, and —CH$_2$CF$_3$. The C1-20 alkyl group, C2-C20 alkenyl group and C5-C12 aromatic hydrocarbon ring group for $R^{b'}$ may have one or more substituents selected from those described above. When they have more than one substituent, each substituent may be the same or different.

Examples of the substituent on the C3-C12 cycloalkyl group for $R^{b'}$ include halogens such as fluorine and chlorine; cyano group; C1-C6 alkyl group such as methyl group, ethyl group and propyl group; C1-C6 alkoxy group such as methoxy group, ethoxy group and isopropoxy group; nitro group; and C6-C20 aromatic hydrocarbon group such as phenyl group and naphthyl group. The C3-C12 cycloalkyl group for $R^{b'}$ may have one or more substituents selected from those described above. When it has more than one substituent, each substituent may be the same or different.

Examples of combinations of Ar$^1$ and D$^1$ (Ar$^1$-D$^1$) include phenylene group substituted with a group having the formula —$R^f$C(=N—NR$^g$R$^h$), benzothiazole-4,7-diyl group substituted with 1-benzofuran-2-yl group, benzothiazole-4,7-diyl group substituted with 5-(2-butyl)-1-benzofuran-2-yl group, benzothiazole-4,7-diyl group substituted with 4,6-dimethyl-1-benzofuran-2-yl group, benzothiazole-4,7-diyl group substituted with 6-methyl-1-benzofuran-2-yl group, benzothiazole-4,7-diyl group substituted with 4,6,7-trimethyl-1-benzofuran-2-yl group, benzothiazole-4,7-diyl group substituted with 4,5,6-trimethyl-1-benzofuran-2-yl group, benzothiazole-4,7-diyl group substituted with 5-methyl-1-benzofuran-2-yl group, benzothiazole-4,7-diyl group substituted with 5-propyl-1-benzofuran-2-yl group, benzothiazole-4,7-diyl group substituted with 7-propyl-1-benzofuran-2-yl group, benzothiazole-4,7-diyl group substituted with 5-fluoro-1-benzofuran-2-yl group, benzothiazole-4,7-diyl group substituted with phenyl group, benzothiazole-4,7-diyl group substituted with 4-fluorophenyl group, benzothiazole-4,7-diyl group substituted with 4-nitrophenyl group, benzothiazole-4,7-diyl group substituted with 4-trifluoromethylphenyl group, benzothiazole-4,7-diyl group substituted with 4-cyanophenyl group, benzothiazole-4,7-diyl group substituted with 4-methanesulfonylphenyl group, benzothiazole-4,7-diyl group substituted with thiophene-2-yl group, benzothiazole-4,7-diyl group substituted with thiophene-3-yl group, benzothiazole-4,7-diyl group substituted with 5-methylthiophene-2-yl group, benzothiazole-4,7-diyl group substituted with 5-chlorothiophene-2-yl group, benzothiazole-4,7-diyl group substituted with thieno[3,2-b]thiophene-2-yl group, benzothiazole-4,7-diyl group substituted with 2-benzothiazolyl group, benzothiazole-4,7-diyl group substituted with 4-biphenyl group, benzothiazole-4,7-diyl group substituted with 4-propylbiphenyl group, benzothiazole-4,7-diyl group substituted with 4-thiazolyl group, benzothiazole-4,7-diyl group substituted with 1-phenylethylene-2-yl group, benzothiazole-4,7-diyl group substituted with 4-pyridyl group, benzothiazole-4,7-diyl group substituted with 2-furyl group, benzothiazole-4,7-diyl group substituted with naphtho[1,2-b]furan-2-yl group, 1H-isoindole-1,3(2H)-dione-4,7-diyl group substituted with 5-methoxy-2-benzothiazolyl group, 1H-isoindole-1,3(2H)-dione-4,7-diyl group substituted with phenyl group, 1H-isoindole-1,3(2H)-dione-4,7-diyl group substituted with 4-nitrophenyl group, and 1H-isoindole-1,3(2H)-dione-4,7-diyl group substituted with 2-thiazolyl group. $R^f$, $R^g$ and $R^h$ in the formula —$R^fC(=N-NR^gR^h)$ are as defined above.

$Ar^1$-$D^1$ is preferably a divalent group having the following Formula (V):

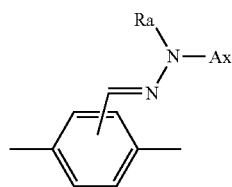

(V)

where Ax represents C2-C20 organic group having at least one aromatic ring selected from the group consisting of an aromatic hydrocarbon ring and a heteroaromatic ring, and Ra represents hydrogen or C1-C20 organic group which may have a substituent.

In the present disclosure, a moiety having the following Formula (i) refers to a moiety having the following Formula (ia) and/or Formula (iib).

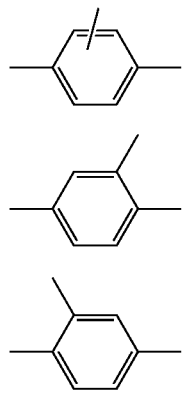

By the term "aromatic ring" used in "C2-C20 organic group having at least one aromatic ring selected from the group consisting of an aromatic hydrocarbon ring and a heteroaromatic ring" for Ax is meant a cyclic structure that has aromaticity in a broad sense following Huckel's rule, i.e., a cyclic conjugated structure having (4n+2) π electrons, as well as a cyclic structure that exhibits aromaticity due to involvement of a lone electron pair of a hetero atom such as sulfur, oxygen or nitrogen with the π electron system, as represented by the cyclic structure of thiophene, furan, benzothiazole or the like.

The C2-C20 organic group having at least one aromatic ring selected from the group consisting of an aromatic hydrocarbon ring and a heteroaromatic ring for Ax may have more than aromatic ring or may have an aromatic hydrocarbon ring and a heteroaromatic ring.

Examples of the aromatic hydrocarbon ring for Ax include benzene ring, naphthalene ring, anthracene ring, phenanthrene ring, pyrene ring, fluorene ring.

Of these aromatic hydrocarbon rings, preferred are benzene ring and naphthalene ring.

Examples of the heteroaromatic ring for Ax include 1H-isoindole-1,3(2H)-dione ring, 1-benzofuran ring, 2-benzofuran ring, acridine ring, isoquinoline ring, imidazole ring, indole ring, oxadiazole ring, oxazole ring, oxazolopyrazine ring, oxazolopyridine ring, oxazolopyridazyl ring, oxazolopyrimidine ring, quinazoline ring, quinoxaline ring, quinoline ring, cinnoline ring, thiadiazole ring, thiazole ring, thiazolopyrazine ring, thiazolopyridine ring, thiazolopyridazine ring, thiazolopyrimidine ring, thiophene ring, triazine ring, triazole ring, naphthyridine ring, pyrazine ring, pyrazole ring, pyranone ring, pyran ring, pyridine ring, pyridazine ring, pyrimidine ring, pyrrole ring, phenanthridine ring, phthalazine ring, furan ring, benzo[c]thiophene ring, benzisoxazole ring, benzisothiazole ring, benzimidazole ring, benzoxadiazole ring, benzoxazole ring, benzothiadiazole ring, benzothiazole ring, benzothiophene ring, benzotriazine ring, benzotriazole ring, benzopyrazole ring, benzopyranone ring, dihydropyran ring, tetrahydropyran ring, dihydrofuran ring, and tetrahydrofuran ring.

Of these heteroaromatic rings, preferred are monocyclic heteroaromatic rings such as furan ring, thiophene ring, oxazole ring, and thiazole ring; and condensed heteroaromatic rings such as benzothiazole ring, benzoxazole ring, quinoline ring, 1-benzofuran ring, 2-benzofuran ring, benzothiophene ring, thiazolopyridine ring, and thiazolopyrazine ring.

The aromatic ring of Ax may have a substituent. Examples of the substituent include halogens such as fluorine and chlorine; cyano group; C1-C6 alkyl group such as methyl group, ethyl group, and propyl group; C2-C6 alkenyl group such as vinyl group and allyl group; C1-C6 halogenated alkyl group such as trifluoromethyl group; substituted amino group such as dimethylamino group; C1-C6 alkoxy group such as methoxy group, ethoxy group, and isopropoxy group; nitro group; C6-C20 aromatic hydrocarbon ring group such as phenyl group and naphthyl group; —C(=O)—$R^b$; —C(=O)—O$R^b$; and —SO$_2R^d$, where $R^b$ represents C1-C20 alkyl group which may have a substituent, C2-C20 alkenyl group which may have a substituent, C3-C12 cycloalkyl group which may have a substituent, or C5-C12 aromatic hydrocarbon ring group which may have a substituent, and $R^d$ represents C1-C6 alkyl group such as methyl group and ethyl group, or C6-C20 aromatic hydrocarbon ring group which may have a substituent, such as phenyl group, 4-methyl phenyl group, and 4-methoxyphenyl group. Of these substituents on the aromatic ring of Ax, preferred are halogens, cyano group, C1-C6 alkyl group, and C1-C6 alkoxy group.

Ax may have more than one substituent selected from those described above. When Ax has more than one substituent, each substituent may be the same or different.

Examples of the C1-C20 alkyl group of the C1-C20 alkyl group which may have a substituent for $R^b$ include methyl group, ethyl group, n-propyl group, isopropyl group, n-butyl group, isobutyl group, 1-methylpentyl group, 1-ethylpentyl group, sec-butyl group, t-butyl group, n-pentyl group, isopentyl group, neopentyl group, n-hexyl group, isohexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group, and n-icosyl group. The C1-C20 alkyl group which may have a substituent preferably has 1 to 12 carbon atoms, more preferably 4 to 10 carbon atoms.

Examples of the C2-C20 alkenyl group of the C2-C20 alkenyl group which may have a substituent for $R^b$ include vinyl group, propenyl group, isopropenyl group, butenyl group, isobutenyl group, pentenyl group, hexenyl group, heptenyl group, octenyl group, decenyl group, undecenyl group, dodecenyl group, tridecenyl group, tetradecenyl group, pentadecenyl group, hexadecenyl group, heptadecenyl group, octadecenyl group, nonadecenyl group, and icocenyl group.

The C2-C20 alkenyl group which may have a substituent preferably has 2 to 12 carbon atoms.

Examples of the substituents on the C1-C20 alkyl group and C2-20 alkenyl group for $R^b$ include halogens such as fluorine and chlorine; cyano group; substituted amino group such as dimethylamino group; C1-C20 alkoxy group such as methoxy group, ethoxy group, isopropoxy group, and butoxy group; C1-C12 alkoxy group substituted with C1-C12 alkoxy group, such as methoxymethoxy group and methoxyethoxy group; nitro group; C6-C20 aromatic hydrocarbon ring group such as phenyl group and naphthyl group; C2-C20 heteroaromatic ring group such as triazolyl group, pyrrolyl group, furanyl group, and thiophenyl group; C3-C8 cycloalkyl group such as cyclopropyl group, cyclopentyl group, and cyclohexyl group; C3-C8 cycloalkyloxy group such as cyclopentyloxy group and cyclohexyloxy group; C2-C12 cyclic ether group such as tetrahydrofuranyl group, tetrahydropyranyl group, dioxolanyl group, and dioxanyl group; C6-C14 aryloxy group such as phenoxy group and naphthoxy group; C1-C12 fluoroalkyl group at least one hydrogen of which is replaced by fluorine, such as trifluoromethyl group, pentafluoroethyl group, and —$CH_2CF_3$; benzofuryl group; benzopyranyl group; benzodioxolyl group; and benzodioxanyl group. Of these substituents on the C1-C20 alkyl group and C2-C20 alkenyl group for $R^b$, preferred are halogens such as fluorine and chlorine; cyano group; C1-C20 alkoxy group such as methoxy group, ethoxy group, isopropoxy group, and butoxy group; nitro group; C6-C20 aromatic hydrocarbon ring group such as phenyl group and naphthyl group; C2-C20 heteroaromatic ring group such as furanyl group and thiophenyl group; C3-C8 cycloalkyl group such as cyclopropyl group, cyclopentyl group, and cyclohexyl group; and C1-C12 fluoroalkyl group at least one hydrogen of which is replaced by fluorine, such as trifluoromethyl group, pentafluoroethyl group, and —$CH_2CF_3$.

The C1-C20 alkyl group and C2-C20 alkenyl group for $R^b$ may have more than one substituent selected from those described above. When the C1-C20 alkyl group and C2-C20 alkenyl group for $R^b$ have more than one substituent, each substituent may be the same or different.

Examples of the C3-C12 cycloalkyl group of the C3-C12 cycloalkyl group which may have a substituent for $R^b$ include cyclopropyl group, cyclobutyl group, cyclopentyl group, cyclohexyl group, and cyclooctyl group. Of these cycloalkyl groups, preferred are cyclopentyl group and cyclohexyl group.

Examples of the substituent on the C3-C12 cycloalkyl group for $R^b$ include halogens such as fluorine and chlorine; cyano group; substituted amino group such as dimethylamino group; C1-C6 alkyl group such as methyl group, ethyl group, and propyl group; C1-C6 alkoxy group such as methoxy group, ethoxy group, and isopropoxy group; nitro group; and C6-C20 aromatic hydrocarbon group such as phenyl group and naphthyl group. Of these substituents on the C3-C12 cycloalkyl group for $R^b$, preferred are halogens such as fluorine and chlorine; cyano group; C1-C6 alkyl group such as methyl group, ethyl group, and propyl group; C1-C6 alkoxy group such as methoxy group, ethoxy group, and isopropoxy group; nitro group; and C6-C20 aromatic hydrocarbon group such as phenyl group and naphthyl group.

The C3-C12 cycloalkyl group for $R^b$ may have more than one substituent. When it has more than one substituent, each substituent may be the same or different.

Examples of the C5-C12 aromatic hydrocarbon ring group of the C5-C12 aromatic hydrocarbon ring group which may have a substituent for $R^b$ include phenyl group, 1-naphthyl group, and 2-naphthyl group, with phenyl group being preferred.

Examples of the substituent on the C5-C12 aromatic hydrocarbon ring group which may have a substituent include halogens such as fluorine and chlorine; cyano group; substituted amino group such as dimethylamino group; C1-C20 alkoxy group such as methoxy group, ethoxy group, isopropoxy group, and butoxy group; C1-C12 alkoxy group substituted with C1-C12 alkoxy group, such as methoxymethoxy group and methoxyethoxy group; nitro group; C6-C20 aromatic hydrocarbon ring group such as phenyl group and naphthyl group; C2-C20 heteroaromatic ring group such as triazolyl group, pyrrolyl group, furanyl group, and thiophenyl group; C3-C8 cycloalkyl group such as cyclopropyl group, cyclopentyl group, and cyclohexyl group; C3-C8 cycloalkyloxy group such as cyclopentyloxy group and cyclohexyloxy group; C2-C12 cyclic ether group such as tetrahydrofuranyl group, tetrahydropyranyl group, dioxolanyl group, and dioxanyl group; C6-C14 aryloxy group such as phenoxy group and naphthoxy group; C1-C12 fluoroalkyl group at least one hydrogen of which is replaced by fluorine, such as trifluoromethyl group, pentafluoroethyl group, and —$CH_2CF_3$; benzofuryl group; benzopyranyl group; benzodioxolyl group; and benzodioxanyl group. Of these substituents on the C5-C12 aromatic hydrocarbon ring group, preferred is at least one substituent selected from halogens such as fluorine and chlorine; cyano group; C1-C20 alkoxy group such as methoxy group, ethoxy group, isopropoxy group, and butoxy group; nitro group; C6-C20 aromatic hydrocarbon ring group such as phenyl group and naphthyl group; C2-C20 heteroaromatic ring group such as furanyl group and thiophenyl group; C3-C8 cycloalkyl group such as cyclopropyl group, cyclopentyl group, and cyclohexyl group; and C1-C12 fluoroalkyl group at least one hydrogen of which is replaced by fluorine, such as trifluoromethyl group, pentafluoroethyl group, and —$CH_2CF_3$.

The C5-C12 aromatic hydrocarbon ring group may have more than one substituent. When it has more than one substituent, each substituent may be the same or different.

The aromatic ring of Ax may have two or more substituents which may be the same or different, and two adjacent substituents may be joined together to form a ring which may be a monocyclic, condensed polycyclic, unsaturated or saturated ring.

The number of carbon atoms of the C2-C20 organic group for Ax refers to a total number of carbon atoms of the whole organic group excluding the carbon atom(s) of the substituent(s).

Examples of the C2-C20 organic group having at least one aromatic ring selected from the group consisting of an aromatic hydrocarbon ring and a heteroaromatic ring for Ax include C6-C20 aromatic hydrocarbon ring group such as phenyl group, naphthyl group, anthracenyl group, phenanthrenyl group, pyrenyl group, and fluorenyl group; C2-C20 heteroaromatic ring such as phthalimide group, 1-benzofuranyl group, 2-benzofuranyl group, acrydinyl group, isoquinolinyl group, imidazolyl group, indolinyl group, furazanyl group, oxazolyl group, oxazolopyrazinyl group, oxazolopyridinyl group, oxazolopyridazinyl group, oxazolopyrimidinyl group, quinazolinyl group, quinoxalinyl group, quinolyl group, cinnolinyl group, thiadiazolyl group, thiazolyl group, thiazolopyrazinyl group, thiazolopyridinyl group, thiazolopyridazinyl group, thiazolopyrimidinyl group, thienyl group, triazinyl group, triazolyl group, naphthyridinyl group, pyrazinyl group, pyrazolyl group, pyranonyl group, pyranyl group, pyridyl group, pyridazinyl group, pyrimidinyl group, pyrrolyl group, phenanthridinyl group, phthalazinyl group, furanyl group, benzo[c]thienyl group, benzisoxazolyl group, benzisothiazolyl group, benzimidazolyl group, benzoxazolyl group, benzothiadiazolyl group, benzothiazolyl group, benzothiophenyl group, benzotriadinyl group, benzotriazolyl group, benzopyrazolyl group, benzopyranonyl group, dihydropyranyl group, tetrahydropyranyl group, dihydrofuranyl group, and tetrahydrofuranyl group; hydrocarbon ring group having at least one aromatic ring selected from the group consisting of an aromatic hydrocarbon ring and a heteroaromatic ring; heterocyclic group having at least one aromatic ring selected from the group consisting of an aromatic hydrocarbon ring and a heteroaromatic ring; C3-C20 alkyl group having at least one aromatic ring selected from the group consisting of an aromatic hydrocarbon ring and a heteroaromatic ring; C4-C20 alkenyl group having at least one aromatic ring selected from the group consisting of an aromatic hydrocarbon ring and a heteroaromatic ring; and C4-C20 alkynyl having at least one aromatic ring selected from the group consisting of an aromatic hydrocarbon ring and a heteroaromatic ring.

Specific examples of the aromatic hydrocarbon ring and heteroaromatic ring of the hydrocarbon ring group, heterocyclic group, C3-C20 alkyl group, C4-C20 alkenyl group and C4-C20 alkynyl group which have at least one aromatic ring selected from the group consisting of an aromatic hydrocarbon ring and a heteroaromatic ring are the same as those exemplified for $D^1$.

The organic group may have one or more substituents. When it has more than one substituent, each substituent may be the same or different.

Examples of the substituent include halogens such as fluorine and chlorine; cyano group; C1-C6 alkyl group such as methyl group, ethyl group, and propyl group; C2-C6 alkenyl group such as vinyl group and allyl group; C1-C6 halogenated alkyl group such as trifluoromethyl group; substituted amino group such as dimethylamino group; C1-C6 alkoxy group such as methoxy group, ethoxy group, and isopropoxy group; nitro group; C6-C20 aromatic hydrocarbon ring group such as phenyl group and naphthyl group; —C(=O)—$R^b$; —C(=O)—O$R^b$; and —SO$_2$R$^d$, where $R^b$ and $R^d$ are as defined above.

Of these substituents on the organic group of Ax, preferred is at least one substituent selected from halogens, cyano group, C1-C6 alkyl group, and C1-C6 alkoxy group.

Preferred but non-limiting specific examples of the C2-C20 organic group having at least one aromatic ring selected from the group consisting of an aromatic hydrocarbon ring and a heteroaromatic ring as Ax are shown below. In each structural formula — represents a bond at any position on the ring, which binds with nitrogen (i.e., nitrogen which binds with Ax in Formula (V)).

1) Aromatic hydrocarbon ring groups:

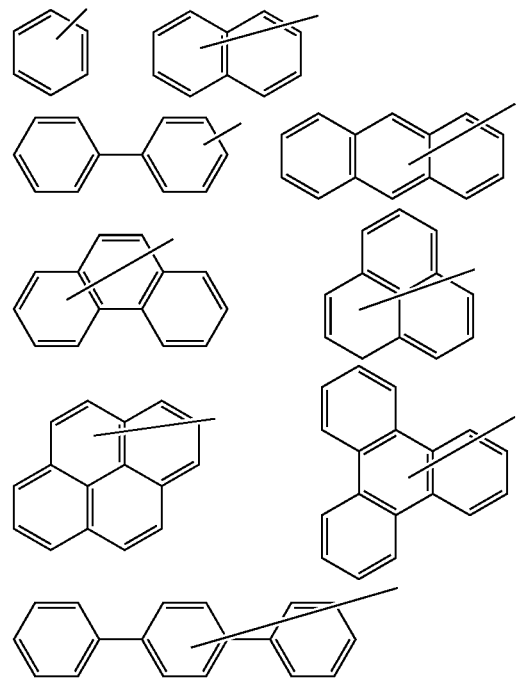

2) Heteroaromatic ring groups:

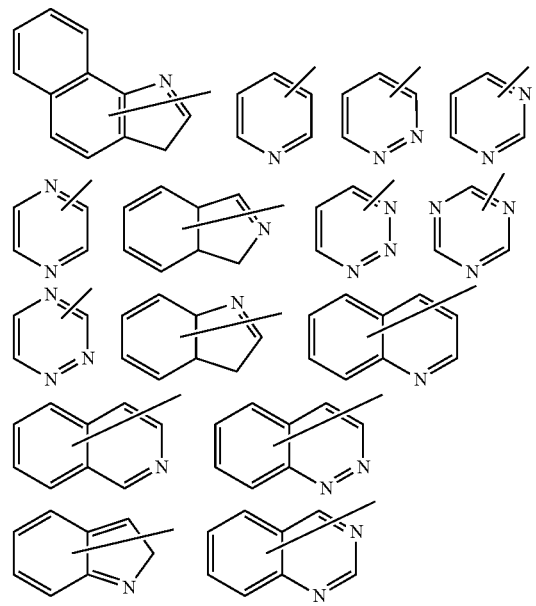

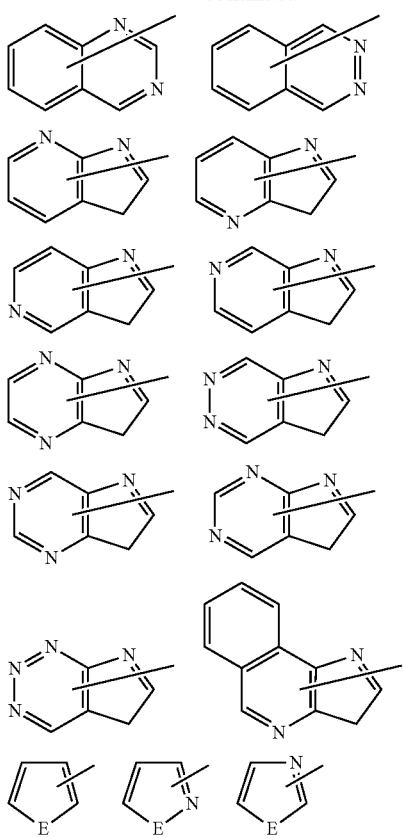

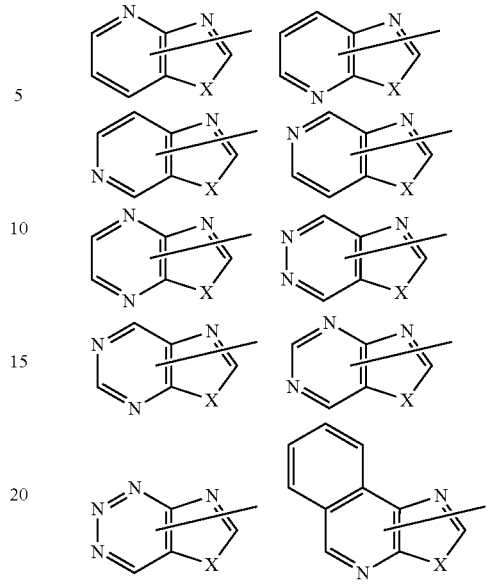

where X is as defined above.

3) Hydrocarbon ring groups having at least one aromatic ring:

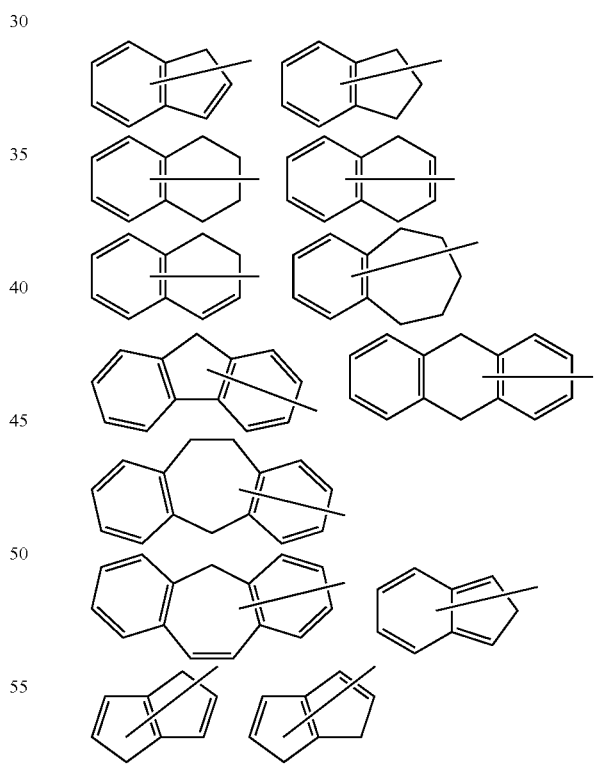

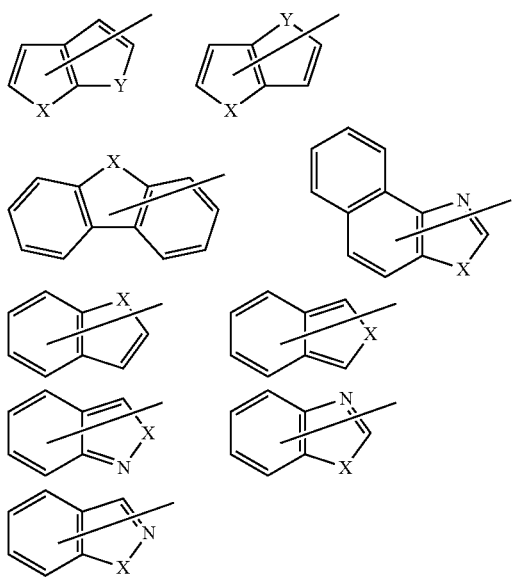

where E represents —NR$^z$—, oxygen or sulfur, where R$^z$ represents hydrogen or C1-C6 alkyl group such as methyl group, ethyl group, and propyl group.

where X and Y represent each independently —NR$^z$—, oxygen, sulfur, —SO— or —SO$_2$—, where R$^z$ represents hydrogen or C1-C6 alkyl group such as methyl group, ethyl group, and propyl group.

4) Heterocyclic groups having at least one aromatic ring:

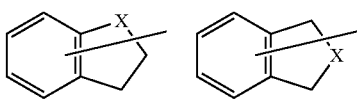

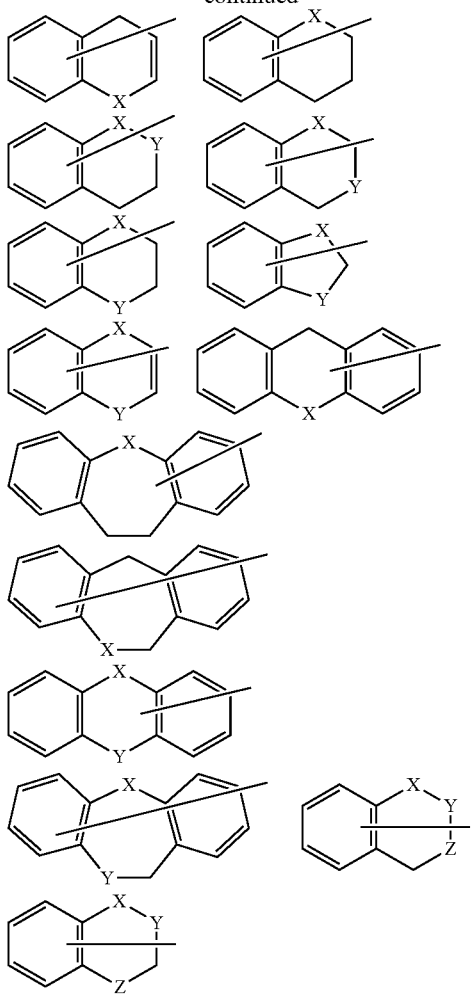

where X and Y are as defined above and Z represents —NR$^z$—, oxygen or sulfur where R$^z$ is as defined above, with the proviso that oxygen, sulfur, —SO— and —SO$_2$— are not adjacent to one another.

5) Alkyl groups having at least one aromatic ring selected from the group consisting of an aromatic hydrocarbon ring and a heteroaromatic ring:

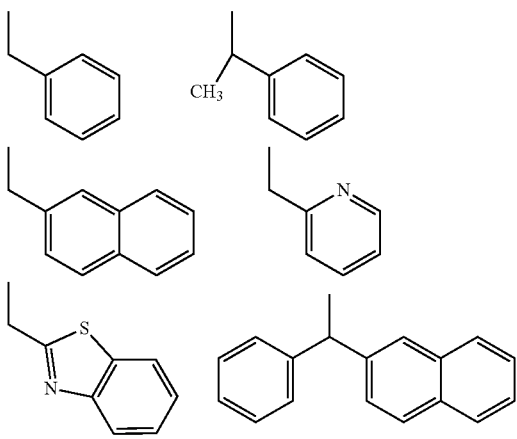

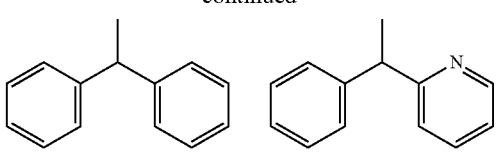

6) Alkenyl groups having at least one aromatic ring selected from the group consisting of an aromatic hydrocarbon ring and a heteroaromatic ring:

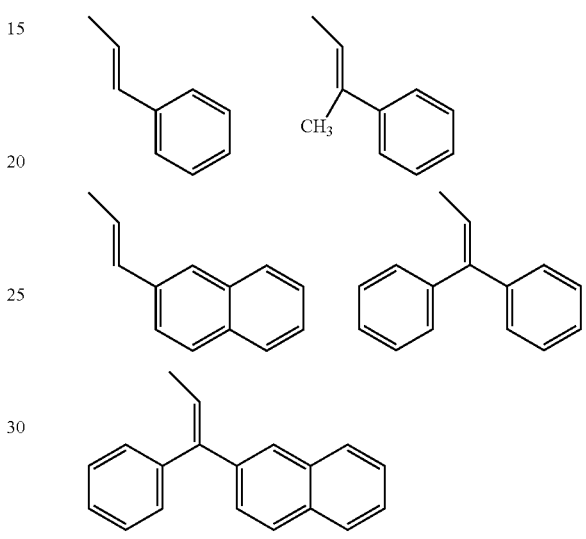

7) Alkynyl groups having at least one aromatic ring selected from the group consisting of an aromatic hydrocarbon ring and a heteroaromatic ring:

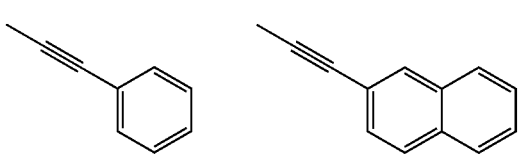

The rings of the above preferred specific examples of Ax may have one or more substituents which may be the same or different. Examples of the substituents include halogens such as fluorine and chlorine; cyano group; C1-C6 alkyl group such as methyl group, ethyl group, and propyl group; C2-C6 alkenyl group such as vinyl group and allyl group; C1-C6 halogenated alkyl group such as trifluoromethyl group; substituted amino group such as dimethylamino group; C1-C6 alkoxy group such as methoxy group, ethoxy group, and isopropoxy group; nitro group; C6-C20 aromatic hydrocarbon ring group such as phenyl group and naphthyl group; —C(=O)—R$^b$; —C(=O)—OR$^b$; and —SO$_2$R$^d$, where R$^b$ and R$^d$ are as defined above.

Of these substituents on the rings of Ax, preferred are halogens, cyano group, C1-C6 alkyl group, and C1-C6 alkoxy group.

More preferred but non-limiting specific examples of Ax are shown below.

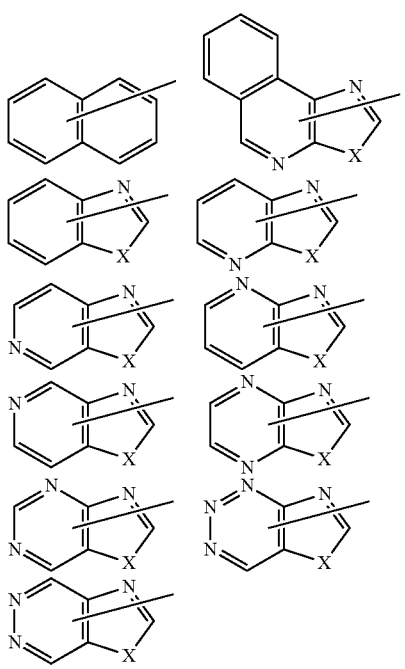

where X is as defined above.

As described above, these rings may also have one or more substituents which may be the same or different. Examples of the substituents include halogens such as fluorine, chlorine, and bromine; C1-C6 alkyl group such as methyl group, ethyl group, and propyl group; cyano group; C2-C6 alkenyl group such as vinyl group and allyl group; C1-C6 halogenated alkyl group such as trifluoromethyl group and pentafluoroethyl group; substituted amino group such as dimethylamino group; C1-C6 alkoxy group such as methoxy group, ethoxy group, and isopropoxy group; nitro group; C6-C20 aromatic hydrocarbon ring group such as phenyl group and naphthyl group; —C(=O)—$R^b$; —C(=O)—$OR^b$; and —$SO_2R^d$, where $R^b$ and $R^d$ are as defined above.

Of these substituents on the rings, preferred are halogens, cyano group, C1-C6 alkyl group, and C1-C6 alkoxy group.

Ax is even more preferably a group having the following Formula (VI):

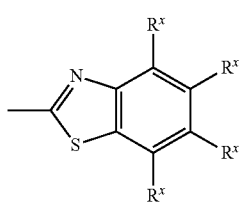

(VI)

In Formula (VI), $R^x$ represents hydrogen; halogen such as fluorine, chlorine, and bromine; C1-C6 alkyl group such as methyl group, ethyl group, and propyl group; cyano group; nitro group; C1-C6 fluoroalkyl group such as trifluoromethyl group and pentafluoroethyl group; C1-C6 alkoxy group such as methoxy group, ethoxy group, and isopropoxy group; or —C(=O)—O—$R^b$, where $R^b$ represents, as described above, C1-C20 alkyl group which may have a substituent, C2-C20 alkenyl group which may have a substituent, C3-C12 cycloalkyl group which may have a substituent, or C5-C12 aromatic hydrocarbon ring group which may have a substituent.

Each $R^x$ may be the same or different, and any of C—$R^x$ constituting the ring may be replaced by nitrogen.

Specific but non-limiting examples of the group having Formula (VI) where one or more of C—$R^x$ are replaced by nitrogen are shown below.

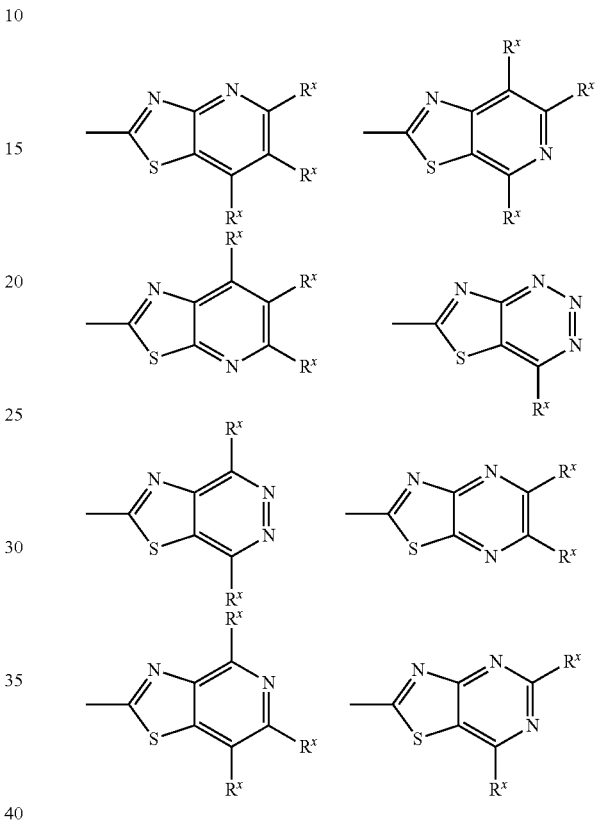

where $R^x$ is as defined above.

Of these examples of Ax, preferred is a group having Formula (VI) where all of $R^x$ are hydrogen.

Examples of the C1-C20 organic group which may have a substituent for Ra of the divalent group having Formula (V) include, but not limited to, C1-C20 alkyl group which may have a substituent, C2-C20 alkenyl group which may have a substituent, C2-20 alkynyl group which may have a substituent; C3-C12 cycloalkyl group which may have a substituent, —C(=O)—$R^b$, —$SO_2R^d$, —C(=S)NH—$R^i$, C6-C20 aromatic hydrocarbon ring group which may have a substituent, and C2-C20 heteroaromatic ring group which may have a substituent.

$R^b$ and $R^d$ are as defined above, and $R^i$ represents C1-C20 alkyl group which may have a substituent, C2-C20 alkenyl group which may have a substituent, C3-C12 cycloalkyl group which may have a substituent; C5-C20 aromatic hydrocarbon ring group which may have a substituent, or C5-C20 heteroaromatic ring group which may have a substituent.

Examples of the C1-C20 alkyl group and substituents thereof of the C1-C20 alkyl group which may have a substituent, examples of the C2-C20 alkenyl group and substituents thereof of the C2-C20 alkenyl group which may have a substituent, and examples of the C3-C12 cycloalkyl group and substituents thereof of the C3-C12 cycloalkyl group which may have a substituent for $R^i$ are the same as specific examples of the C1-C20 alkyl group and substituents thereon, C2-C20 alkenyl group and substituents thereon, and C3-C12 cycloalkyl group and substituents thereon for $R^b$. Examples of the C5-C20 aromatic hydrocarbon ring group which may have a substituent for $R^i$ include phenyl group, 1-naphthyl group, and 2-naphthyl group, and examples of the C5-C20 heteroaromatic ring group which may have a substituent include pyridinyl group and quinolyl group. Examples of substituents on these aromatic hydrocarbon ring groups and heteroaromatic ring groups are the same as those exemplified for Ax.

Examples of the C1-C20 alkyl group of the C1-C20 alkyl group which may have a substituent for Ra include methyl group, ethyl group, n-propyl group, isopropyl group, n-butyl group, isobutyl group, 1-methylpentyl group, 1-ethylpentyl group, sec-butyl group, t-butyl group, n-pentyl group, isopentyl group, neopentyl group, n-hexyl group, isohexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group, and n-icosyl group. The C1-C20 alkyl group which may have a substituent preferably has 1 to 12 carbon atoms, more preferably 1 to 10 carbon atoms.

Examples of the C2-C20 alkenyl group of the C2-C20 alkenyl group which may have a substituent for Ra include vinyl group, propenyl group, isopropenyl group, butenyl group, isobutenyl group, pentenyl group, hexenyl group, heptenyl group, octenyl group, decenyl group, undecenyl group, dodecenyl group, tridecenyl group, tetradecenyl group, pentadecenyl group, hexadecenyl group, heptadecenyl group, octadecenyl group, nonadecenyl group, and icocenyl group.

The C2-C20 alkenyl group which may have a substituent preferably has 2 to 12 carbon atoms.

Examples of the C2-C20 alkynyl group of the C2-C20 alkynyl group which may have a substituent for Ra include ethynyl group, propynyl group, 2-propynyl group (propargyl group), butynyl group, 2-butynyl group, 3-butynyl group, pentynyl group, 2-pentynyl group, hexynyl group, 5-hexynyl group, heptynyl group, octynyl group, 2-octynyl group, nonanyl group, decanyl group, and 7-decanyl group.

Examples of the C3-C12 cycloalkyl group of the C3-C12 cycloalkyl group which may have a substituent for Ra include cyclopropyl group, cyclobutyl group, cyclopentyl group, cyclohexyl group, and cyclooctyl group.

Examples of the substituents on the C1-C20 alkyl group, C2-C20 alkenyl group and C2-C20 alkynyl group for Ra include halogens such as fluorine and chlorine; cyano group; substituted amino group such as dimethylamino group; C1-C20 alkoxy group such as methoxy group, ethoxy group, isopropoxy group, and butoxy group; C1-C12 alkoxy group substituted with C1-C12 alkoxy group, such as methoxymethoxy group and methoxyethoxy group; nitro group; C6-C20 aromatic hydrocarbon ring group such as phenyl group and naphthyl group; C2-C20 heteroaromatic ring group such as triazolyl group, pyrrolyl group, furanyl group, and thiophenyl group; C3-C8 cycloalkyl group such as cyclopropyl group, cyclopentyl group, and cyclohexyl group; C3-C8 cycloalkyloxy group such as cyclopentyloxy group and cyclohexyloxy group; C2-C12 cyclic ether group such as tetrahydrofuranyl group, tetrahydropyranyl group, dioxolanyl group, and dioxanyl group; C6-C14 aryloxy group such as phenoxy group and naphthoxy group; C1-C12 fluoroalkyl group at least one hydrogen of which is replaced by fluorine, such as trifluoromethyl group, pentafluoroethyl group, and —CH$_2$CF$_3$; benzofuryl group; benzopyranyl group; benzodioxolyl group; benzodioxanyl group; —C(=O)—R$^b$; —C(=O)—OR$^b$; —SO$_2$R$^d$; —SR$^b$; C1-C12 alkoxy group substituted with —SR$^b$; and hydroxyl group, where R$^b$ and R$^d$ are as defined above.

The C1-C20 alkyl group, C2-C20 alkenyl group and C2-C20 alkynyl group for Ra may have two or more of the substituents described above, which may be the same or different.

Examples of the substituent on the C3-C12 cycloalkyl group for Ra include halogens such as fluorine and chlorine; cyano group; substituted amino group such as dimethylamino group; C1-C6 alkyl group such as methyl group, ethyl group, and propyl group; C1-C6 alkoxy group such as methoxy group, ethoxy group, and isopropoxy group; nitro group; C6-C20 aromatic hydrocarbon ring group such as phenyl group and naphthyl group; C3-C8 cycloalkyl group such as cyclopropyl group, cyclopentyl group, and cyclohexyl group; C6-C20 aromatic hydrocarbon ring group such as phenyl group and naphthyl group; —C(=O)—R$^b$; —C(=O)—OR$^b$; —SO$_2$R$^d$; and hydroxyl group, where R$^b$ and R$^d$ are as defined above.

The C3-C12 cycloalkyl group for Ra may have two or more of the substituents described above, which may be the same or different.

Examples of the C6-C20 aromatic hydrocarbon ring group and C2-C20 heteroaromatic ring group as well as substituents thereon for Ra are the same as those exemplified for Ax.

Of these groups described above, preferred as Ra are hydrogen, C1-C20 alkyl group which may have a substituent, C2-C20 alkenyl group which may have a substituent, C2-20 alkynyl group which may have a substituent, C5-C20 cycloalkyl group which may have a substituent, C6-C18 aromatic hydrocarbon ring group which may have a substituent, and C5-C18 heteroaromatic ring group which may have a substituent, more preferably hydrogen, C1-C10 alkyl group which may have a substituent, C2-C10 alkenyl group which may have a substituent, C2-C10 alkynyl group which may have a substituent, C5-C10 cycloalkyl group which may have a substituent, and C6-C12 aromatic hydrocarbon ring group.

In Formula (III) above, $Z^{11}$ and $Z^{12}$ are each independently —CO—O—, —O—CO—, —NR$^{31}$—CO— or —CO—NR$^{32}$—, where R$^{31}$ and R$^{32}$ are each independently hydrogen or C1-C6 alkyl group. In particular, $Z^{11}$ is preferably —CO—O—, and $Z^{12}$ is preferably —O—CO—.

$A^{11}$ and $A^{12}$ are each independently alicyclic group which may have a substituent or aromatic group which may have a substituent. In particular, $A^{11}$ and $A^{12}$ are each independently preferably alicyclic group which may have a substituent.

The alicyclic group which may have a substituent is a substituted or unsubstituted divalent alicyclic group, where the divalent alicyclic group is a divalent aliphatic group having cyclic structure and typically having 5 to 20 carbon atoms.

Specific examples of the divalent alicyclic group for $A^{11}$ and $A^{12}$ are the same as those exemplified for $A^1$ in Formula (I) above.

The aromatic group which may have a substituent is a substituted or unsubstituted divalent aromatic group, where the divalent aromatic group is a divalent aromatic group having aromatic ring structure and typically having 2 to 20 carbon atoms.

Specific examples of the divalent aromatic group for $A^{11}$ and $A^{12}$ are the same as those exemplified for $A^1$ in Formula (I) above.

Examples of the substituents on the divalent alicyclic group and divalent aromatic group for $A^{11}$ and $A^{12}$ are the same as those exemplified for the divalent alicyclic group and divalent aromatic group for $A^1$ in Formula (I) above.

When h and/or i is 1, $L^{11}$ and $L^{12}$ are each independently single bond, —O—, —CO—, —CO—O—, —O—CO—, —$NR^{21}$—CO—, —CO—$NR^{22}$—, —O—CO—O—, —$NR^{23}$—CO—O—, —O—CO—$NR^{24}$— or —$NR^{25}$—CO—$NR^{26}$—, where $R^{21}$ to $R^{26}$ are each independently hydrogen or C1-C6 alkyl group. In particular, $L^{11}$ and $L^{12}$ are each independently preferably —O—, —CO—O— or —O—CO—.

Examples of the C1-C6 alkyl group for $R^{21}$ to $R^{26}$ include methyl group, ethyl group, propyl group, and isopropyl group.

When h and/or i is 1, $B^{11}$ and $B^{12}$ are each independently alicyclic group which may have a substituent or aromatic group which may have a substituent. In particular, $B^{11}$ and $B^{12}$ are each independently preferably aromatic group which may have a substituent.

The alicyclic group which may have a substituent is a substituted or unsubstituted divalent alicyclic group, where the divalent alicyclic group is a divalent aliphatic group having cyclic structure and typically having 5 to 20 carbon atoms.

Specific examples of the divalent alicyclic group for $B^{11}$ and $B^{12}$ are the same as those exemplified for $A^1$ in Formula (I) above.

The aromatic group which may have a substituent is a substituted or unsubstituted divalent aromatic group, where the divalent aromatic group is a divalent aromatic group having aromatic ring structure and typically having 2 to 20 carbon atoms.

Specific examples of the divalent aromatic group for $B^{11}$ and $B^{12}$ are the same as those exemplified for $A^1$ in Formula (I) above.

Examples of the substituents on the divalent alicyclic group and divalent aromatic group for $B^{11}$ and $B^{12}$ are the same as those exemplified for the divalent alicyclic group and divalent aromatic group for $A^1$ in Formula (I) above.

$Y^{11}$ and $Y^{12}$ are each independently single bond, —O—, —CO—, —CO—O—, —O—CO—, —$NR^{21}$—CO—, —CO—$NR^{22}$—, —O—CO—O—, —$NR^{23}$—CO—O—, —O—CO—$NR^{24}$— or —$NR^{25}$—CO—$NR^{26}$—, where $R^{21}$ to $R^{26}$ are each independently hydrogen or C1-C6 alkyl group. In particular, $Y^{11}$ and $Y^{12}$ are each independently preferably —O—, —CO—O— or —O—CO—.

Examples of the C1-C6 alkyl group for $R^{21}$ to $R^{26}$ include methyl group, ethyl group, propyl group, and isopropyl group.

$R^4$ to $R^7$ are each independently hydrogen, methyl group or chlorine, preferably hydrogen or methyl group. All of $R^4$ to $R^7$ are preferably the same, and all of $R^4$ to $R^7$ are more preferably hydrogen.

From the perspective of obtaining optical film etc. which exhibit superior reverse wavelength dispersion, polymerizable compound (III) preferably has generally symmetric structure about $Ar^1$-$D^1$. More specifically, it is preferred that in polymerizable compound (III), $R^4$, g and h are the same as $R^7$, j and i, respectively, and that —$Y^{11}$—$[B^{11}$-$L^{11}]_h$-$A^{11}$-$Z^{11}$—(*) and (*)—$Z^{12}$-$A^{12}$-$[L^{12}$-$B^{12}]_i$—$Y^{12}$— are symmetrical to each other about (*), a side for binding with $Ar^1$.

By the phrase "symmetrical to each other about (*)" is meant to have such pairs of structures as —CO—O—(*) and (*)—O—CO—, —O—(*) and (*)—O—, or —O—CO—(*) and (*)—CO—O—.

Polymerizable compound (III) described above can be synthesized by combining the synthesis reactions known in the art. Specifically, polymerizable compound (III) can be synthesized with reference to methods described in various literatures, e.g., March's Advanced Organic Chemistry (Wiley), and S. R. Sandler and W. Karo "Organic Functional Group Preparations."

A preferred example of polymerizable compound (III) where h and i are 1 includes, but not limited to, a compound having the following Formula (Va) (hereinafter occasionally referred to as "polymerizable compound (Va)"):

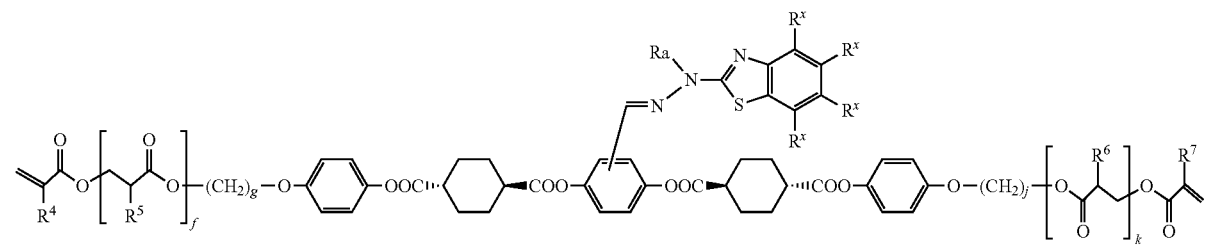

(Va)

where $R^4$ to $R^7$, Ra, $R^x$, f, g, j and k are as defined above.

Any method can be used for the production of polymerizable compound (Va). One exemplary method involves sequentially reacting 2,5-dihydroxybenzaldehyde having the following Formula (7) with a compound having the following Formula (b) (hereinafter referred to as "compound (b)") and a compound having the following Formula (c) (hereinafter referred to as "compound (c)") to give a compound having the following Formula (9) (hereinafter referred to as "compound (9)"), and reacting the resulting compound (9) with a hydrazine compound having the following Formula (10) to give polymerizable compound (Va).
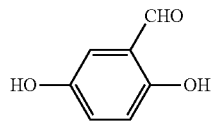
(7)
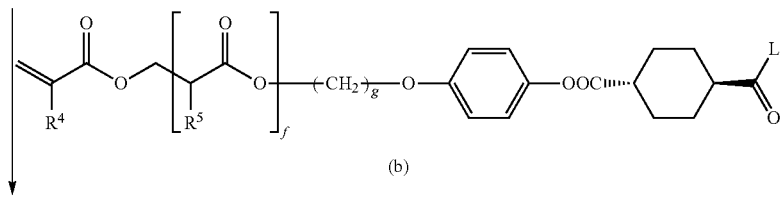
(b)
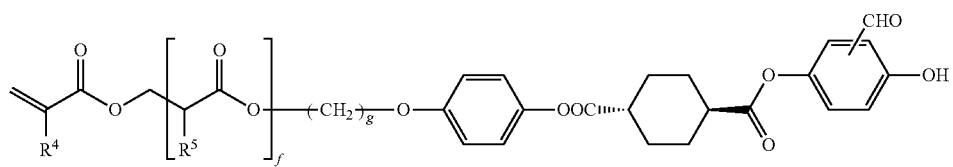
(8)
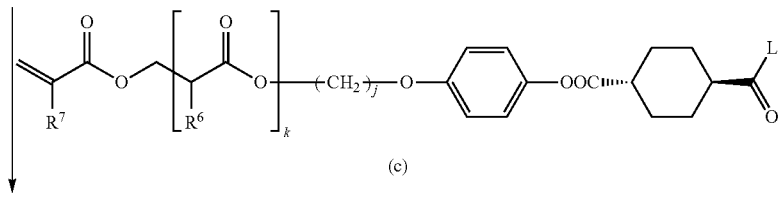
(c)
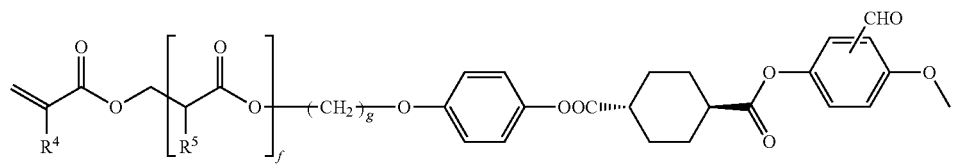
(9)
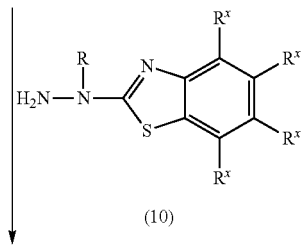
(10)

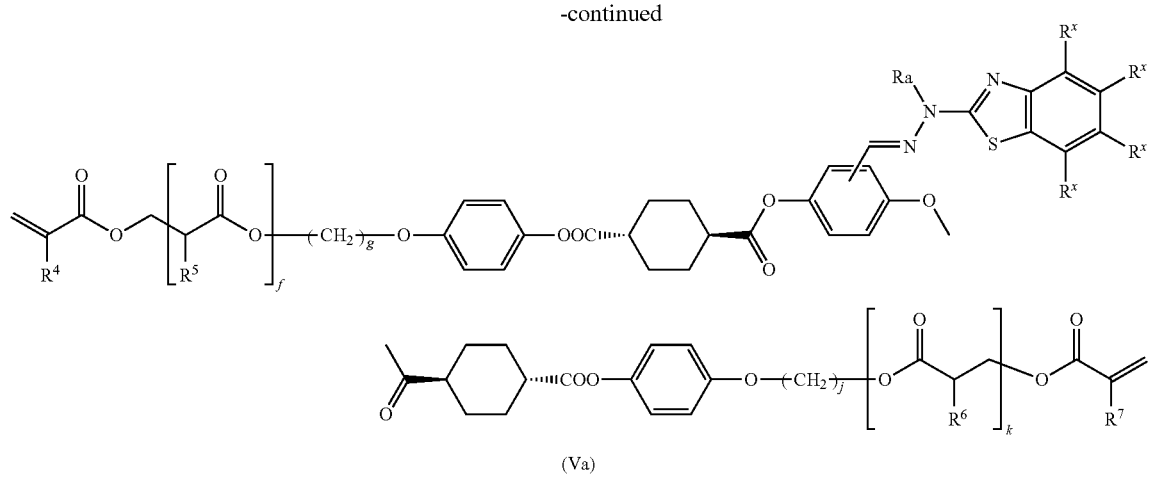

(Va)

where $R^4$ to $R^7$, f, g, j, k, Ra and $R^x$ are as defined above, and L represent leaving group as in Formula (2) above.

Compounds (b) and (c) (hereinafter occasionally collectively referred to as "compound (b) etc.") where L is halogen (i.e., acid halide) can be obtained by reacting compound (IIIa) with a halogenating agent such as thionyl chloride in the presence of an activator.

Examples of activators used include N,N-dimethylformamide, and quaternary ammonium salts such as benzyltriethylammonium chloride and benzyltrimethylammonium chloride.

The activator is used at an amount of typically 0.1 to 3 moles per 1 mole of compound (b) etc.

Compound (b) etc. where L is alkyl(aryl)sulfonyloxy group such as methanesulfonyloxy or p-toluenesulfonyloxy group (i.e., mixed-anhydride) can be obtained by reacting compound (IIIa) with a sulfonyl chloride compound having the formula $R^dSO_2Cl$ (where $R^d$ is as defined in Formula (6) above) in suitable solvent in the presence of a base.

The base can be triethylamine, N,N-diisopropylethylamine, 4-(dimethylamino)pyridine or the like.

The suitable solvent can be any of the solvents exemplified above as being usable for the production of compound (Ia) and halogen solvents such as methylene chloride and chloroform, with ether solvents being preferred.

Examples of solvents used for the reaction between 2,5-dihydroxybenzaldehyde having Formula (7) with compound (b) etc. include chlorine solvents such as chloroform and methylene chloride; amide solvents such as N-methylpyrrolidone, N,N-dimethylformamide, N,N-dimethylacetamide, and hexamethylphosphoric triamide; ether solvents such as 1,4-dioxane, cyclopentyl methyl ether, tetrahydrofuran, tetrahydropyran, and 1,3-dioxofuran; sulfur-containing solvents such as dimethyl sulfoxide and sulfolane; aromatic hydrocarbon solvents such as benzene, toluene, and xylene; aliphatic hydrocarbon solvents such as n-pentane, n-hexane, n-octane, cyclopentane, and cyclohexane; and mixture solvents of two or more of the foregoing.

Any amount of solvent can be used and the amount can be determined as appropriate in light of, for example, the types of compounds used or reaction scale. Typically, 1 to 50 g of solvent is used per 1 g of compound (b) etc.

The target polymerizable compound (Va) can be produced highly selectively in high yield by reacting compound (9) with hydrazine compound (10) at a mole ratio (compound (9):hydrazine compound (10)) of 1:2 to 2:1, preferably 1:1.5 to 1.5 to 1.

This reaction can be performed with the addition of an acid catalyst such as an organic acid (e.g., (±)-10-camphorsulfonic acid or p-toluenesulfonic acid) or an inorganic acid (e.g., hydrochloric acid or sulfuric acid). The addition of acid catalyst shortens the reaction time and may increase yield. The acid catalyst is added at an amount of typically 0.001 to 1 mole per 1 mole of compound (9). The acid catalyst may be added directly as it is or as a solution in suitable solvent.

Any solvent can be for the reaction between compound (9) and hydrazine compound (10) as long it is inert to the reaction. Examples thereof include alcohol solvents such as methyl alcohol, ethyl alcohol, n-propyl alcohol, isopropyl alcohol, n-butyl alcohol, and isobutyl alcohol; ether solvents such as diethylether, tetrahydrofuran, 1,4-dioxane, and cyclopentyl methyl ether; ester solvents such as ethyl acetate and propyl acetate; aromatic hydrocarbon solvents such as benzene, toluene, and xylene; aliphatic hydrocarbon solvents such as n-pentane, n-hexane, and n-heptane; amide solvents such as N,N-dimethylformamide and N-methylpyrrolidone; sulfur-containing solvents such as dimethyl sulfoxide and sulfolane; chlorine solvents such as chloroform and methylene chloride; and mixture solvents of two or more of the foregoing.

Of these solvents, preferred are alcohol solvents, chlorine solvents, ether solvents, and mixture solvents of two or more of the foregoing.

Any amount of solvent can be used and the amount can be determined as appropriate in light of, for example, the types of compounds used or reaction scale. Typically, 1 to 100 g of solvent is used per 1 g of hydrazine compound (10).

The reaction proceeds smoothly in a temperature range from −10° C. up to the boiling point of solvent used. Reaction time is several minutes to several hours although it depends on the reaction scale.

(4) Mixture Containing Polymerizable Compounds

The disclosed mixture is a mixture containing polymerizable compound (III) and a polymerizable compound having the following Formula (IV) (polymerizable compound (IV)) and can be used for the production of a polymerizable liquid crystal composition and a polymer which are described later.

From the perspective of enhancing reverse wavelength dispersion of the resulting optical film etc. while broadening the process margin upon formation of the optical film etc. using the mixture or polymerizable liquid crystal composition prepared using the mixture, the mass ratio of polymerizable compound (III) to polymerizable compound (IV) (polymerizable compound (III):polymerizable compound (IV)) in the mixture is preferably 1:1,000 to 20:100, more preferably 1:100 to 20:100.

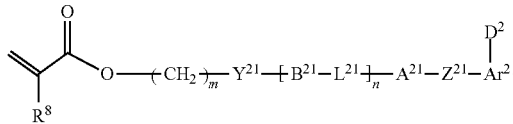 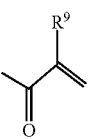 (IV)

The use of the mixture of polymerizable compound (III) and polymerizable compound (IV) makes it possible to obtain a polymerizable liquid crystal composition which can retain liquid crystal phase more stably over long periods of time, has a wide process margin, has a low melting point suitable for practical use, has superior solubility in common solvents, and allows for low-cost manufacture of optical film etc. which are capable of uniform polarized light conversion over a wide wavelength range.

A possible but still uncertain reason for this is that polymerizable compound (III) has a moiety represented by —$(CH_2CHR^5COO)_j$— and/or a moiety represented by —$(OCOCHR^6CH_2)_k$— and hence the use of the mixture of polymerizable compounds (III) and (IV) results in the formation of a liquid crystal layer that easily turns into liquid crystal phase at lower temperatures (i.e., easily becomes supercooling state at room temperature) compared to cases where only polymerizable compound (IV) is used while ensuring optical characteristics (especially reverse wavelength dispersion), so that optical film etc. having a polymer as the constituent material can be obtained.

In Formula (IV), m and q are each independently an integer of 1 to 20, preferably an integer of 2 to 12, more preferably an integer of 4 to 8, and n and p are each independently 0 or 1, preferably 1.

$Ar^2$ is divalent aromatic hydrocarbon ring group having $D^2$ as a substituent or divalent heteroaromatic ring group having $D^2$ as a substituent. $D^2$ is C1-C20 organic group having at least one aromatic ring selected from the group consisting of an aromatic hydrocarbon ring and a heteroaromatic ring.

The divalent aromatic hydrocarbon ring group having $D^2$ as a substituent or divalent heteroaromatic ring group having $D^2$ as a substituent refers to a group obtained by removing, from the ring moiety of the aromatic hydrocarbon ring or heteroaromatic ring to which $D^2$ is bound, two hydrogens attached to carbon atoms other than the carbon atom to which $D^2$ is bound.

Examples of the divalent aromatic hydrocarbon ring group for $Ar^2$ are the same as those exemplified for $Ar^1$ of polymerizable compound (III).

Examples of the divalent heteroaromatic ring group for $Ar^2$ are the same as those exemplified for $Ar^1$ of polymerizable compound (III).

The divalent aromatic hydrocarbon ring group and divalent heteroaromatic ring group for $Ar^2$ may have at least one substituent in addition to $D^2$, as with $Ar^1$ of polymerizable compound (III). Examples of the substituents on the divalent aromatic hydrocarbon ring group and divalent heteroaromatic ring group for $Ar^2$ are the same as those exemplified for the divalent aromatic hydrocarbon ring group and divalent heteroaromatic ring group for $Ar^1$.

Examples of the C1-C20 organic group having at least one aromatic group selected from the group consisting of an aromatic hydrocarbon ring and a heteroaromatic ring for $D^2$ are the same as those exemplified for $D^1$ of polymerizable compound (III).

Examples of combinations of $Ar^2$ and $D^2$ ($Ar^2$-$D^2$) include phenylene group substituted with a group having the formula —$R^fC(=N-NR^gR^h)$, benzothiazole-4,7-diyl group substituted with 1-benzofuran-2-yl group, benzothiazole-4,7-diyl group substituted with 5-(2-butyl)-1-benzofuran-2-yl group, benzothiazole-4,7-diyl group substituted with 4,6-dimethyl-1-benzofuran-2-yl group, benzothiazole-4,7-diyl group substituted with 6-methyl-1-benzofuran-2-yl group, benzothiazole-4,7-diyl group substituted with 4,6,7-trimethyl-1-benzofuran-2-yl group, benzothiazole-4,7-diyl group substituted with 4,5,6-trimethyl-1-benzofuran-2-yl group, benzothiazole-4,7-diyl group substituted with 5-methyl-1-benzofuran-2-yl group, benzothiazole-4,7-diyl group substituted with 5-propyl-1-benzofuran-2-yl group, benzothiazole-4,7-diyl group substituted with 7-propyl-1-benzofuran-2-yl group, benzothiazole-4,7-diyl group substituted with 5-fluoro-1-benzofuran-2-yl group, benzothiazole-4,7-diyl group substituted with phenyl group, benzothiazole-4,7-diyl group substituted with 4-fluorophenyl group, benzothiazole-4,7-diyl group substituted with 4-nitrophenyl group, benzothiazole-4,7-diyl group substituted with 4-trifluoromethylphenyl group, benzothiazole-4,7-diyl group substituted with 4-cyanophenyl group, benzothiazole-4,7-diyl group substituted with 4-methanesulfonylphenyl group, benzothiazole-4,7-diyl group substituted with thiophene-2-yl group, benzothiazole-4,7-diyl group substituted with thiophene-3-yl group, benzothiazole-4,7-diyl group substituted with 5-methylthiophene-2-yl group, benzothiazole-4,7-diyl group substituted with 5-chlorothiophene-2-yl group, benzothiazole-4,7-diyl group substituted with thieno[3,2-b]thiophene-2-yl group, benzothiazole-4,7-diyl group substituted with 2-benzothiazolyl group, benzothiazole-4,7-diyl group substituted with 4-biphenyl group, benzothiazole-4,7-diyl group substituted with 4-propylbiphenyl group, benzothiazole-4,7-diyl group substituted with 4-thiazolyl group, benzothiazole-4,7-diyl group substituted with 1-phenylethylene-2-yl group, benzothiazole-4,7-diyl group substituted with 4-pyridyl group, benzothiazole-4,7-diyl group substituted with 2-furyl group, benzothiazole-4,7-diyl group substituted with naphtho[1,2-b]furan-2-yl group, 1H-isoindole-1,3(2H)-dione-4,7-diyl group substituted with 5-methoxy-2-benzothiazolyl group, 1H-isoindole-1,3(2H)-dione-4,7-diyl group substituted with phenyl group, 1H-isoindole-1,3(2H)-dione-4,7-diyl group substituted with 4-nitrophenyl group, and 1H-isoindole-1,3(2H)-dione-4,7-diyl group substituted with 2-thiazolyl group. $R^f$, $R^g$ and $R^h$ in the formula —$R^fC(=N-NR^gR^h)$ are as defined above.

Of these combinations, $Ar^2$-$D^2$ is preferably a group having the following Formula (VII):

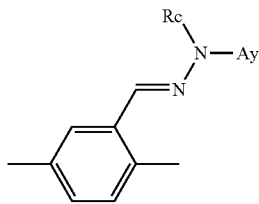

(VII)

where Ay represents C2-C20 organic group having at least one aromatic ring selected from the group consisting of an aromatic hydrocarbon ring and a heteroaromatic ring, and Rc represents hydrogen or C1-C20 organic group which may have a substituent.

Examples of the C2-C20 organic group having at least one aromatic ring selected from the group consisting of an aromatic hydrocarbon ring and a heteroaromatic ring for Ay are the same as those exemplified for Ax in Formula (V).

In particular, Ay is preferably a group having the following Formula (VI) as with Ax of Formula (V), more preferably a group having Formula (VI) where all of $R^x$ are hydrogen.

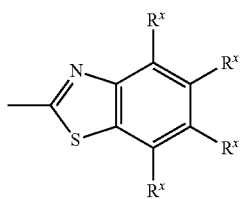

(VI)

where $R^x$ are as defined above.

Examples of the C1-C20 organic group which may have a substituent for Rc are the same as those exemplified for Ra in Formula (V).

In Formula (IV) above, $Z^{21}$ and $Z^{22}$ are each independently —CO—O—, —O—CO—, —$NR^{31}$—CO— or —CO—$NR^{32}$—, where $R^{31}$ and $R^{32}$ are each independently hydrogen or C1-C6 alkyl group. In particular, $Z^{21}$ is preferably —CO—O—, and $Z^{22}$ is preferably —O—CO—.

$A^{21}$ and $A^{22}$ are each independently alicyclic group which may have a substituent, or aromatic group which may have a substituent. In particular, $A^{21}$ and $A^{22}$ are each independently preferably alicyclic group which may have a substituent.

Examples of the alicyclic and aromatic groups which may have a substituent for $A^{21}$ and $A^{22}$ are the same as those exemplified for $A^{11}$ and $A^{11}$ of polymerizable compound (III).

When n and/or p is 1, $L^{21}$ and $L^{22}$ are each independently single bond, —O—, —CO—, —CO—O—, —O—CO—, —$NR^{21}$—CO—, —CO—$NR^{22}$—, —O—CO—O—, —$NR^{23}$—CO—O—, —O—CO—$NR^{24}$— or —$NR^{25}$—CO—$NR^{26}$—, where $R^{21}$ to $R^{26}$ are each independently hydrogen or C1-C6 alkyl group. In particular, $L^{21}$ and $L^{22}$ are each independently preferably —O—, —CO—O— or —O—CO—.

Examples of the C1-C6 alkyl group for $R^{21}$ to $R^{26}$ include methyl group, ethyl group, propyl group, and isopropyl group.

When n and/or p is 1, $B^{21}$ and $B^{22}$ are each independently alicyclic group which may have a substituent, or aromatic group which may have a substituent. In particular, $B^{21}$ and $B^{22}$ are each independently preferably aromatic group which may have a substituent.

Examples of the alicyclic and aromatic groups which may have a substituent for $B^{21}$ and $B^{22}$ are the same as those exemplified for $B^{11}$ and $B^{11}$ of polymerizable compound (III).

$Y^{21}$ and $Y^{22}$ are each independently single bond, —O—, —CO—, —CO—O—, —O—CO—, —$NR^{21}$—CO—, —CO—$NR^{22}$—, —O—CO—O—, —$NR^{23}$—CO—O—, —O—CO—$NR^{24}$— or —$NR^{25}$—CO—$NR^{26}$—, where $R^{21}$ to $R^{26}$ are each independently hydrogen or C1-C6 alkyl group. In particular, $Y^{21}$ and $Y^{22}$ are each independently preferably —O—, —CO—O— or —O—CO—.

Examples of the C1-C6 alkyl group for $R^{21}$ to $R^{26}$ include methyl group, ethyl group, propyl group, and isopropyl group.

$R^8$ and $R^9$ are each independently hydrogen, methyl group or chlorine, preferably hydrogen or methyl group. $R^8$ and $R^9$ are preferably the same, and both of $R^8$ and $R^9$ are more preferably hydrogen.

From the perspective of obtaining optical film etc. which exhibit superior reverse wavelength dispersion, polymerizable compound (IV) preferably has symmetric structure about $Ar^2$-$D^2$. More specifically, it is preferred that in polymerizable compound (IV), $R^8$, m and n are the same as $R^9$, q and p, respectively, and that —$Y^{21}$—$[B^{21}$-$L^{21}]_n$-$A^{21}$-$Z^{21}$—(*) and (*)—$Z^{22}$-$A^{22}$-$[L^{22}$-$B^{22}]_p$—$Y^{22}$— are symmetrical to each other about (*), a side for binding with $Ar^2$.

By the phrase "symmetrical to each other about (*)" is meant to have such pairs of structures as —CO—O—(*) and (*)—O—CO—, —O—(*) and (*)—O—, or —O—CO—(*) and (*)—CO—O—.

Polymerizable compound (IV) described above can be synthesized by combining synthesis reactions known in the art. Specifically, polymerizable compound (IV) can be synthesized with reference to methods described in various literatures, e.g., March's Advanced Organic Chemistry (Wiley), and S. R. Sandler and W. Karo "Organic Functional Group Preparations."

From the perspective of enhancing reverse wavelength dispersion of optical film etc., in the disclosed mixture, $Ar^1$, $Z^{11}$, $Z^{12}$, $A^{11}$, $A^{12}$, $B^{11}$, $B^{12}$, $Y^{11}$, $Y^{12}$, $L^{11}$, $L^{12}$, $R^4$, $R^7$, g, j, h and i of polymerizable compound (III) are preferably the same as $Ar^2$, $Z^{21}$, $Z^{22}$, $A^{21}$, $A^{22}$, $B^{21}$, $B^{22}$, $Y^{21}$, $Y^{22}$, $L^{21}$, $L^{22}$, $R^8$, $R^9$, m, q, n and p of polymerizable compound (IV), respectively. $D^1$ and $D^2$ may be the same or different.

Specifically, the structure of polymerizable compound (III) exclusive of $D^1$ is preferably the same as the structure of polymerizable compound (IV) exclusive of $D^2$ except for the presence of —($CH_2CHR^5COO)_f$— between $CH_2CR^4COO$— and —$(CH_2)_g$— and the presence of —($OCOCHR^6CH_2)_k$— between —$OCOCR^7CH_2$ and —$(CH_2)_j$—.

The mixture can be prepared for example by mixing polymerizable compounds (III) and (IV) at desired ratios.

The mixture can also be obtained by any method, e.g., by reacting the mixture containing compounds (I) and (II) with a compound having the following formula followed by conversion of $L^5$ into $D^1$:

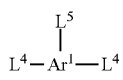

where L⁴ represent a group which may form —CO—O—, —O—CO—, —NR³¹—CO— or —CO—NR³²— by reaction with FG¹ of compound (I) or FG² of compound (II) with the proviso that $R^{31}$ and $R^{32}$ are each independently hydrogen or C1-C6 alkyl group; L⁵ represents a group which can be converted into D¹; and Ar¹ is as defined in Formula (III).

A preferred example of polymerizable compound (IV) where n and p are 1 includes, but not limited to, a compound having the following Formula (VIa) (hereinafter occasionally referred to as "compound (VIa)"):

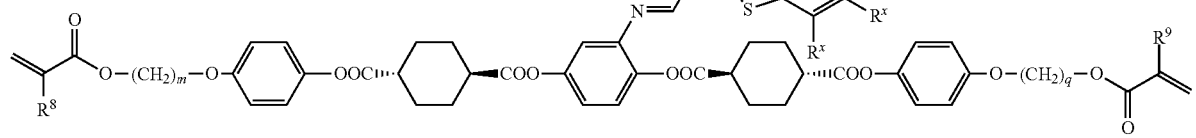

(VIa)

where $R^8$, $R^9$, Rc, $R^x$, m and q are as defined above, and all of $R^x$ are preferably hydrogen.

Compound (VIa) can be produced by any of the methods known in the art, e.g., by the method described in PTL 1.

The mixture containing compounds (Va) and (VIa) can be prepared for example by mixing compounds (Va) and (VIa) at desired ratios.

The mixture containing compounds (Va) and (VIa) can also be obtained for example by replacing compounds (b) and (c) by the mixture containing compounds (IIIa) and (IVa) in the above-described method of producing compound (Va).

(5) Polymerizable Liquid Crystal Composition

The disclosed polymerizable liquid crystal composition contains a mixture containing the polymerizable compounds described above (i.e., a mixture containing polymerizable compounds (III) and (IV)) and a polymerization initiator.

As will be described later, the disclosed polymerizable liquid crystal composition is useful as the raw material for the manufacture of disclosed polymers, optical films and optically anisotropic product. The disclosed polymerizable liquid crystal composition can retain liquid crystal phase more stably over long periods of time, has a wide process margin, has a low melting point suitable for practical use, has superior solubility in common solvents, and allows for low-cost manufacture of optical film etc. which are capable of uniform polarized light conversion over a wide wavelength range.

The polymerization initiator is blended in the polymerizable liquid crystal composition for more efficient polymerization reaction of the polymerizable compounds contained in the composition.

Examples of polymerization initiators used include radical polymerization initiators, anion polymerization initiators, and cation polymerization initiators.

For radical polymerization initiators, both of thermal radical generators (compounds that on heating generate active species that may initiate polymerization of polymerizable compounds) and photo-radical generators (compounds that on exposure to exposure light such as visible ray, ultraviolet ray (e.g., i line), far-ultraviolet ray, electron ray or X ray generate active species that may initiate polymerization of polymerizable compounds) can be used, with photo-radical generators being suitable.

Examples of the photo-radical generators include acetophenone compounds, biimidazole compounds, triazine compounds, O-acyloxime compounds, onium salt compounds, benzoin compounds, benzophenone compounds, α-diketone compounds, polynuclear quinone compounds, xanthone compounds, diazo compounds, and imidesulfonate compounds. These compounds are components that on exposure to light generate one or both of active radicals and active acid. These photo-radical generators can be used alone or in combination.

Specific examples of the acetophenone compounds include 2-hydroxy-2-methyl-1-phenylpropane-1-one, 2-methyl-1-[4-(methylthio)phenyl]-2-morpholinopropane-1-one, 2-benzyl-2-dimethylamino-1-(4-morpholinophenyl) butane-1-one, 1-hydroxycyclohexyl phenyl ketone, 2,2-dimethoxy-1,2-diphenylethane-1-one, 1,2-octanedione, and 2-benzyl-2-dimethylamino-4'-morpholinobutyrophenone.

Specific examples of the biimidazole compounds include 2,2'-bis(2-chlorophenyl)-4,4',5,5'-tetrakis(4-ethoxycarbonylphenyl)-1,2'-biimidazole, 2,2'-bis(2-bromophenyl)-4,4', 5,5'-tetrakis(4-ethoxycarbonylphenyl)-1,2'-biimidazole, 2,2'-bis(2-chlorophenyl)-4,4',5,5'-tetraphenyl-1,2'-biimidazole, 2,2'-bis(2,4-dichlorophenyl)-4,4',5,5'-tetraphenyl-1,2'-biimidazole, 2,2'-bis(2,4,6-trichlorophenyl)-4,4',5,5'-tetraphenyl-1,2'-biimidazole, 2,2'-bis(2-bromophenyl)-4,4',5,5'-tetraphenyl-1,2'-biimidazole, 2,2'-bis(2,4-dibromophenyl)-4,4',5,5'-tetraphenyl-1,2'-biimidazole, and 2,2'-bis(2,4,6-tribromophenyl)-4,4',5,5'-tetraphenyl-1,2'-biimidazole.

When biimidazole compounds are used as photopolymerization initiators (photo-radical generators) in the present disclosure, it is preferable to use hydrogen donors in combination for further improvement in sensitivity.

By "hydrogen donor" is meant a compound that can donate hydrogen to a radical generated on exposure to light from a biimidazole compound. Preferred hydrogen donors are mercaptan compounds and amine compounds defined below.

Examples of the mercaptan compounds include 2-mercaptobenzothiazole, 2-mercaptobenzoxazole, 2-mercaptobenzimidazole, 2,5-dimercapto-1,3,4-thiadiazole, and 2-mercapto-2,5-dimethylaminopyridine. Examples of amine compounds include 4,4'-bis(dimethylamino)benzophenone, 4,4'-bis(diethylamino)benzophenone, 4-diethylaminoacetophenone, 4-dimethylaminopropiophenone, ethyl-4-dimethylaminobenzoate, 4-dimethylamino benzoic acid, and 4-dimethylaminobenzonitrile.

Examples of the triazine compounds include triazine compounds having a halomethyl group, such as 2,4,6-tris (trichloromethyl)-s-triazine, 2-methyl-4,6-bis(trichloromethyl)-s-triazine, 2-[2-(5-methylfuran-2-yl)ethenyl]-4,6-bis(trichloromethyl)-s-triazine, 2-[2-(furan-2-yl)ethenyl]-4,6-bis(trichloromethyl)-s-triazine, 2-[2-(4-diethylamino-2-methylphenyl)ethenyl]-4,6-bis(trichloromethyl)-s-triazine, 2-[2-(3,4-dimethoxyphenyl)ethenyl]-4,6-bis(trichloromethyl)-s-triazine, 2-(4-methoxyphenyl)-4,6-bis(trichloromethyl)-s-triazine, 2-(4-ethoxystyryl)-4,6-bis(trichloromethyl)-s-triazine, and 2-(4-n-butoxyphenyl)-4,6-bis(trichloromethyl)-s-triazine.

Specific examples of the O-acyloxime compounds include 1-[4-(phenylthio)phenyl]-heptane-1,2-dione2-(O-benzoyloxime), 1-[4-(phenylthio)phenyl]-octane-1,2-dione2-(O-benzoyloxime), 1-[4-(benzoyl)phenyl]-octane-1,2-dione2-(O-benzoyloxime), 1-[9-ethyl-6-(2-methylbenzoyl)-9H-carbozole-3-yl]-ethanone 1-(O-acetyloxime), 1-[9-ethyl-6-(3-methylbenzoyl)-9H-carbozole-3-yl]-ethanone1-(O-acetyloxime), 1-(9-ethyl-6-benzoyl-9H-carbozole-3-yl)-ethanone1-(O-acetyloxime), ethanone-1-[9-ethyl-6-(2-methyl-4-tetrahydrofuranylbenzoyl)-9H-carbozole-3-yl]-1-(O-acetyloxime), ethanone-1-[9-ethyl-6-(2-methyl-4-tetrahydropyranylbenzoyl)-9H-carbozole-3-yl]-1-(O-acetyloxime), ethanone-1-[9-ethyl-6-(2-methyl-5-tetrahydrofuranylbenzoyl)-9H-carbozole-3-yl]-1-(O-acetyloxime), ethanone-1-[9-ethyl-6-(2-methyl-5-tetrahydropyranylbenzoyl)-9H-carbozole-3-yl]-1-(O-acetyloxime), ethanone-1-[9-ethyl-6-{2-methyl-4-(2,2-dimethyl-1,3-dioxolanyl)benzoyl}-9H-carbozole-3-yl]-1-(O-acetyloxime), ethanone-1-[9-ethyl-6-(2-methyl-4-tetrahydrofuranylmethoxybenzoyl)-9H-carbozole-3-yl]-1-(O-acetyloxime), ethanone-1-[9-ethyl-6-(2-methyl-4-tetrahydropyranylmethoxybenzoyl)-9H-carbozole-3-yl]-1-(O-acetyloxime), ethanone-1-[9-ethyl-6-(2-methyl-5-tetrahydrofuranylmethoxybenzoyl)-9H-carbozole-3-yl]-1-(O-acetyloxime), ethanone-1-[9-ethyl-6-(2-methylbenzoyl)-9H-carbozole-3-yl]-1-(O-acetyloxime), ethanone-1-[9-ethyl-6-(2-methyl-5-tetrahydropyranylmethoxybenzoyl)-9H-carbozole-3-yl]-1-(O-acetyloxime), and ethanone-1-[9-ethyl-6-{2-methyl-4-(2,2-dimethyl-1,3-dioxolanyl)methoxybenzoyl}-9H-carbozole-3-yl]-1-(O-acetyloxime).

Commercially available photo-radical generators can be used directly. Specific examples include Irgacure 907, Irgacure 184, Irgacure 369, Irgacure 651, Irgacure 819, Irgacure 907 and Irgacure OXE02 (BASF), and ADEKA OPTOMER N1919 (ADEKA Corporation).

Examples of the anion polymerization initiators include alkyllithium compounds; monolithium or monosodium salts of biphenyl, naphthalene, pyrene and the like; and polyfunctional initiators such as dilithium salts and trilithium salts.

Examples of the cation polymerization initiators include protonic acids such as sulfuric acid, phosphoric acid, perchloric acid, and trifluoromethanesulfonic acid; Lewis acids like boron trifluoride, aluminum chloride, titanium tetrachloride, and tin tetrachloride; and aromatic onium salts or combinations of onium salts with reducing agents.

These polymerization initiators can be used alone or in combination.

In the disclosed polymerizable liquid crystal composition, the polymerization initiator is blended at an amount of typically 0.1 to 30 parts by mass, preferably 0.5 to 10 parts by mass, per 100 parts by mass of the above-described mixture of polymerizable compounds.

The disclosed polymerizable liquid crystal composition is preferably blended with surfactants for adjustment of surface tension. Any surfactant can be used, but nonionic surfactants are generally preferred. Commercially available nonionic surfactants will suffice, e.g., nonionic surfactants made of oligomers with a molecular weight on the order of several thousands, such as Ftergent 208G (NEOS).

In the disclosed polymerizable liquid crystal composition, the surfactant is blended at an amount of typically 0.01 to 10 parts by mass, preferably 0.1 to 2 parts by mass, per 100 parts by mass of the total polymerizable compounds.

In addition to a mixture containing polymerizable compounds, a polymerization initiator and a surfactant, the disclosed polymerizable liquid crystal composition may further contain optional additives at amounts that do not compromise the effect of the present disclosure. Examples of the optional additives include metals, metal complexes, dyes, pigments, fluorescent materials, phosphorescent materials, leveling agents, thixotropic agents, gelling agents, polysaccharides, ultraviolet absorbers, infrared absorbers, antioxidants, ion-exchange resins, and metal oxides such as titanium oxide.

Other examples of the optional additives include other copolymerizable mononomers. Specific examples include, but not limited to, 4'-methoxyphenyl 4-(2-methacryloyloxyethyloxy)benzoate, biphenyl 4-(6-methacryloyloxyhexyloxy)benzoate, 4'-cyanobiphenyl 4-(2-acryloyloxyethyloxy)benzoate, 4'-cyanobiphenyl 4-(2-methacryloyloxyethyloxy)benzoate, 3',4'-difluorophenyl 4-(2-methacryloyloxyethyloxy)benzoate, naphthyl 4-(2-methacryloyloxyethyloxy)benzoate, 4-acryloyloxy-4'-decylbiphenyl, 4-acryloyloxy-4'-cyanobiphenyl, 4-(2-acryloyloxyethyloxy)-4'-cyanobiphenyl, 4-(2-methacryloyloxyethyloxy)-4'-methoxybiphenyl, 4-(2-methacryloyloxyethyloxy)-4'-(4''-fluorobenzyloxy)-biphenyl, 4-acryloyloxy-4'-propylcyclohexylphenyl, 4-methacryloyl-4'-butylbicyclohexyl, 4-acryloyl-4'-amyltolane, 4-acryloyl-4'-(3,4-difluorophenyl)bicyclohexyl, (4-amylphenyl) 4-(2-acryloyloxyethyl)benzoate, (4-(4'-propylcyclohexyl)phenyl) 4-(2-acryloyloxyethyl)benzoate, a commercially available product "LC-242" (BASF), and compounds disclosed in JP-A Nos. 2007-002208, 2009-173893, 2009-274984, 2010-030979, 2010-031223, 2011-006360 and 2010-24438.

These optional additives are blended at amounts of typically 0.1 to 20 parts by mass per 100 parts by mass of the total polymerizable compounds.

The disclosed polymerizable liquid crystal composition can be typically prepared by mixing and dissolving given amounts of a mixture containing polymerizable compounds, a polymerization initiator, and optional additive(s) in suitable organic solvent.

In this case, polymerizable compounds (III) and (IV) as a mixture may be added in the form of pre-mix or may be added separately.

Examples of organic solvents used include ketones such as cyclopentanone, cyclohexanone, and methyl ethyl ketone; acetates such as butyl acetate and amyl acetate; halogenated hydrocarbons such as chloroform, dichloromethane, and dichloroethane; and ethers such as 1,4-dioxane, cyclopentyl methyl ether, tetrahydrofuran, tetrahydropyran, and 1,3-dioxolane.

(6) Polymer

The disclosed polymer can be obtained by polymerizing a mixture containing the polymerizable compounds described above (i.e., a mixture containing polymerizable compounds (III) and (IV)) or the polymerizable liquid crystal composition.

By the term "polymerization" herein is meant a chemical reaction in a broad sense including a crosslinking reaction as well as a normal polymerization reaction.

The disclosed polymer typically includes the following monomer unit derived from polymerizable compound (III) (repeat unit (III)') and the following monomer unit derived from polymerizable compound (IV) (repeat unit (IV)'):

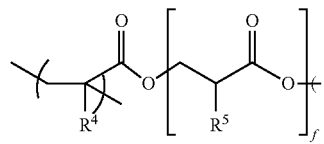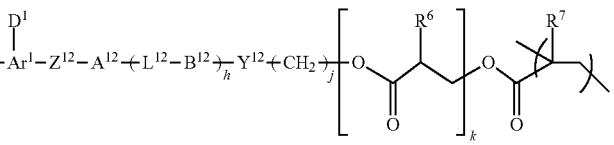

(III)' where $Ar^1$, $D^1$, $Z^{11}$, $Z^{12}$, $A^{11}$, $A^{12}$, $B^{11}$, $B^{12}$, $Y^{11}$, $Y^{12}$, $L^{11}$, $L^{12}$, $R^4$ to $R^7$, f, g, h, i, j and k are as defined in Formula (III).

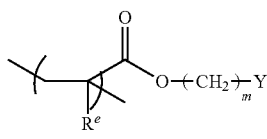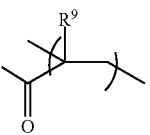

(IV)' where $Ar^2$, $D^2$, $Z^{21}$, $Z^{22}$, $A^{21}$, $A^{22}$, $B^{21}$, $B^{22}$, $Y^{21}$, $Y^{22}$, $L^{21}$, $L^{22}$, $R^8$, $R^9$, m, n, p and q are as defined in Formula (IV).

Because the disclosed polymer is prepared using the mixture containing polymerizable compounds (III) and (IV), it can be advantageously used as the constituent material for optical film etc.

Further, the disclosed polymer can be used in any shape or form according to its intended use, including film, powder or layer made of an aggregation of powder.

Specifically, films made of the polymer can be suitably used as the constituent material for optical films and optically anisotropic products described later; powders made of the polymer can be utilized for paints, anti-forgery items, security items and the like; and layers made of the polymer powder can be suitably used as the constituent material for the optically anisotropic products.

The disclosed polymer can be suitably produced for example by (α) polymerizing the mixture containing polymerizable compounds or polymerizable liquid crystal composition in suitable organic solvent, isolating the target polymer, dissolving the polymer in suitable organic solvent to prepare a solution, applying the solution on a suitable substrate to form thereon a coating film, and drying the coating film followed by optional heating, or (β) dissolving the mixture containing polymerizable compounds or polymerizable liquid crystal composition in organic solvent to prepare a solution, applying the solution on a substrate by coatings methods known in the art, removing the solvent, and effecting polymerization by heating or actinic radiation.

Any organic solvent can be used for the polymerization by method (α) above as long as it is inert. Examples of the organic solvent include aromatic hydrocarbons such as toluene, xylene, and mesitylene; ketones such as cyclohexanone, cyclopentanone, and methyl ethyl ketone; acetates such as butyl acetate and amyl acetate; halogenated hydrocarbons such as chloroform, dichloromethane, and dichloroethane; and ethers such as cyclopentyl methyl ether, tetrahydrofuran, and tetrahydropyran.

Of these organic solvents, preferred are those having a boiling point of 60° C. to 250° C., more preferably those having a boiling point of 60° C. to 150° C., from the viewpoint of handling capability.

Examples of organic solvents used to dissolve the isolated polymer in method (α) and organic solvents used in method (β) include ketone solvents such as acetone, methyl ethyl ketone, methyl isobutyl ketone, cyclopentanone, and cyclohexanone; ester solvents such as butyl acetate and amyl acetate; halogenated hydrocarbon solvents such as dichloromethane, chloroform, and dichloroethane; ether solvents such as tetrahydrofuran, tetrahydropyran, 1,2-dimethoxyethane, 1,4-dioxane, cyclopentyl methyl ether, and 1,3-dioxolane; and aprotic polar solvents such as N,N-dimethylformamide, N,N-dimethylacetamide, dimethyl sulfoxide, γ-butyrolactone, and N-methylpyrrolidone. Of these organic solvents, preferred are those having a boiling point of 60° C. to 200° C. from the viewpoint of handling capability. These solvents can be used alone or in combination.

Substrates made of any of organic or inorganic materials known in the art can be used in methods (α) and (β). Examples of the organic material include polycycloolefins such as Zeonex® and Zeonor® (Zeonex and Zeonor are registered trademarks in Japan, other countries, or both) available from Zeon Corporation, Arton® (Arton is a registered trademark in Japan, other countries, or both) available from JSR Corporation, and Apel® (Apel is a registered trademark in Japan, other countries, or both) available from by Mitsui Chemicals Inc.; polyethylene terephthalates; polycarbonates; polyimides; polyamides; polymethyl methacrylates; polystyrenes; polyvinyl chlorides; polytetrafluoroethylene, celluloses; cellulose triacetate; and polyethersulfones. Examples of the inorganic material include silicon, glass, and calcite.

The substrate may be monolayer or laminate.

The substrate is preferably made of organic material, more preferably a resin film formed of organic material.

Additional examples of the substrate include those used for the manufacture of an optically anisotropic product later described.

Coating methods known in the art can be used for applying the polymer solution on the substrate in method (α) and for applying the solution for polymerization reaction on the substrate in method (β). Specific examples of usable coating methods include curtain coating, extrusion coating, roll coating, spin coating, dip coating, bar coating, spray coating, slide coating, print coating, gravure coating, die coating, and cap coating.

Drying or solvent removal in methods (α) and (β) can be effected by natural drying, drying by heating, drying under reduced pressure, drying by heating under reduced pressure, or the like.

Polymerization of the mixture or polymerizable liquid crystal composition can be effected for example by irradiation with actinic radiation or by thermal polymerization, with irradiation with actinic radiation being preferred as heating is unnecessary so that the reaction proceeds at room temperature. Irradiation with UV or other like light is particularly preferred because the operation is simple.

Temperature during irradiation is preferably set to 30° C. or below. Irradiation intensity is typically 1 W/m$^2$ to 10 kW/m$^2$, preferably 5 W/m$^2$ to 2 kW/m$^2$.

The polymer obtained as described above can be transferred from the substrate for use, removed from the substrate for single use, or used as it is as the constituent material for optical film etc. without being removed from the substrate.

The polymer removed from the substrate can also be made into powder form by grinding methods known in the art before use.

The number-average molecular weight of the disclosed polymer is preferably 500 to 500,000, more preferably 5,000 to 300,000. When the number-average molecular weight falls within any of these ranges, the resulting film advantageously exhibits high hardness as well as high handling capability. The number-average molecular weight of the polymer can be determined by gel permeation chromatography (GPC) using monodisperse polystyrene as a standard (eluant: tetrahydrofuran).

The disclosed polymer can retain liquid crystal phase more stably over long periods of time, has a wide process margin, has a low melting point suitable for practical use, has superior solubility in common solvents, and allows for low-cost manufacture of high performance optical film etc. which are capable of uniform polarized light conversion over a wide wavelength range.

(7) Optical Film

The disclosed optical film is formed using the disclosed polymer and comprises a layer having an optical function. By "optical function" as used herein is meant simple transmittance, reflection, refraction, birefringence, or the like.

The disclosed optical film may be used in any of the following arrangements: (1) "alignment substrate/(alignment film)/optical film" where the optical film remains formed on an alignment substrate which may have an alignment film; (2) "transparent substrate film/optical film" where the optical film has been transferred to a transparent substrate film or the like which is different from the alignment substrate; and (3) single optical film form when the optical film is self-supportive.

Usable alignment films and alignment substrates are the same as those exemplified for the optically anisotropic product described later.

The disclosed optical film can be produced by (A) applying on an alignment substrate a solution of the mixture containing polymerizable compounds or of the polymerizable liquid crystal composition, drying the resulting coating film, subjecting the film to heat treatment (for alignment of liquid crystals), and irradiation and/or heating treatment (for polymerization); or (B) applying on an alignment substrate a solution of a liquid crystal polymer obtained by polymerization of the mixture containing polymerizable compounds or liquid crystal composition, and optionally drying the resulting coated film.

The disclosed optical film can be used for optically anisotropic products, alignment films for liquid crystal display devices, color filters, low-pass filters, polarization prisms, and various optical filters.

The disclosed optical film preferably has α and β values that fall within given ranges, which can be calculated as follows based on phase differences at 449.9 nm, 548.5 nm and 650.2 nm measured with an ellipsometer. Specifically, α value is preferably 0.70 to 0.99, more preferably 0.75 to 0.90, and β value is preferably 1.00 to 1.25, more preferably 1.01 to 1.20.

$$\alpha = (\text{phase difference at 449.9 nm})/(\text{phase difference at 548.5 nm})$$

$$\beta = (\text{phase difference at 650.2 nm})/(\text{phase difference at 548.5 nm})$$

(8) Optically Anisotropic Product

The disclosed optically anisotropic product has a layer having the disclosed polymer as the constituent material.

The disclosed optically anisotropic product can be obtained for example by forming an alignment film on a substrate and forming a layer made of the disclosed polymer (liquid crystal layer) on the alignment film.

The disclosed optically anisotropic product may be obtained by directly forming a layer made of the disclosed polymer (liquid crystal layer) on a substrate or may consist only of a layer made of the disclosed polymer (liquid crystal layer).

The layer made of the disclosed polymer may be formed of a polymer film or may be an aggregate of powdery polymer.

The alignment film is formed on the surface of the substrate to regulate molecules of the polymerizable liquid crystal compounds to align in one direction in the plane.

The alignment film can be obtained for example by applying a solution containing a polymer such as polyimide, polyvinyl alcohol, polyester, polyarylate, polyamideimide, or polyetherimide (alignment film composition) on the substrate to form a film, drying the film, and rubbing the film in one direction.

The thickness of the alignment film is preferably 0.001 to 5 μm, more preferably 0.001 to 1 μm.

Any method can be used for the rubbing treatment. For example, the alignment film may be rubbed in a given direction using a roll around which a cloth or felt formed of synthetic fiber (e.g., nylon) or natural fiber (e.g., cotton) is wound. It is preferable to wash the alignment film with isopropyl alcohol or the like after completion of the rubbing treatment in order to remove fine powder (foreign substance) formed during the rubbing treatment to clean the surface of the alignment film.

Alternative to the rubbing treatment, the alignment film can be provided with a function of in-plane one-direction alignment by irradiation with polarized UV light on the surface.

Examples of substrates on which the alignment film is to be formed include glass substrates and substrates formed of synthetic resin films.

Examples of synthetic resins include thermoplastic resins such as acrylic resins, polycarbonate resins, polyethersulfone resins, polyethylene terephthlate resins, polyimide resins, polymethyl methacrylate resins, polysulfone resins, polyarylate resins, polyethylene resins, polystyrene resins, polyvinyl chloride resins, cellulose diacetate, cellulose triacetate, and alicyclic olefin polymers.

Examples of the alicyclic olefin polymers include cyclic olefin random multi-component copolymers described in JP-A No. H05-310845 and U.S. Pat. No. 5,179,171; hydrogenated polymers described in JP-A No. H05-97978 and U.S. Pat. No. 5,202,388; and thermoplastic dicyclopentadiene open-ring polymers and hydrogenated products thereof described in JP-A No. H11-124429 (WO99/20676).

In this disclosure, examples of methods of forming a liquid crystal layer made of the disclosed polymer on the alignment film are the same as those described in the above chapter for the disclosed polymer (methods (α) and (β)).

The resulting liquid crystal layer may be of any thickness and typically has a thickness of 1 to 10 μm.

The disclosed optically anisotropic product can be used as any desired product, e.g., as a phase difference film, a viewing-angle enhancing film or the like.

The disclosed optically anisotropic product preferably has α and β values that fall within given ranges, which can be calculated as follows based on phase differences at 449.9 nm, 548.5 nm and 650.2 nm measured with an ellipsometer. Specifically, α value is preferably 0.70 to 0.99, more preferably 0.75 to 0.90, and β value is preferably 1.00 to 1.25, more preferably 1.01 to 1.20.

$\alpha$=(phase difference at 449.9 nm)/(phase difference at 548.5 nm)

$\beta$=(phase difference at 650.2 nm)/(phase difference at 548.5 nm)

(9) Polarizing Plate Etc.

The disclosed polarizing plate includes the disclosed optically anisotropic product and a polarizing film.

A specific example of the disclosed polarizing plate is obtained by laminating the disclosed optically anisotropic product on a polarizing film either directly or with other layer(s) (e.g., glass plate)) disposed between the optically anisotropic product and the polarizing film.

Any method can be used for the manufacture of the polarizing film. Examples of methods of manufacturing a PVA polarizing film include a method wherein iodine ions are adsorbed onto a PVA film followed by uniaxial stretching of the PVA film; a method wherein a PVA film is uniaxially stretched followed by adsorption of iodine ions; a method wherein adsorption of iodine ions to a PVA film and uniaxial stretching are simultaneously performed; a method wherein a PVA film is dyed with dichroic dye followed by uniaxial stretching; a method wherein a PVA film is uniaxially stretched followed by dying with dichroic dye; and a method wherein dying of a PVA film with dichroic dye and uniaxial stretching are simultaneously performed. Examples of methods of manufacturing a polyene polarizing film include known methods in the art, e.g., a method wherein a PVA film is uniaxially stretched followed by heating and dehydration in the presence of a dehydration catalyst, and a method wherein a polyvinyl chloride film is uniaxially stretched followed by heating and dechlorination in the presence of a dechlorination catalyst.

In the disclosed polarizing plate, the polarizing film and disclosed optically anisotropic product may be bonded with an adhesive layer consisting of an adhesive (including tackifier). The average thickness of the adhesive layer is typically 0.01 to 30 μm, preferably 0.1 to 15 μm. The adhesive layer preferably has a tensile fracture strength of 40 MPa or less as measured in accordance with JIS K7113.

Examples of adhesives for the adhesive layer include acrylic adhesives, urethane adhesives, polyester adhesives, polyvinyl alcohol adhesives, polyolefin adhesives, modified polyolefin adhesives, polyvinyl alkyl ether adhesives, rubber adhesives, vinyl chloride-vinyl acetate adhesives, styrene-butadiene-styrene copolymer (SBS copolymer) adhesives and their hydrogenated product (SEBS copolymer) adhesives, ethylene adhesives such as ethylene-vinyl acetate copolymers and ethylene-styrene copolymers, and acrylate adhesives such as ethylene-methyl methacrylate copolymer, ethylene-methyl acrylate copolymer, ethylene-ethyl methacrylate copolymer, and ethylene-ethyl acrylate copolymer.

The disclosed polarizing plate includes the disclosed optically anisotropic product and therefore can be manufactured at low costs as well as has such superior performance as low reflected luminance and capability of polarized light conversion over a wide wavelength range.

Using the disclosed polarizing plate, it is possible to suitably manufacture flat panel display devices that include a liquid crystal panel, organic electroluminescence display devices that include an organic electroluminescence panel, and anti-reflection films.

EXAMPLES

The present disclosure will now be described in detail with reference to Examples, which however shall not be construed as limiting the scope of the present disclosure in any way.

(Synthesis Example 1) Synthesis of Compound 1

Compound 1

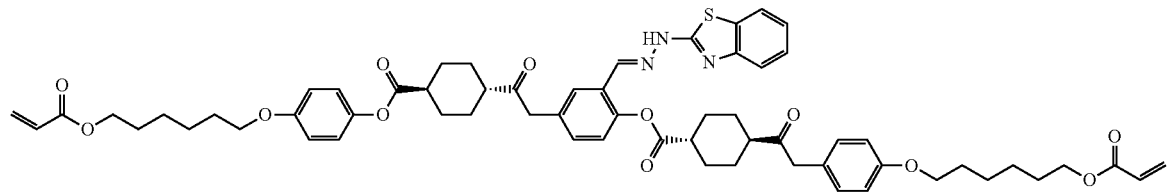

Step 1: Synthesis of Intermediate A

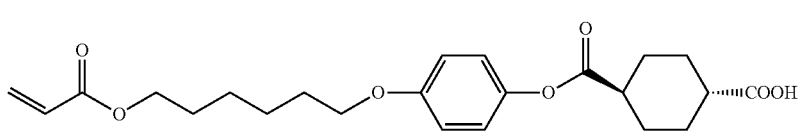

Intermediate A

A three-necked reactor equipped with a thermometer was charged with 17.98 g (104.42 mmol) of trans-1,4-cyclohexanedicarboxylic acid and 180 ml of tetrahydrofuran (THF) under a nitrogen stream. 6.58 g (57.43 mmol) of methanesulfonyl chloride was added, and the reactor was immersed in a water bath to adjust the reaction solution temperature to 20° C. 6.34 g (62.65 mmol) of triethylamine was added dropwise over 10 minutes while retaining the reaction solution temperature to 20° C. to 30° C. After the dropwise addition, the entire mass was further stirred at 25° C. for 2 hours.

To the resulting reaction solution were added 0.64 g (5.22 mmol) of 4-(dimethylamino)pyridine and 13.80 g (52.21 mmol) of 4-(6-acryloyloxy-hex-1-yloxy)phenol (available from DKSH Japan K.K.), and the reactor was again immersed in the water bath to adjust the reaction solution temperature to 15° C. 6.34 g (62.65 mmol) of triethylamine was added dropwise over 10 minutes while retaining the reaction solution temperature to 20° C. to 30° C. After the dropwise addition, the entire mass was further stirred at 25° C. for 2 hours. After completion of the reaction, 1,000 ml of distilled water and 100 ml of saturated brine were added to the reaction solution and extracted twice with 400 ml of ethyl acetate. The organic phases were combined and dried over sodium sulfate anhydrous, and sodium sulfate was filtered off. The solvent was evaporated from the filtrate using a rotary evaporator, and the residue was purified by silica gel column chromatography (THF:toluene=1:9 (volume ratio; hereinafter the same)). Purification by silica gel column chromatography was repeated until purity of ≥99.5% was detected by high performance liquid chromatography. As a consequence, 14.11 g of intermediate A was obtained as a white solid (yield: 65 mol %).

The structure of the target compound was identified by $^1$H-NMR. The result is given below.

$^1$H-NMR (500 MHz, DMSO-d$_6$, TMS, δppm): 12.12 (s, 1H), 6.99 (d, 2H, J=9.0 Hz), 6.92 (d, 2H, J=9.0 Hz), 6.32 (dd, 1H, J=1.5 Hz, 17.5 Hz), 6.17 (dd, 1H, J=10.0 Hz, 17.5 Hz), 5.93 (dd, 1H, J=1.5 Hz, 10.0 Hz), 4.11 (t, 2H, J=6.5 Hz), 3.94 (t, 2H, J=6.5 Hz), 2.48-2.56 (m, 1H), 2.18-2.26 (m, 1H), 2.04-2.10 (m, 2H), 1.93-2.00 (m, 2H), 1.59-1.75 (m, 4H), 1.35-1.52 (m, 8H)

Step 2: Synthesis of Intermediate B to prepare a homogenous solution. 1.12 g (9.78 mmol) of methanesulfonyl chloride was added, and the reactor was immersed in a water bath to adjust the reaction solution temperature to 20° C. 1.01 g (9.99 mmol) of triethylamine was added dropwise over 5 minutes while retaining the reaction solution temperature to 20° C. to 30° C. After the dropwise addition, the entire mass was further stirred at 25° C. for 2 hours. To the resulting reaction solution were added 0.11 g (0.87 mmol) of 4-(dimethylamino)pyridine and 0.60 g (4.35 mmol) of 2,5-dihydroxybenzaldehyde, and the reactor was again immersed in the water bath to adjust the reaction solution temperature to 15° C. 1.10 g (10.87 mmol) of triethylamine was added dropwise over 5 minutes while retaining the reaction solution temperature to 20° C. to 30° C. After the dropwise addition, the entire mass was further stirred at 25° C. for 2 hours. After completion of the reaction, 400 ml of distilled water and 50 ml of saturated brine were added to the reaction solution and extracted twice with 750 ml of ethyl acetate. The organic phases were combined and dried over sodium sulfate anhydrous, and sodium sulfate was filtered off. The solvent was evaporated from the filtrate using a rotary evaporator, and the residue was dissolved in 100 ml of THF. 500 ml of methanol was added to the solution to precipitate crystals and the crystals were filtered off. The crystals obtained were washed with methanol and dried in vacuo to give 2.51 g of intermediate B as a white solid (yield: 62 mol %).

The structure of the target compound was identified by $^1$H-NMR. The result is given below.

$^1$H-NMR (500 MHz, DMSO-d$_6$, TMS, δppm): 10.02 (s, 1H), 7.67 (d, 1H, J=3.0 Hz), 7.55 (dd, 1H, J=3.0 Hz, 8.5 Hz), 7.38 (d, 1H, J=8.5 Hz), 6.99-7.04 (m, 4H), 6.91-6.96 (m, 4H), 6.32 (dd, 2H, J=1.5 Hz, 17.5 Hz), 6.17 (dd, 2H, J=10.0 Hz, 17.5 Hz), 5.93 (dd, 2H, J=1.5 Hz, 10.0 Hz), 4.11 (t, 4H, J=6.5 Hz), 3.95 (t, 4H, J=6.5 Hz), 2.56-2.81 (m, 4H), 2.10-2.26 (m, 8H), 1.50-1.76 (m, 16H), 1.33-1.49 (m, 8H)

Step 3: Synthesis of Compound 1

A three-necked reactor equipped with a thermometer was charged with 2.30 g (2.45 mmol) of intermediate B synthesized in Step 2 and 25 ml of THF under a nitrogen stream to prepare a homogeneous solution to which 0.49 ml (0.25 mmol) of concentrated hydrochloric acid was added. 0.40 g (2.45 mmol) of 2-hydrazinobenzothiazole in 5 ml of THF was added dropwise to the solution over 15 minutes. After

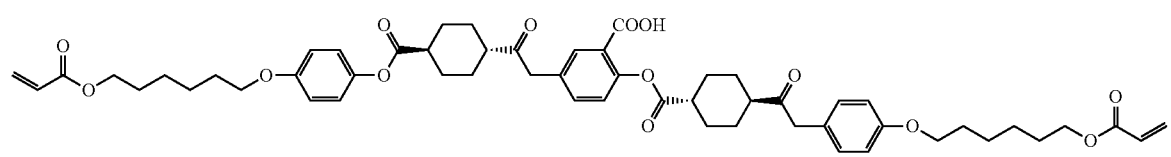

Intermediate B

A three-necked reactor equipped with a thermometer was charged with 4.00 g (9.56 mmol) of intermediate A synthesized in Step 1 and 60 ml of THF under a nitrogen stream the dropwise addition, the entire mass was further stirred at 25° C. for 1 hour. After completion of the reaction, the reaction solution was charged into 400 ml of methanol, and the precipitated solid was filtered off. The solid was dried using a vacuum drier to give 2.4 g of compound 1 as a pale yellow solid (yield: 90 mol %).

The structure of the target compound was identified by $^1$H-NMR. The result is given below.

$^1$H-NMR (500 MHz, DMSO-d$_6$, TMS, δppm): 12.63 (s, 1H), 8.10 (s, 1H), 7.80 (d, 1H, J=5.0 Hz), 7.60 (d, 1H, J=3.0 Hz), 7.48 (s, 1H), 7.21-7.35 (m, 3H), 7.14 (t, 1H, J=7.5 Hz), 6.98-7.05 (m, 4H), 6.91-6.97 (m, 4H), 6.32 (dd, 2H, J=1.5 Hz, 17.5 Hz), 6.18 (dd, 2H, J=10.0 Hz, 17.5 Hz), 5.93 (dd, 2H, J=1.5 Hz, 10.0 Hz), 4.12 (t, 4H, J=6.5 Hz), 3.95 (t, 4H, J=6.5 Hz), 2.56-2.83 (m, 4H), 2.11-2.30 (m, 8H), 1.52-1.80 (m, 16H), 1.33-1.49 (m, 8H)

(Synthesis Example 2) Synthesis of Compound 2

Step 1: Synthesis of Intermediate C

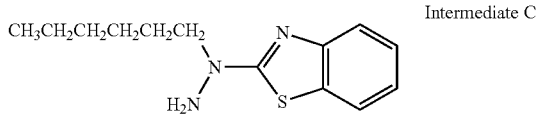

A four-necked reactor equipped with a thermometer was charged with 2.00 g (12.1 mmol) of 2-hydrazinobenzothiazole under a nitrogen stream, which was then dissolved in 20 ml of N,N-dimethylformamide (DMF). To the solution were added 8.36 g (60.5 mmol) of potassium carbonate and 3.08 g (14.5 mmol) of 1-iodohexane, and stirred at 50° C. for 7 hours. After completion of the reaction, the reaction solution was cooled to 20° C., charged into 200 ml of water, and extracted with 300 ml of ethyl acetate. The ethyl acetate phase was dried over sodium sulfate anhydrous. After filtering off sodium sulfate, ethyl acetate was distilled off under reduced pressure using a rotary evaporator to give a yellow solid, which was purified by silica gel column chromatography (hexane:ethyl acetate=75:25) to give 2.10 g of intermediate C as a white solid (yield: 69.6 mol %).

The structure of the target compound was identified by $^1$H-NMR. The result is given below.

$^1$H-NMR (500 MHz, CDCl$_3$, TMS, δppm): 7.60 (dd, 1H, J=1.0 Hz, 8.0 Hz), 7.53 (dd, 1H, J=1.0 Hz, 8.0 Hz), 7.27 (ddd, 1H, J=1.0 Hz, 8.0 Hz, 8.0 Hz), 7.06 (ddd, 1H, J=1.0 Hz, 8.0 Hz, 8.0 Hz), 4.22 (s, 2H), 3.74 (t, 2H, J=7.5 Hz), 1.69-1.76 (m, 2H), 1.29-1.42 (m, 6H), 0.89 (t, 3H, J=7.0 Hz)

Step 2: Synthesis of Compound 2

A four-necked reactor equipped with a thermometer was charged with 697 mg (2.37 mmol) of intermediate C synthesized in Step 1 and 2.00 g (2.13 mmol) of intermediate B synthesized in Step 2 of Synthesis Example 1 under a nitrogen stream, which were then dissolved in a mixture solvent of 3 ml ethanol and 20 ml THF. To the solution was added 55.1 mg (0.237 mmol) of (±)-10-camphorsulfonic acid and stirred at 40° C. for 5 hours. After completion of the reaction, the reaction solution was charged into 150 ml of water and extracted with 300 ml of ethyl acetate. The ethyl acetate phase was dried over sodium sulfate anhydrous. After filtering off sodium sulfate, ethyl acetate was distilled off under reduced pressure using a rotary evaporator to give a white solid, which was purified by silica gel column chromatography (toluene:ethyl acetate=90:10) to give 2.24 g of compound 2 as a white solid (yield: 86.4 mol %).

The structure of the target compound was identified by $^1$H-NMR. The result is given below.

$^1$H-NMR (400 MHz, CDCl$_3$, TMS, δppm): 7.75 (d, 1H, J=2.5 Hz), 7.67-7.70 (m, 3H), 7.34 (ddd, 1H, J=1.0 Hz, 7.0 Hz, 7.5 Hz), 7.17 (ddd, 1H, J=1.0 Hz, 7.5 Hz, 7.5 Hz), 7.12 (d, 1H, J=9.0 Hz), 7.10 (dd, 1H, J=2.5 Hz, 9.0 Hz), 6.99 (d, 2H, J=9.0 Hz), 6.98 (d, 2H, J=9.0 Hz), 6.88 (d, 4H, J=9.0 Hz), 6.40 (dd, 2H, J=1.5 Hz, 17.0 Hz), 6.13 (dd, 2H, J=10.5 Hz, 17.5 Hz), 5.82 (dd, 2H, J=1.5 Hz, 10.5 Hz), 4.30 (t, 2H, J=8.0 Hz), 4.18 (t, 4H, J=6.5 Hz), 3.95 (t, 4H, J=6.5 Hz), 2.58-2.70 (m, 4H), 2.31-2.35 (m, 8H), 1.66-1.82 (m, 18H), 1.31-1.54 (m, 14H), 0.90 (t, 3H, J=7.0 Hz)

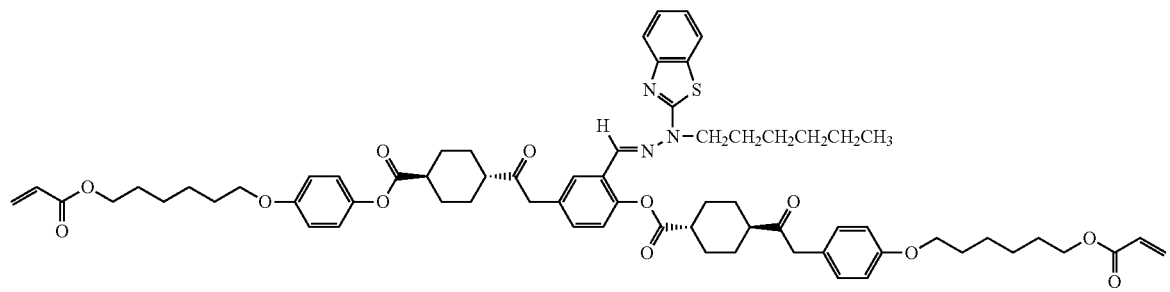

Compound 2

(Synthesis Example 3) Synthesis of Compound 3

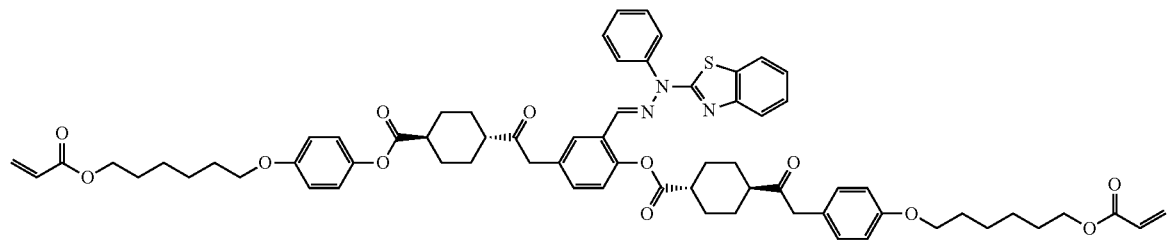

Compound 3

Step 1: Synthesis of Intermediate D

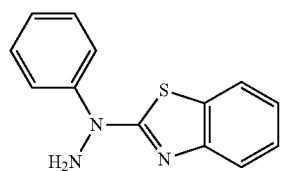

Intermediate D

A three-necked reactor equipped with a thermometer was charged with 3.00 g (17.69 mmol) of 2-chlorobenzothiazole and 7.65 g (70.74 mmol) of phenylhydrazine under a nitrogen stream, which were then dissolved in 30 ml of ethylene glycol. The solution was heated to 140° C. for reaction for 5 hours. 300 ml of distilled water was then added to the reaction solution and extracted twice with 100 ml of ethyl acetate. The combined organic phase was dried over sodium sulfate, concentrated using a rotary evaporator, and dissolved in 15 ml of THF. The solution was charged into 300 ml of distilled water. The precipitated solid was filtered off, washed with distilled water, and dried in vacuo to give a yellow solid. The yellow solid was placed in a flask, 50 ml of toluene was added, and stirred for 30 minutes. The solution was filtered to remove solid components which were insoluble in toluene. The filtrate was concentrated using a rotary evaporator and purified by silica gel column chromatography (THF:toluene=2:50) to give 0.94 g of intermediate D as a yellow oil (yield: 22 mol %).

The structure of the target compound was identified by $^1$H-NMR. The result is given below.

$^1$H-NMR (500 MHz, DMSO-d$_6$, TMS, δppm): 8.01 (dd, 2H, J=1.0 Hz, 9.0 Hz), 7.78 (dd, 1H, J=1.0 Hz, 8.0 Hz), 7.51 (dd, 1H, J=1.0 Hz, 8.0 Hz), 7.43 (dd, 2H, J=7.5 Hz, 8.5 Hz), 7.28 (dt, 1H, J=1.0 Hz, 7.5 Hz), 7.08-7.16 (m, 2H), 6.26 (s, 2H)

Step 2: Synthesis of Compound 3

A three-necked reactor equipped with a thermometer was charged with 1.00 g (1.06 mmol) of intermediate B synthesized in Step 2 for synthesis of compound 1 in Synthesis Example 1 under a nitrogen stream, which was then dissolved in 30 ml of THF. To the solution were added 0.22 ml (0.22 mmol) of 1N hydrochloric acid and 0.38 g (1.60 mmol) of intermediate D synthesized in Step 1, and reacted at 40° C. for 2 hours. The reaction solution was then concentrated using a rotary evaporator and purified by silica gel column chromatography (chloroform:THF=40:1) to give 1.14 g of compound 3 as a pale yellow solid (yield: 95 mol %).

The structure of the target compound was identified by $^1$H-NMR. The result is given below.

$^1$H-NMR (500 MHz, CDCl$_3$, TMS, δppm): 7.82 (d, 1H, J=2.5 Hz), 7.73 (dd, 1H, J=1.0 Hz, 8.0 Hz), 7.64-7.70 (m, 2H), 7.60 (d, 2H, J=7.5 Hz), 7.35-7.42 (m, 3H), 7.30 (dt, 1H, J=1.0 Hz, 7.5 Hz), 7.18 (dt, 1H, J=1.0 Hz, 7.5 Hz), 7.03-7.12 (m, 2H), 7.00 (d, 2H, J=9.0 Hz), 6.99 (d, 2H, J=9.0 Hz), 6.90 (d, 2H, J=9.0 Hz), 6.89 (d, 2H, J=9.0 Hz), 6.41 (dd, 1H, J=1.5 Hz, 17.5 Hz), 6.41 (dd, 1H, J=1.5 Hz, 17.5 Hz), 6.13 (dd, 1H, J=10.5 Hz, 17.5 Hz), 6.13 (dd, 1H, J=10.5 Hz, 17.5 Hz), 5.82 (dd, 1H, J=1.5 Hz, 10.5 Hz), 5.82 (dd, 1H, J=1.5 Hz, 10.5 Hz), 4.18 (t, 2H, J=6.5 Hz), 4.18 (t, 2H, J=6.5 Hz), 3.92-3.98 (m, 4H), 2.56-2.71 (m, 2H), 2.41-2.50 (m, 1H), 2.27-2.40 (m, 5H), 2.12-2.22 (m, 2H), 1.64-1.91 (m, 14H), 1.41-1.56 (m, 10H), 1.19-1.31 (m, 2H)

(Synthesis Example 4) Synthesis of Compound 4

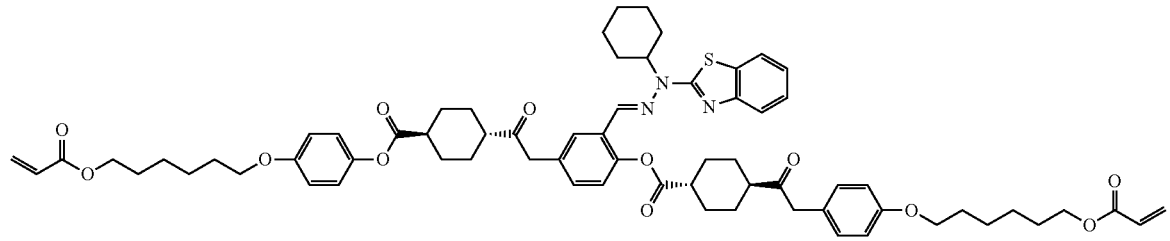

Compound 4

Step 1: Synthesis of Intermediate E

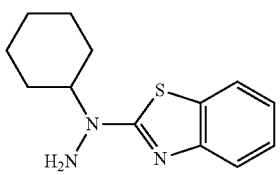

Intermediate E

A four-necked reactor equipped with a thermometer was charged with 2.50 g (16.6 mmol) of cyclohexylhydrazine hydrochloride under a nitrogen stream, which was then dissolved in 8 ml of triethylamine. To the solution was added 5.63 g (33.2 mmol) of 2-chlorobenzothiazole and stirred at 80° C. for 5 hours. After completion of the reaction, the reaction solution was cooled to 20° C., charged into 150 ml of saturated sodium hydrogen carbonate aqueous solution, and extracted with 300 ml of ethyl acetate. The ethyl acetate phase was dried over sodium sulfate anhydrous. After filtering off sodium sulfate, ethyl acetate was distilled off under reduced pressure using a rotary evaporator to give a yellow solid, which was purified by silica gel column chromatography (hexane:ethyl acetate=75:25) to give 1.02 g of intermediate E as a white solid (yield: 22.3 mol %).

The structure of the target compound was identified by $^1$H-NMR. The result is given below.

$^1$H-NMR (400 MHz, CDCl$_3$, TMS, δppm): 7.58 (d, 1H, J=7.8 Hz), 7.52 (d, 1H, J=8.2 Hz), 7.26 (dd, 1H, J=7.4 Hz, 8.2 Hz), 7.05 (dd, 1H, J=7.4 Hz, 7.8 Hz), 4.25-4.32 (m, 1H), 4.04 (s, 2H), 1.84-1.88 (m, 4H), 1.68-1.73 (m, 1H), 1.43-1.59 (m, 4H), 1.08-1.19 (m, 1H)

Step 2: Synthesis of Compound 4

A three-necked reactor equipped with a thermometer was charged with 1.40 g (1.49 mmol) of intermediate B synthesized in step 2 for synthesis of compound 1 in Synthesis Example 1, 456 mg (1.84 mmol) of intermediate E synthesized in Step 1, 38.6 mg (0.166 mmol) of (±)-10-camphorsulfonic acid, 16 ml of THF and 4 ml of ethanol under a nitrogen stream to prepare a homogenous solution. Thereafter, reaction was performed at 40° C. for 5 hours. After completion of the reaction, the reaction solution was charged into 100 ml of water and extracted with 200 ml of ethyl acetate. The ethyl acetate phase was dried over sodium sulfate anhydrous and sodium sulfate was filtered off. Ethyl acetate was distilled off from the filtrate under reduced pressure using a rotary evaporator to give a yellow solid, which was purified by silica gel column chromatography (chloroform:THF=97:3) to give 1.24 g of compound 4 as a pale yellow solid (yield: 71.4 mol %).

The structure of the target compound was identified by $^1$H-NMR. The result is given below.

$^1$H-NMR (500 MHz, CDCl$_3$, TMS, δppm): 8.15 (s, 1H), 7.72 (d, 1H, J=1.5 Hz), 7.68 (dd, 1H, J=1.5 Hz, 8.0 Hz), 7.66 (dd, 1H, J=1.5 Hz, 8.0 Hz), 7.31-7.35 (m, 1H), 7.14-7.18 (m, 1H), 7.13 (d, 1H, J=9.0 Hz), 7.10 (dd, 1H, J=1.5 Hz, 9.0 Hz), 6.96-7.00 (m, 4H), 6.86-6.90 (m, 4H), 6.40 (dd, 2H, J=1.5 Hz, 17.0 Hz), 6.13 (dd, 2H, J=10.0 Hz, 17.0 Hz), 5.82 (dd, 2H, J=1.5 Hz, 10.0 Hz), 4.62-4.70 (m, 1H), 4.17 (t, 4H, J=6.5 Hz), 3.94 (t, 4H, J=6.5 Hz), 2.55-2.74 (m, 4H), 2.27-2.47 (m, 10H), 1.90-2.00 (m, 4H), 1.65-1.85 (m, 16H), 1.42-1.55 (m, 10H), 1.24-1.33 (m, 2H)

(Synthesis Example 5) Synthesis of Compound 5

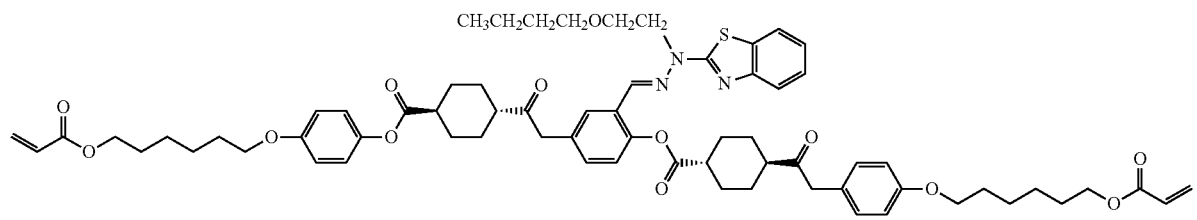

Compound 5

Step 1: Synthesis of Intermediate F

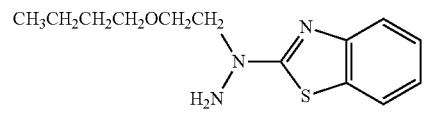

Intermediate F

A three-necked reactor equipped with a thermometer was charged with 2.00 g (12.1 mmol) of 2-hydrazinobenzothiazole under a nitrogen stream, which was then dissolved in 30 ml of DMF. To the solution was added 7.88 g (24.2 mol) of cesium carbonate and the solution was cooled to 0° C., and 1.98 g (14.5 mmol) of butyl 2-chloroethyl ether was added dropwise over 5 minutes. The reaction solution was then warmed back to room temperature (23° C.; hereinafter the same) and stirred for 3 hours. After completion of the reaction, 200 ml of water was added to the reaction solution and extracted twice with 100 ml of ethyl acetate. The combined organic phase was dried over sodium sulfate anhydrous and sodium sulfate was filtered off. After condensation using a rotary evaporator, purification was performed by silica gel column chromatography (n-hexane: ethyl acetate=75:25) to give 1.70 g of intermediate F as a white solid (yield: 53.0 mol %).

The structure of the target compound was identified by $^1$H-NMR. The result is given below.

$^1$H-NMR (500 MHz, CDCl$_3$, TMS, δppm): 7.61 (dd, 1H, J=1.0 Hz, 8.0 Hz), 7.50 (dd, 1H, J=1.0 Hz, 8.0 Hz), 7.27-7.29 (m, 1H), 7.04-7.08 (m, 1H), 4.70 (s, 2H), 4.01 (t, 2H, J=5.0 Hz), 3.82 (t, 2H, J=5.0 Hz), 3.44 (t, 2H, J=7.0 Hz), 1.52-1.57 (m, 2H), 1.31-1.39 (m, 2H), 0.90 (t, 3H, J=7.0 Hz)

Step 2: Synthesis of Compound 5

A three-necked reactor equipped with a thermometer was charged with 1.50 g (1.60 mmol) of intermediate B synthesized in Step 2 of Synthesis Example 1, 396 mg (1.78 mmol)

of intermediate F synthesized in Step 1, 41.4 mg (0.178 mmol) of (±)-10-camphorsulfonic acid, 16 ml of THF and 4 ml of ethanol under a nitrogen stream to prepare a homogenous solution. Thereafter, reaction was performed at 40° C. for 5 hours. After completion of the reaction, the reaction solution was charged into 100 ml of water and extracted with 200 ml of ethyl acetate. The ethyl acetate phase was dried over sodium sulfate anhydrous and sodium sulfate was filtered off. Ethyl acetate was distilled off from the filtrate under reduced pressure using a rotary evaporator to give a yellow solid, which was purified by silica gel column chromatography (toluene:ethyl acetate=9:1) to give 1.31 g of compound 5 as a pale yellow solid (yield: 69.4 mol %).

The structure of the target compound was identified by $^1$H-NMR. The result is given below.

$^1$H-NMR (500 MHz, CDCl$_3$, TMS, δppm): 8.03 (s, 1H), 7.76 (d, 1H, J=1.5 Hz), 7.65-7.71 (m, 2H), 7.34 (ddd, 1H, J=1.5 Hz, 8.0 Hz, 8.0 Hz), 7.17 (ddd, 1H, J=1.5 Hz, 8.0 Hz, 8.0 Hz), 7.09-7.12 (m, 2H), 6.96-7.00 (m, 4H), 6.87-6.90 (m, 4H), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 4.45 (t, 2H, J=5.5 Hz), 4.18 (t, 4H, J=7.0 Hz), 3.95 (t, 4H, J=7.0 Hz), 3.79 (t, 2H, J=5.5 Hz), 3.44 (t, 2H, J=7.0 Hz), 2.55-2.74 (m, 4H), 2.28-2.40 (m, 8H), 1.65-1.83 (m, 16H), 1.42-1.55 (m, 10H), 1.25-1.34 (m, 2H), 0.85 (t, 3H, J=7.0 Hz)

(Synthesis Example 6) Synthesis of Compound 6 acetate was distilled off under reduced pressure using a rotary evaporator to give a yellow solid, which was purified by silica gel column chromatography (n-hexane:ethyl acetate=70:30) to give 4.40 g of intermediate G as a white solid (yield: 49.5 mol %).

The structure of the target compound was identified by $^1$H-NMR. The result is given below.

$^1$H-NMR (500 MHz, CDCl$_3$, TMS, δppm): 7.60 (dd, 1H, J=1.0 Hz, 8.0 Hz), 7.54 (dd, 1H, J=1.0 Hz, 8.0 Hz), 7.28 (ddd, 1H, J=1.0 Hz, 7.5 Hz, 8.0 Hz), 7.06 (ddd, 1H, J=1.0 Hz, 7.5 Hz, 8.0 Hz), 5.89 (ddt, 1H, J=7.0 Hz, 10.5 Hz, 17.0 Hz), 5.17 (ddt, 1H, J=1.5 Hz, 3.0 Hz, 17.0 Hz), 5.09 (ddt, 1H, J=1.0 Hz, 3.0 Hz, 10.5 Hz), 4.26 (s, 2H), 3.85 (t, 2H, J=7.0 Hz), 2.52 (dddt, 2H, J=1.0 Hz, 1.5 Hz, 7.0 Hz, 7.0 Hz)

Step 2: Synthesis of Compound 6

A four-necked reactor equipped with a thermometer was charged with 195 mg (1.77 mmol) of intermediate G synthesized in Step 1 and 1.50 g (1.60 mmol) of intermediate B synthesized in Step 2 for synthesis of compound 1 in Synthesis Example 1 under a nitrogen stream, which were then dissolved in a mixture solvent of 3 ml ethanol and 15 ml THF. To the solution was added 41.2 mg (0.177 mmol) of (±)-10-camphorsulfonic acid and stirred at 40° C. for 8 hours. After completion of the reaction, the reaction solution was charged into 150 ml of water and extracted with 300 ml of ethyl acetate. The ethyl acetate phase was dried over sodium sulfate anhydrous. After filtering off sodium sulfate, Compound 6

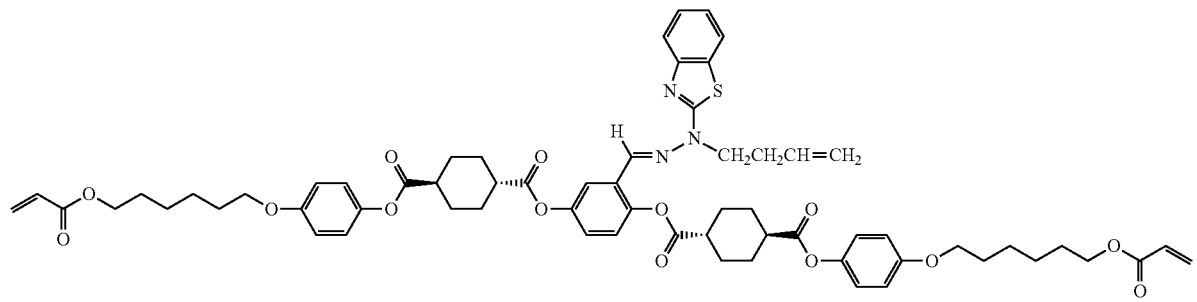

Step 1: Synthesis of Intermediate G

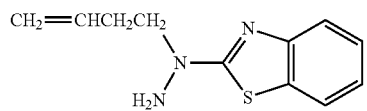

Intermediate G

A four-necked reactor equipped with a thermometer was charged with 5.04 g (30.5 mmol) of 2-hydrazinobenzothiazole under a nitrogen stream, which was then dissolved in 50 ml of DMF. To the solution was added 14.9 g (45.8 mmol) of cesium carbonate and 4.94 g (36.6 mmol) of 4-bromo-1-butene, and stirred at room temperature for 7 hours. After completion of the reaction, the reaction solution was charged into 200 ml of water and extracted with 300 ml ethyl acetate. The ethyl acetate phase was dried over sodium sulfate anhydrous. After filtering off sodium sulfate, ethyl ethyl acetate was distilled off under reduced pressure using a rotary evaporator to give a yellow solid, which was purified by silica gel column chromatography (toluene:ethyl acetate=90:10) to give 1.26 g of compound 6 as a white solid (yield: 69.3 mol %).

The structure of the target compound was identified by $^1$H-NMR. The result is given below.

$^1$H-NMR (500 MHz, CDCl$_3$, TMS, δppm): 7.76 (d, 1H, J=2.5 Hz), 7.67-7.70 (m, 3H), 7.35 (ddd, 1H, J=1.5 Hz, 7.5 Hz, 8.0 Hz), 7.18 (ddd, 1H, J=1.5 Hz, 7.5 Hz, 8.0 Hz), 7.10-7.14 (m, 2H), 6.99 (d, 2H, J=9.5 Hz), 6.98 (d, 2H, J=9.5 Hz), 6.88 (d, 4H, J=9.5 Hz), 6.40 (dd, 2H, J=1.5 Hz, 17.5 Hz), 6.13 (dd, 2H, J=10.5 Hz, 17.5 Hz), 5.89 (ddt, 1H, J=6.5 Hz, 10.5 Hz, 17.0 Hz), 5.82 (dd, 2H, J=1.5 Hz, 10.5 Hz), 5.18 (dd, 1H, J=1.5 Hz, 17.0 Hz), 5.15 (dd, 1H, J=1.5 Hz, 10.5 Hz), 4.38 (t, 2H, J=7.0 Hz), 4.18 (t, 4H, J=6.5 Hz), 3.95 (t, 4H, J=6.5 Hz), 2.58-2.68 (m, 4H), 2.51 (dt, 2H, J=6.5 Hz, 7.0 Hz), 2.31-2.35 (m, 8H), 1.76-1.85 (m, 4H), 1.65-1.74 (m, 12H), 1.41-1.54 (m, 8H)

(Synthesis Example 7) Synthesis of Compound 7

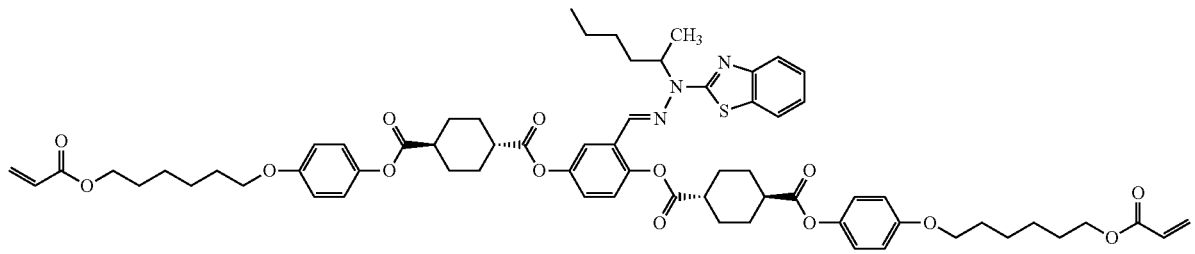

Compound 7

Step 1: Synthesis of Intermediate H

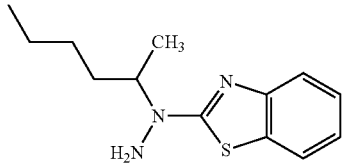

Intermediate H

A three-necked reactor equipped with a thermometer was charged with 2.00 g (12.1 mmol) of 2-hydrazinobenzothiazole under a nitrogen stream, which was then dissolved in 30 ml of DMF. To the solution was added 7.88 g (24.2 mol) of cesium carbonate and the solution was cooled to 0° C., and 2.39 g (14.5 mmol) of 2-bromohexane was added dropwise over 5 minutes. The reaction solution was then warmed back to room temperature and stirred for 3 hours. After completion of the reaction, 200 ml of water was added to the reaction solution and extracted twice with 100 ml of ethyl acetate. The combined organic phase was dried over sodium sulfate anhydrous and sodium sulfate was filtered off. After condensation using a rotary evaporator, purification was performed by silica gel column chromatography (n-hexane:ethyl acetate=93:7) to give 1.61 g of intermediate H as a white solid (yield: 53.4 mol %).

The structure of the target compound was identified by $^1$H-NMR. The result is given below.

$^1$H-NMR (400 MHz, CDCl$_3$, TMS, δppm): 7.59 (dd, 1H, J=1.0 Hz, 8.0 Hz), 7.52 (dd, 1H, J=1.0 Hz, 8.0 Hz), 7.24-7.30 (m, 1H), 7.05 (ddd, 1H, J=1.0 Hz, 8.0 Hz, 8.0 Hz), 3.97 (s, 2H), 1.47-1.74 (m, 3H), 1.20-1.41 (m, 7H), 0.89 (t, 3H, J=5.5 Hz)

Step 2: Synthesis of Compound 7

A three-necked reactor equipped with a thermometer was charged with 1.50 g (1.60 mmol) of intermediate B synthesized in Step 2 for synthesis of compound 1 in Synthesis Example 1, 444 mg (1.78 mmol) of intermediate H synthesized in Step 1, 41.4 mg (0.178 mmol) of (±)-10-camphorsulfonic acid, 16 ml of THF and 4 ml of ethanol under a nitrogen stream to prepare a homogenous solution. Thereafter, reaction was performed at 40° C. for 5 hours. After completion of the reaction, the reaction solution was charged into 100 ml of water and extracted with 200 ml of chloroform. The organic phase was dried over sodium sulfate anhydrous and sodium sulfate was filtered off. After condensation using a rotary evaporator, purification was performed by silica gel column chromatography (toluene:ethyl acetate=92:8) to give 1.35 g of compound 7 as a pale yellow solid (yield: 72.4 mol %).

The structure of the target compound was identified by $^1$H-NMR. The result is given below.

$^1$H-NMR (500 MHz, CDCl$_3$, TMS, δppm): 8.04 (s, 1H), 7.73 (d, 1H, J=1.5 Hz), 7.69 (dd, 1H, J=1.5 Hz, 7.8 Hz), 7.65 (dd, 1H, J=1.5 Hz, 7.8 Hz), 7.33 (ddd, 1H, J=1.5 Hz, 7.8 Hz, 7.8 Hz), 7.07-7.19 (m, 3H), 6.95-7.01 (m, 4H), 6.85-6.91 (m, 4H), 6.40 (dd, 2H, J=1.5 Hz, 17.5 Hz), 6.13 (dd, 2H, J=10.5 Hz, 17.5 Hz), 5.82 (dd, 2H, J=1.5 Hz, 10.5 Hz), 4.18 (t, 4H, J=6.5 Hz), 3.95 (t, 4H, J=6.5 Hz), 2.54-2.73 (m, 4H), 2.25-2.40 (m, 8H), 1.65-1.83 (m, 16H), 1.60-1.62 (m, 2H), 1.57 (d, 3H, J=7.5 Hz), 1.24-1.55 (m, 13H), 0.87 (t, 3H, J=7.5 Hz)

(Synthesis Example 8) Synthesis of 8

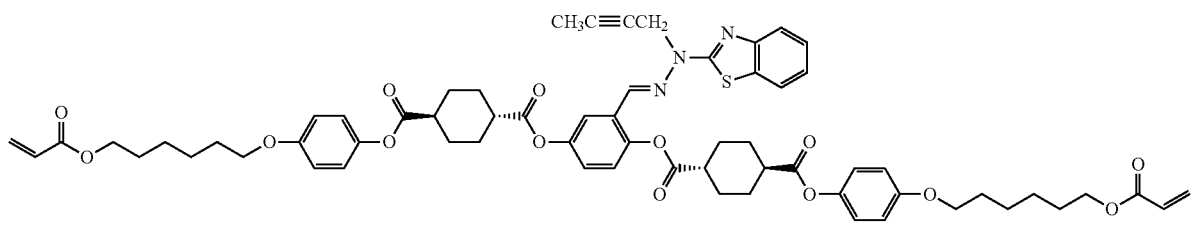

Compound 8

Step 1: Synthesis of Intermediate I

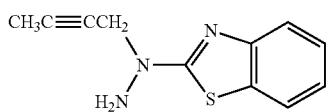
Intermediate I

A four-necked reactor equipped with a thermometer was charged with 2.00 g (12.1 mmol) of 2-hydrazinobenzothiazole under a nitrogen stream, which was then dissolved in 30 ml of DMF. To the solution was added 7.88 g (24.2 mol) of cesium carbonate and 1.93 g (14.5 mmol) of 1-bromo-2-butyne and stirred at room temperature for 20 hours. After completion of the reaction, the reaction solution was charged into 200 ml of water and extracted with 300 ml of ethyl acetate. The ethyl acetate phase was dried over sodium sulfate anhydrous. After filtering off sodium sulfate, ethyl acetate was distilled off under reduced pressure using a rotary evaporator to give a brown solid, which was purified by silica gel column chromatography (n-hexane:ethyl acetate=85:15) to give 1.25 g of intermediate I as a white solid (yield: 47.5 mol %).

The structure of the target compound was identified by $^1$H-NMR. The result is given below.

$^1$H-NMR (500 MHz, CDCl$_3$, TMS, δppm): 7.63 (dd, 1H, J=1.3 Hz, 7.8 Hz), 7.58 (dd, 1H, J=1.3 Hz, 7.8 Hz), 7.29 (ddd, 1H, J=1.3 Hz, 7.8 Hz, 7.8 Hz), 7.10 (ddd, 1H, J=1.3 Hz, 7.8 Hz, 7.8 Hz), 4.56 (q, 2H, J=2.5 Hz), 4.36 (s, 2H), 1.84 (t, 3H, J=2.5 Hz)

Step 2: Synthesis of Compound 8

A three-necked reactor equipped with a thermometer was charged with 1.50 g (1.60 mmol) of intermediate B synthesized in Step 2 for synthesis of compound 1 in Synthesis Example 1, 387 mg (1.78 mmol) of intermediate I synthesized in Step 1, 41.4 mg (0.178 mmol) of (±)-10-camphorsulfonic acid, 16 ml of THF and 4 ml of ethanol under a nitrogen stream to prepare a homogenous solution. Thereafter, reaction was performed at 40° C. for 5 hours. After completion of the reaction, the reaction solution was charged into 100 ml of water and extracted with 200 ml of chloroform. The organic phase was dried over sodium sulfate anhydrous and sodium sulfate was filtered off. After condensation using a rotary evaporator, purification was performed by silica gel column chromatography (toluene:ethyl acetate=9:1) to give 1.54 g of compound 8 as a pale yellow solid (yield: 84.9 mol %).

The structure of the target compound was identified by $^1$H-NMR. The result is given below.

$^1$H-NMR (500 MHz, CDCl$_3$, TMS, δppm): 7.90 (s, 1H), 7.78 (d, 1H, J=1.3 Hz), 7.67-7.73 (m, 2H), 7.35 (ddd, 1H, J=1.3 Hz, 7.5 Hz, 7.5 Hz), 7.18 (ddd, 1H, J=1.3 Hz, 7.5 Hz, 7.5 Hz), 7.09-7.15 (m, 2H), 6.95-7.01 (m, 4H), 6.85-6.91 (m, 4H), 6.40 (dd, 2H, J=1.5 Hz, 17.0 Hz), 6.13 (dd, 2H, J=10.5 Hz, 17.0 Hz), 5.82 (dd, 2H, J=1.5 Hz, 10.5 Hz), 5.06 (d, 2H, J=2.0 Hz), 4.18 (t, 4H, J=6.0 Hz), 3.95 (t, 4H, J=6.0 Hz), 2.55-2.76 (m, 4H), 2.26-2.43 (m, 8H), 1.64-1.83 (m, 19H), 1.41-1.55 (m, 8H)

(Synthesis Example 9) Synthesis of Compound 9

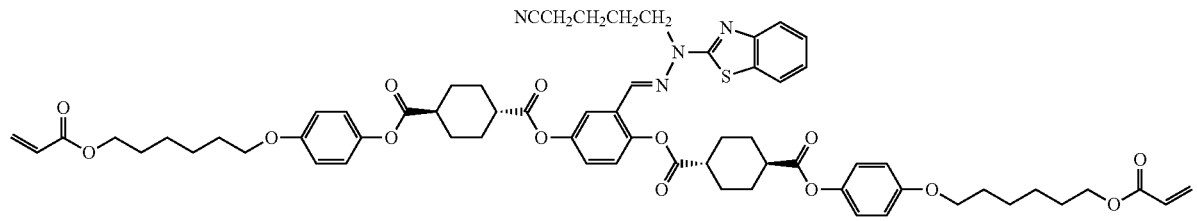
Compound 9

Step 1: Synthesis of Intermediate J

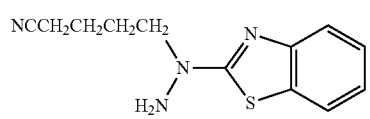
Intermediate J

A four-necked reactor equipped with a thermometer was charged with 5.00 g (30.3 mmol) of 2-hydrazinobenzothiazole under a nitrogen stream, which was then dissolved in 100 ml of DMF. To the solution was added 20.9 g (152 mmol) of potassium carbonate and 5.17 g (30.3 mmol) of 5-bromovaleronitrile and stirred at 60° C. for 8 hours. After completion of the reaction, the reaction solution was cooled to 20° C., charged into 500 ml of water, and extracted with 500 ml of ethyl acetate. The ethyl acetate phase was dried over sodium sulfate anhydrous. After filtering off sodium sulfate, ethyl acetate was distilled off under reduced pressure using a rotary evaporator to give a yellow solid, which was purified by silica gel column chromatography (n-hexane:ethyl acetate=60:40) to give 3.41 g of intermediate J as a white solid (yield: 45.7 mol %).

The structure of the target compound was identified by $^1$H-NMR. The result is given below.

$^1$H-NMR (400 MHz, CDCl$_3$, TMS, δppm): 7.60 (d, 1H, J=7.8 Hz), 7.51 (d, 1H, J=8.1 Hz), 7.28 (dd, 1H, J=7.3, 8.1 Hz), 7.07 (dd, 1H, J=7.3 Hz, 7.8 Hz), 4.23 (s, 2H), 3.81 (t, 2H, J=6.9 Hz), 2.46 (t, 2H, J=7.1 Hz), 1.88-1.95 (m, 2H), 1.71-1.79 (m, 2H)

Step 2: Synthesis of Compound 9

A three-necked reactor equipped with a thermometer was charged with 1.50 g (1.60 mmol) of intermediate B synthesized in Step 2 for synthesis of compound 1 in Synthesis Example 1, 438 mg (1.78 mmol) of intermediate J synthesized in Step 1, 41.4 mg (0.178 mmol) of (±)-10-camphorsulfonic acid, 16 ml of THF and 4 ml of ethanol under a nitrogen stream to prepare a homogenous solution. Thereafter, reaction was performed at 40° C. for 5 hours. After completion of the reaction, the reaction solution was charged into 100 ml of water and extracted with 200 ml of ethyl acetate. The ethyl acetate phase was dried over sodium sulfate anhydrous and sodium sulfate was filtered off. Ethyl acetate was distilled off from the filtrate under reduced pressure using a rotary evaporator to give a yellow solid, which was purified by silica gel column chromatography (toluene:ethyl acetate=85:15) to give 1.31 g of compound 9 as a pale yellow solid (yield: 70.2 mol %). The structure of the target compound was identified by $^1$H-NMR. The result is given below.

$^1$H-NMR (500 MHz, CDCl$_3$, TMS, δppm): 7.74 (d, 1H, J=1.5 Hz), 7.64-7.72 (m, 3H), 7.35 (ddd, 1H, J=1.5 Hz, 8.0 Hz, 8.0 Hz), 7.19 (ddd, 1H, J=1.5 Hz, 8.0 Hz, 8.0 Hz), 7.10-7.14 (m, 2H), 6.96-7.01 (m, 4H), 6.86-6.91 (m, 4H), 6.40 (dd, 2H, J=1.5 Hz, 17.0 Hz), 6.12 (dd, 2H, J=10.5 Hz, 17.0 Hz), 5.82 (dd, 2H, J=1.5 Hz, 10.5 Hz), 4.22 (t, 2H, J=6.5 Hz), 4.18 (t, 4H, J=6.5 Hz), 3.95 (t, 4H, J=6.5 Hz), 2.58-2.75 (m, 4H), 2.55 (t, 2H, J=6.5 Hz), 2.26-2.40 (m, 8H), 1.96 (tt, 2H, J=6.5 Hz, 6.5 Hz), 1.66-1.83 (m, 18H), 1.42-1.55 (m, 8H)

(Example 1) Synthesis of Compound X

After addition of sodium hydroxide the reaction mass was heated and further reacted at reflux (96° C.) for 12 hours.

After completion of the reaction, the temperature of the reaction solution was lowered to 80° C., 200 g of distilled water was added, and the reaction solution was cooled to 10° C. allowing crystals to precipitate. The precipitated crystals were isolated by filtration, washed with 500 g of distilled water, and dried in vacuo to give 123.3 g of brown crystals.

High-performance liquid chromatography of the brown crystals revealed that the mole ratio of the abundance of compounds in the brown crystals was hydroquinone/intermediate K/by-product K=1.3/90.1/8.1. The mixture was directly used in Step 2 without purification.

Step 2: Synthesis of Intermediate L

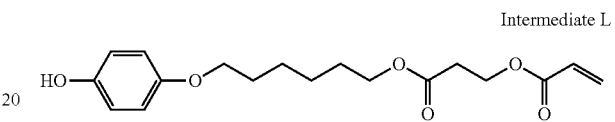

Intermediate L

A three-necked reactor equipped with a thermometer and a condenser with a Dean-Stark trap was charged with 10.00 g of the brown crystals containing intermediate K synthesized in Step 1, 100 g of toluene and 0.105 g (0.476 mmol) of 2,6-di-t-butyl-p-cresol under a nitrogen stream, and the entire mass was stirred. The solution was heated to 80° C., 20.56 g (0.1427 mol) of 2-carboxyethyl acrylate and 1.37 g (14.3 mmol) of methanesulfonic acid were added, and

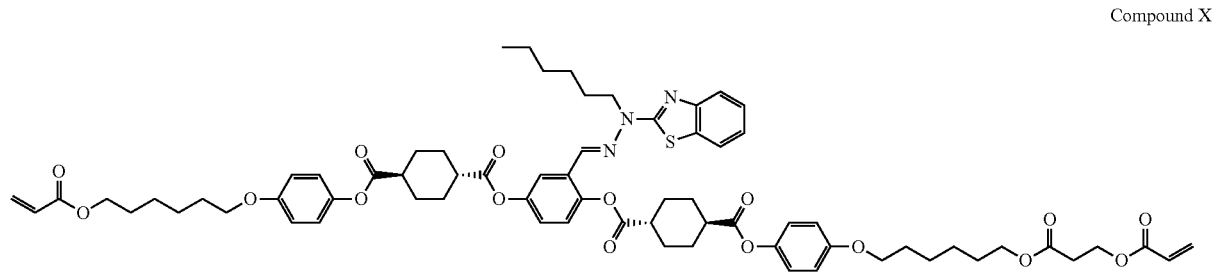 [SMILES: C=CC(=O)OCCCCCCOc1ccc(OC(=O)[C@H]2CC[C@H](C(=O)Oc3ccc(OC(=O)[C@H]4CC[C@H](C(=O)Oc5ccc(OCCCCCCOC(=O)CCOC(=O)C=C)cc5)CC4)c(/C=N/N(CCCCCC)c4nc5ccccc5s4)c3)CC2)cc1]

Compound X

Step 1: Synthesis of Intermediate K

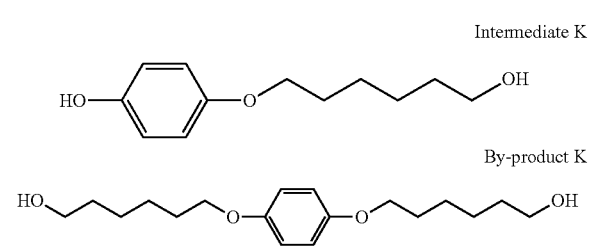

Intermediate K

By-product K

A three-necked reactor equipped with a condenser and a thermometer was charged with 104.77 g (0.9515 mol) of hydroquinone, 100 g (0.7320 mol) of 6-chlorohexanol, 500 g of distilled water and 100 g of o-xylene under a nitrogen stream. 35.15 g (0.8784 mol) of sodium hydroxide was further added gradually with stirring over 20 minutes so that the temperature of the reaction mass does not exceed 40° C.

dehydration reaction was performed at reflux (110° C.) for 2 hours with generated water removed out of the system. The reaction solution was then cooled to 30° C. and 500 g of distilled water was added. After stirring, the entire mass was allowed to stand. The organic phase was separated and 500 g of 5% brine was added for phase separation. The organic phase was separated and dried over sodium sulfate anhydrous, and sodium sulfate was filtered off. After condensation using a rotary evaporator, purification was performed by silica gel column chromatography (toluene:ethyl acetate=8:1) to give a total of 7.93 g of intermediate L as a white solid in Steps 1 and 2 (yield: 40 mol %).

The structure of the target compound was identified by $^1$H-NMR. The result is given below.

$^1$H-NMR (500 MHz, CDCl$_3$, TMS, δppm): 6.77 (d, 2H, J=9.0 Hz), 6.76 (d, 2H, J=9.0 Hz), 6.41 (dd, 1H, J=1.5 Hz, 17.5 Hz), 6.11 (dd, 1H, J=10.5 Hz, 17.5 Hz), 5.83 (dd, 1H, J=1.5 Hz, 10.5 Hz), 4.83 (s, 1H), 4.44 (t, 2H, J=6.5 Hz), 4.13 (t, 2H, J=6.5 Hz), 3.89 (t, 2H, J=6.5 Hz), 2.69 (t, 2H, J=6.5 Hz), 1.71-1.80 (m, 2H), 1.62-1.70 (m, 2H), 1.36-1.52 (m, 4H)

Step 3: Synthesis of Intermediate M

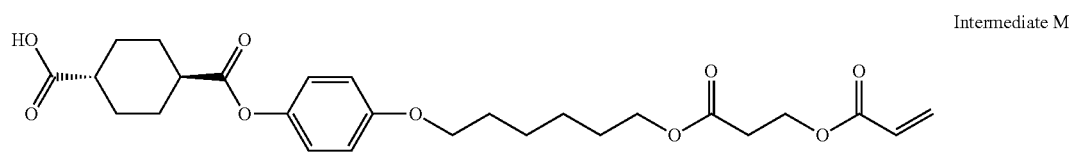 [SMILES: C=CC(=O)OCCC(=O)OCCCCCCOc1ccc(OC(=O)[C@H]2CC[C@H](C(=O)O)CC2)cc1]
Intermediate M

A three-necked reactor equipped with a thermometer was charged with 3.58 g (0.0208 mol) of trans-1,4-cyclohexanedicarboxylic acid and 25 ml of THF under a nitrogen stream. 1.25 g (0.0109 mol) of methanesulfonyl chloride was added, and the reactor was immersed in a water bath to adjust the reaction solution temperature to 5° C. 1.15 g (0.0114 mol) of triethylamine was added dropwise over 15 minutes so that the reaction solution temperature becomes 15° C. or below. After stirring the reaction solution at 5° C. for 1 hour, 0.127 g (1.04 mmol) of 4-(dimethylamino) pyridine and 3.51 g (0.0104 mol) of intermediate L were added, and 1.15 g (0.0114 mol) of triethylamine was added dropwise over 15 minutes so that the reaction solution temperature becomes 15° C. or below. The reaction solution was reacted at 25° C. for 2 hours. After completion of the reaction, 300 ml of distilled water and 30 ml of saturated brine were added to the reaction solution and extracted twice with 200 ml of chloroform. The combined organic phase was dried over sodium sulfate anhydrous and sodium sulfate was filtered off. After condensation using a rotary evaporator, purification was performed by silica gel column chromatography (chloroform:THF=95:5) to give 2.41 g of intermediate M as a white solid (yield: 47 mol %).

The structure of the target compound was identified by $^1$H-NMR. The result is given below.

$^1$H-NMR (500 MHz, CDCl$_3$, TMS, δppm): 6.96 (d, 2H, J=9.0 Hz), 6.86 (d, 2H, J=9.0 Hz), 6.41 (dd, 1H, J=1.5 Hz, 17.5 Hz), 6.11 (dd, 1H, J=10.5 Hz, 17.5 Hz), 5.83 (dd, 1H, J=1.5 Hz, 10.5 Hz), 4.44 (t, 2H, J=6.5 Hz), 4.13 (t, 2H, J=6.5 Hz), 3.93 (t, 2H, J=6.5 Hz), 2.69 (t, 2H, J=6.5 Hz), 2.47-2.57 (m, 1H), 2.34-2.43 (m, 1H), 2.12-2.28 (m, 4H), 1.73-1.82 (m, 2H), 1.36-1.71 (m, 10H)

Step 4: Synthesis of Intermediate N

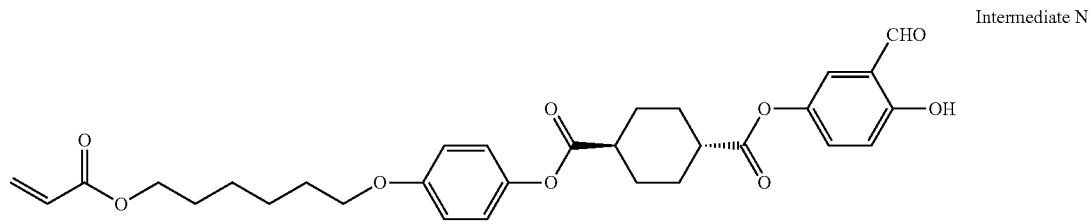 [SMILES: C=CC(=O)OCCCCCCOc1ccc(OC(=O)[C@H]2CC[C@H](C(=O)Oc3ccc(O)c(C=O)c3)CC2)cc1]
Intermediate N

A three-necked reactor equipped with a thermometer was charged with 3.90 g (8.85 mmol) of intermediate A synthesized in Step 1 of Synthesis Example 1, 0.52 g (7.1 mmol) of DMF and 39 g of toluene under a nitrogen stream. The solution was cooled to 5° C. and 1.10 g (9.3 mmol) of thionyl chloride was added dropwise over 10 minutes, and reaction was performed at 5° C. for 1 hour. The reaction solution was then condensed using a rotary evaporator and dried in vacuo to give a white solid.

Further, a three-necked reactor equipped with a thermometer was charged with 6.10 g (0.0443 mol) of 2,5-dihydroxybenzaldehyde and 0.985 g (9.7 mmol) of triethylamine under a nitrogen stream, which were then dissolved in 35 g of THF. The solution was cooled to 5° C., and the white solid obtained above was added and reacted for 30 minutes. 200 ml of distilled water and 10 ml of saturated brine were then added to the reaction solution and extracted twice with 100 ml of ethyl acetate. The combined organic phase was dried over sodium sulfate anhydrous and sodium sulfate was filtered off. After condensation using a rotary evaporator, purification was performed by silica gel column chromatography (toluene:THF=95:5) to give 1.53 g of intermediate N as a white solid (yield: 32 mol %).

The structure of the target compound was identified by $^1$H-NMR. The result is given below.

$^1$H-NMR (500 MHz, CDCl$_3$, TMS, δppm): 10.91 (s, 1H), 9.86 (s, 1H), 7.32 (d, 1H, J=3.0 Hz), 7.24 (dd, 1H, J=3.0 Hz, 9.0 Hz), 7.01 (d, 1H, J=9.0 Hz), 6.97 (d, 2H, J=9.0 Hz), 6.87 (d, 2H, J=9.0 Hz), 6.40 (dd, 1H, J=1.5 Hz, 17.5 Hz), 6.12 (dd, 1H, J=10.5 Hz, 17.5 Hz), 5.82 (dd, 1H, J=1.5 Hz, 10.5 Hz), 4.17 (t, 2H, J=6.5 Hz), 3.94 (t, 2H, J=6.5 Hz), 2.51-2.65 (m, 2H), 2.20-2.35 (m, 4H), 1.75-1.83 (m, 2H), 1.63-1.75 (m, 6H), 1.36-1.55 (m, 4H)

Step 6: Synthesis of Intermediate P

A three-necked reactor equipped with a thermometer was charged with 1.00 g (2.04 mmol) of intermediate M synthesized in Step 3 under a nitrogen stream, which was then dissolved in 15 ml of THF. 0.234 g (2.04 mmol) of methanesulfonyl chloride was added, the reaction solution was cooled to 5° C., and 0.236 g (2.33 mmol) of triethylamine was added dropwise over 10 minutes. After reacting the reaction solution at 5° C. for 1 hour, 0.018 g (0.15 mmol) of 4-dimethylaminopyridine and 0.786 g (1.46 mmol) of intermediate N synthesized in Step 4 were added, and 0.177 g (1.75 mmol) of triethylamine was added dropwise over 10 minutes. After reacting the reaction solution at 25° C. for 2 hours, 200 ml of distilled water and 20 ml of saturated brine were added to the reaction solution and extracted twice with 100 ml of chloroform. The combined organic phase was dried over sodium sulfate anhydrous and sodium sulfate was filtered off. After condensation using a rotary evaporator, purification was performed by silica gel column chromatography (chloroform:THF=99:1) to give 1.15 g of intermediate P as a white solid (yield: 78 mol %).

The structure of the target compound was identified by $^1$H-NMR. The result is given below.

$^1$H-NMR (500 MHz, DMSO-d$_6$, TMS, δppm): 10.08 (s, 1H), 7.61 (d, 1H, J=3.0 Hz), 7.37 (dd, 1H, J=3.0 Hz, 9.0 Hz), 7.20 (d, 1H, J=9.0 Hz), 6.98 (d, 2H, J=9.0 Hz), 6.97 (d, 2H, J=9.0 Hz), 6.88 (d, 2H, J=9.0 Hz), 6.88 (d, 2H, J=9.0 Hz), 6.41 (dd, 1H, J=1.5 Hz, 17.5 Hz), 6.40 (dd, 1H, J=1.5 Hz, 17.5 Hz), 6.13 (dd, 1H, J=10.5 Hz, 17.5 Hz), 6.11 (dd, 1H, J=10.5 Hz, 17.5 Hz), 5.83 (dd, 1H, J=1.5 Hz, 10.5 Hz), 5.82 (dd, 1H, J=1.5 Hz, 10.5 Hz), 4.44 (t, 2H, J=6.5 Hz), 4.17 (t, 2H, J=6.5 Hz), 4.13 (t, 2H, J=6.5 Hz), 3.94 (t, 2H, J=6.5 Hz), 3.94 (t, 2H, J=6.5 Hz), 2.53-2.74 (m, 6H), 2.20-2.39 (m, 8H), 1.60-1.83 (m, 16H), 1.34-1.56 (m, 8H)

Step 7: Synthesis of Compound X

A three-necked reactor equipped with a thermometer was charged with 0.944 g (0.934 mmol) of intermediate P synthesized in Step 6, 0.279 g (1.12 mmol) of intermediate C synthesized in Step 1 of Synthesis Example 2 and 0.02 g of 2,6-di-t-butyl-p-cresol under a nitrogen stream, which were then dissolved in 15 ml of THF. To the solution were added 44 mg (0.189 mmol) of (±)-10-camphorsulfonic acid and 2 ml of ethanol and heated to 40° C. for reaction for 5 hours. After completion of the reaction, 100 ml of distilled water and 15 ml of saturated brine were added to the reaction solution and extracted twice with 100 ml of ethyl acetate. The combined organic phase was dried over sodium sulfate anhydrous and sodium sulfate was filtered off. After condensation using a rotary evaporator, the resulting solid was dissolved in 10 ml of chloroform. To the solution was added 150 ml of methanol to precipitate crystals, which were filtered off, washed with methanol and dried in vacuo to give 0.986 g of compound X as a pale yellow solid (yield: 80 mol %). The structure of the target compound was identified by $^1$H-NMR. The result is given below.

$^1$H-NMR (500 MHz, DMSO-d$_6$, TMS, δppm): 7.75 (d, 1H, J=2.5 Hz), 7.65-7.71 (m, 3H), 7.34 (dd, 1H, J=1.0 Hz, 7.5 Hz), 7.17 (dd, 1H, J=1.0 Hz, 7.5 Hz), 7.07-7.14 (m, 2H), 6.99 (d, 2H, J=9.0 Hz), 6.98 (d, 2H, J=9.0 Hz), 6.88 (d, 2H, J=9.0 Hz), 6.88 (d, 2H, J=9.0 Hz), 6.41 (dd, 1H, J=1.5 Hz, 17.5 Hz), 6.40 (dd, 1H, J=1.5 Hz, 17.5 Hz), 6.13 (dd, 1H, J=10.5 Hz, 17.5 Hz), 6.11 (dd, 1H, J=10.5 Hz, 17.5 Hz), 5.83 (dd, 1H, J=1.5 Hz, 10.5 Hz), 5.82 (dd, 1H, J=1.5 Hz, 10.5 Hz), 4.44 (t, 2H, J=6.5 Hz), 4.30 (t, 2H, J=7.5 Hz), 4.18 (t, 2H, J=6.5 Hz), 4.13 (t, 2H, J=6.5 Hz), 3.95 (t, 2H, J=6.5 Hz), 3.94 (t, 2H, J=6.5 Hz), 2.54-2.74 (m, 6H), 2.25-2.40 (m, 8H), 1.62-1.84 (m, 18H), 1.28-1.56 (m, 14H), 0.90 (t, 3H, J=7.0 Hz)

Intermediate P

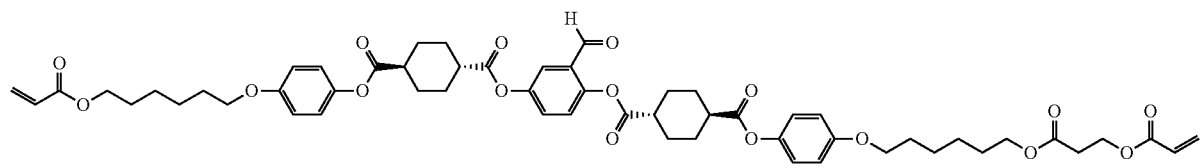

(Example 2) Synthesis of Mixture X (Mixture X)

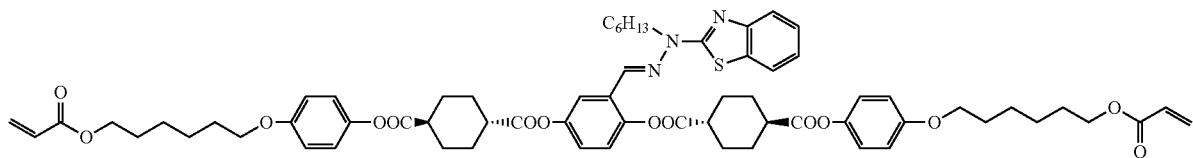

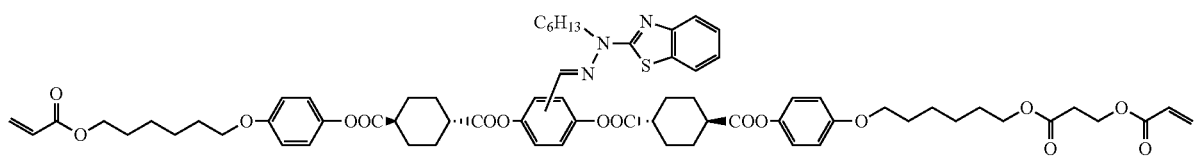

Step 1: Synthesis of Intermediate mixture Q (Mixture Q)

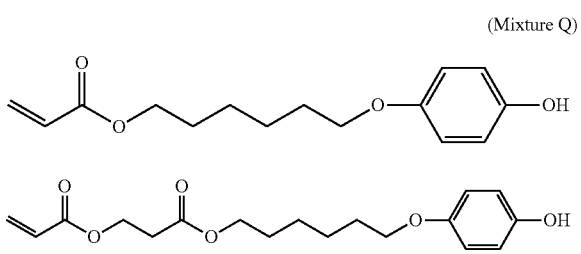

A three-necked reactor equipped with a thermometer and a condenser with a Dean-Stark trap was charged with 10.00 g of the brown crystals containing intermediate K synthesized in Step 1 in Example 1, 100 g of toluene and 0.105 g (0.476 mmol) of 2,6-di-t-butyl-p-cresol under a nitrogen stream, and the entire mass was stirred. The solution was heated to 80° C., 5.14 g (71.3 mmol) of acrylic acid and 0.91 g (9.51 mmol) of methanesulfonic acid were added, and dehydration reaction was performed at reflux (110° C.) for 3 hours with generated water removed out of the system. The reaction solution was then cooled to 30° C., and 500 g of distilled water was added. After stirring, the entire mass was allowed to stand. The organic phase was separated and 500 g of 5% brine was added for phase separation. The organic phase was separated and dried over sodium sulfate anhydrous, and sodium sulfate was filtered off. After condensation using a rotary evaporator, purification was performed by silica gel column chromatography (toluene:ethyl acetate=8:1) to give 8.2 g of mixture Q as a white solid. High-performance liquid chromatography of the white solid revealed that the mole ratio of the abundance of compounds in the white solid was as shown below. The mixture was directly used in Step 2 without purification.

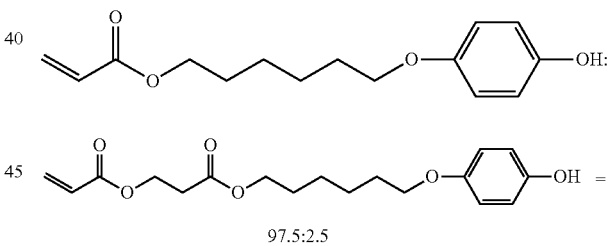

97.5:2.5

Step 2: Synthesis of Intermediate mixture R (Mixture R)

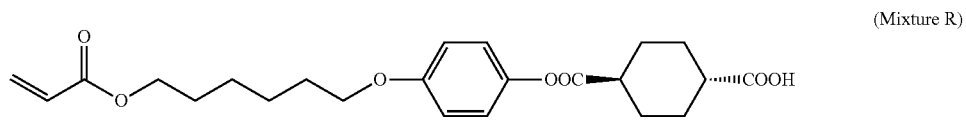

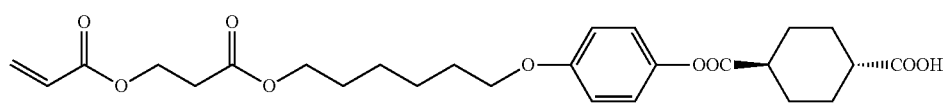

A three-necked reactor equipped with a thermometer was charged with 10.68 g (62.0 mmol) of trans-1,4-cyclohexanedicarboxylic acid and 90 ml of THF under a nitrogen stream. 3.9 g (34.1 mmol) of methanesulfonyl chloride was added and the reactor was immersed in a water bath to adjust the reaction solution temperature to 20° C. 3.79 g (37.5 mmol) of triethylamine was added dropwise over 10 minutes while retaining the reaction solution temperature to 20° C. to 30° C. After the dropwise addition, the entire mass was further stirred at 25° C. for 2 hours.

To the resulting reaction solution were added 0.38 g (3.12 mmol) of 4-(dimethylamino)pyridine and 8.2 g of mixture Q synthesized in Step 1, and the reactor was again immersed in the water bath to adjust the reaction solution temperature to 15° C. 3.79 g (37.5 mmol) of triethylamine was added dropwise over 10 minutes while retaining the reaction solution temperature to 20° C. to 30° C. After the dropwise addition, the entire mass was further stirred at 25° C. for 2 hours. After completion of the reaction, 1,000 ml of distilled water and 100 ml of saturated brine were added to the reaction solution and extracted twice with 400 ml of ethyl acetate. The organic phases were combined and dried over sodium sulfate anhydrous, and sodium sulfate was filtered off. The solvent was evaporated from the filtrate using a rotary evaporator, and the residue was purified by silica gel column chromatography (THF:toluene=1:9) to give 7.1 g of mixture R as a white solid. High-performance liquid chromatography of the white solid revealed that mole ratio of the abundance of compounds in the white solid was as shown below. The mixture was directly used in Step 3 without purification.

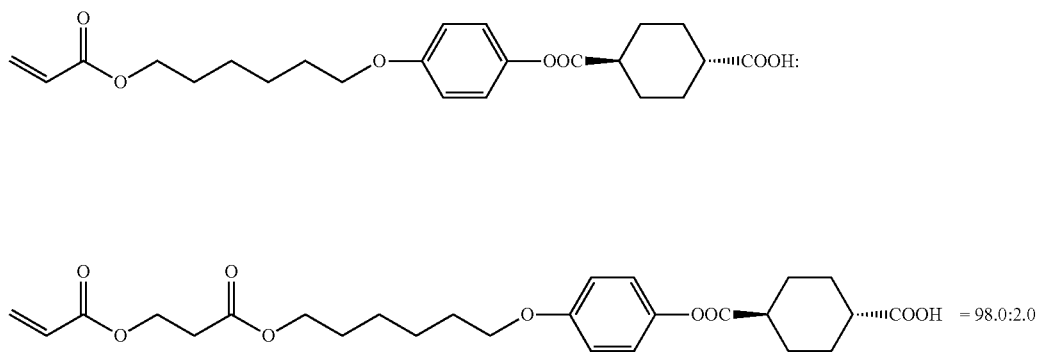

Step 3: Synthesis of Mixture S

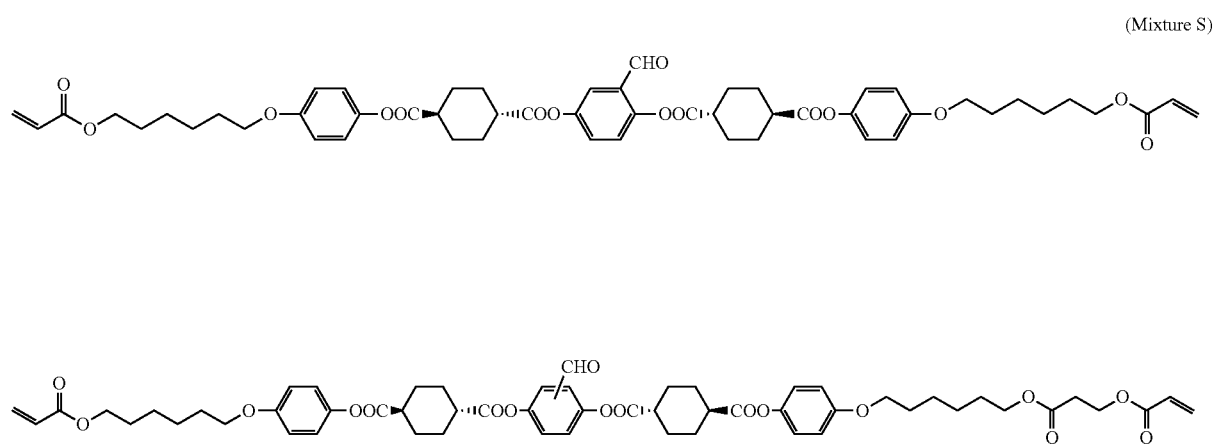

(Mixture S)

A three-necked reactor equipped with a thermometer was charged with 7.1 g of mixture R synthesized in Step 2 and 100 ml of THF under a nitrogen stream to prepare a homogenous solution. 2.39 g (20.9 mmol) of methanesulfonyl chloride was added and the reactor was immersed in a water bath to adjust the reaction solution temperature to 20° C. 2.16 g (21.3 mmol) of triethylamine was added dropwise over 5 minutes while retaining the reaction solution temperature to 20° C. to 30° C. After the dropwise addition, the entire mass was further stirred at 25° C. for 2 hours. To the resulting reaction solution were added 0.19 g (1.54 mmol) of 4-(dimethylamino)pyridine and 1.07 g (7.72 mmol) of 2,5-dihydroxybenzaldehyde, and the reactor was again immersed in the water bath to adjust the reaction solution temperature to 15° C. 1.95 g (19.3 mmol) of triethylamine was added dropwise over 5 minutes while retaining the reaction solution temperature to 20° C. to 30° C. After the dropwise addition, the entire mass was further stirred at 25° C. for 2 hours. After completion of the reaction, 400 ml of distilled water and 50 ml of saturated brine were added to the reaction solution and extracted twice with 750 ml of ethyl acetate. The organic phases were combined and dried over sodium sulfate anhydrous, and sodium sulfate was filtered off. The solvent was evaporated from the filtrate using a rotary evaporator, and the residue was dissolved in 150 ml of THF. 750 ml of methanol was added to the solution to precipitate crystals and the crystals were filtered off. The crystals obtained were washed with methanol and dried in vacuo to give 4.5 g of mixture S as a white solid. High-performance liquid chromatography of the white solid revealed that the mole ratio of the abundance of compounds in the white solid was as shown below. The mixture was directly used in Step 4 without purification.

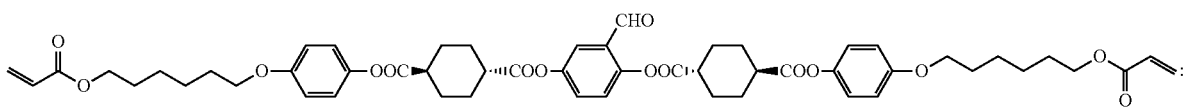

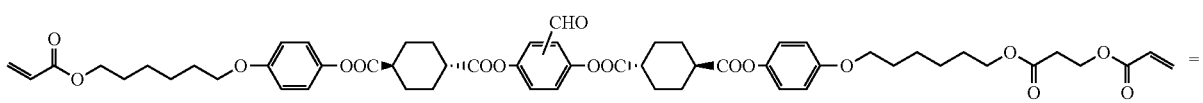

98.7:1.3

Step 4: Synthesis of Mixture X

A three-necked reactor equipped with a thermometer was charged with 4.5 g of mixture S synthesized in Step 3 and 50 ml of THF under a nitrogen stream to prepare a homogenous solution to which 0.93 ml (0.48 mmol) of concentrated hydrochloric acid was added. To the solution was dropwise added 1.25 g (5.0 mmol) of intermediate C synthesized in Step 1 of Synthesis Example 2 in 10 ml THF over 15 minutes. After the dropwise addition, the entire mass was further stirred at 25° C. for 1 hour. After completion of the reaction, the reaction solution was charged into 800 ml of methanol, and the precipitated solid was filtered off. The solid was dried using a vacuum drier to give 4.2 g of mixture X as a pale yellow solid. High-performance liquid chromatography of the pale yellow solid revealed that the mole ratio of the abundance of compounds in the pale yellow solid was as shown below.

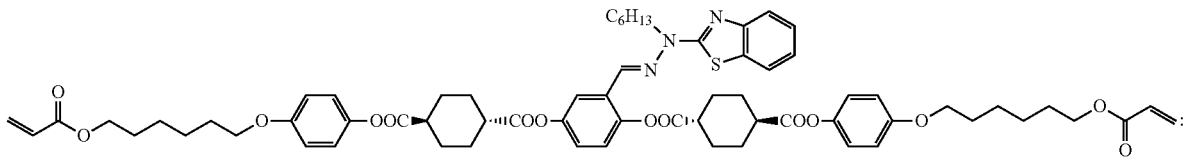

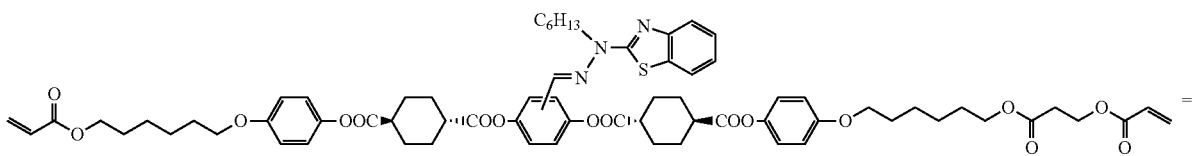

98.8:1.2

<Measurement of Phase Transition Temperature>

10 mg of each of compounds 1 to 9 and compound X was weighed and placed in solid state between two glass substrates with rubbed polyimide alignment films (product name: alignment treated glass substrate (E.H.C Co., Ltd.)). The obtained assembly was placed on a hot plate and the temperature was raised from 40° C. to 200° C., and then lowered to 40° C. Structural changes of the compound during temperature rise and fall were observed with a polarized optical microscope (ECLIPSELV100POL, NIKON) and the phase transition temperature was measured.

Measured phase transition temperatures are shown in Table 1 below.

In Table 1, "C" denotes Crystal, "N" Nematic, and "I" Isotropic. "Crystal" means that the test compound is in solid phase, "Nematic" means that the test compound is in nematic liquid crystal phase, and "Isotropic" means that the test compound is in isotropic liquid phase.

TABLE 1

| Compound No. | Phase transition temperature |
|---|---|
| Compound 1 | C ⇌ (163° C. / 40° C. or below) N ⇌ (200° C. or above) I |
| Compound 2 | C ⇌ (96° C. / 40° C. or below) N ⇌ (200° C. or above) I |
| Compound 3 | C ⇌ (116° C. / 40° C. or below) N ⇌ (200° C. or above) I |
| Compound 4 | C ⇌ (111° C. / 40° C. or below) N ⇌ (200° C. or above) I |
| Compound 5 | C ⇌ (110° C. / 40° C. or below) N ⇌ (216° C. / 210° C.) I |
| Compound 6 | C ⇌ (120° C. / 62° C.) N ⇌ (200° C. or above) I |
| Compound 7 | C ⇌ (88° C. / 40° C. or below) N ⇌ (200° C. / 193° C.) I |
| Compound 8 | C ⇌ (134° C. / 40° C. or below) N ⇌ (204° C. / 194° C.) I |
| Compound 9 | C ⇌ (110° C. / 40° C. or below) N ⇌ (200° C. or above) I |
| Compound X | C ⇌ (83° C. / 40° C. or below) N ⇌ (200° C. or above) I |

Examples 3 to 11

0.99 g of each of compounds 1 to 9 obtained in Synthesis Examples 1 to 9, 10 mg of compound X obtained in Example 1, 30 mg of photopolymerization initiator (Irgacure OXE02 (BASF)) and 100 mg of 1% cyclopentanone solution of surfactant (Ftergent 208G (NEOS)) were dissolved in a mixture solvent of 0.3 g 1,3-dioxolane and 2.0 g cyclopentanone. The solutions were filtrated through 0.45 μm pore disposable filters to provide polymerizable compositions (polymerizable liquid crystal compositions) 1 to 9.

Examples 12 to 20

0.90 g of each of compounds 1 to 9 obtained in Synthesis Examples 1 to 9, 100 mg of compound X obtained in Example 1, 30 mg of photopolymerization initiator (Irgacure OXE02 (BASF)) and 100 mg of 1% cyclopentanone solution of surfactant (Ftergent 208G (NEOS)) were dissolved in a mixture solvent of 0.3 g 1,3-dioxolane and 2.0 g cyclopentanone. The solutions were filtrated through 0.45 μm pore disposable filters to provide polymerizable compositions (polymerizable liquid crystal compositions) 10 to 18.

Example 21

1.0 g of mixture X obtained in Example 2, 30 mg of photopolymerization initiator (Irgacure OXE02 (BASF)) and 100 mg of 1% cyclopentanone solution of surfactant (Ftergent 208G (NEOS)) were dissolved in a mixture solvent of 0.3 g 1,3-dioxolane and 2.0 g cyclopentanone. The solution was filtrated through a 0.45 μm pore disposable filter to provide polymerizable composition (polymerizable liquid crystal composition) 19.

Comparative Examples 1 to 9

1.0 g of each of compounds 1 to 9 obtained in Synthesis Examples 1 to 9, 30 mg of photopolymerization initiator (Irgacure OXE02 (BASF)) and 100 mg of 1% cyclopentanone solution of surfactant (Ftergent 208G (NEOS)) were dissolved in a mixture solvent of 0.3 g 1,3-dioxolane and 2.0 g cyclopentanone. The solutions were filtrated through 0.45 μm pore disposable filters to provide polymerizable liquid crystal compositions 1r to 9r.

<Stability Evaluation of Liquid Crystal Phase>
(i) Formation of Liquid Crystal Layer Using Polymerizable Liquid Crystal Composition Using a #4 wire bar coater, each of polymerizable liquid crystal compositions 1 to 19 and 1r to 9r was applied to a transparent glass substrate with a rubbed polyimide alignment film (product name: alignment treated glass substrate (E.H.C Co., Ltd.)). The coating films were dried for 1 minute at temperatures shown in Table 2 and subjected to alignment treatment for 1 minute at temperatures shown in Table 2 to form liquid crystal layers (thickness: approx. 2.5 μm).

(ii) Formation of Optically Anisotropic Product

The liquid crystal layers manufactured in section (i) above were allowed to stand for 1 minute or 15 minutes at temperatures shown in Table 2. Subsequently, the liquid crystal layers were directly irradiated with UV light at a dose of 1,500 mJ/cm$^2$ to effect polymerization to provide optically anisotropic products with transparent glass substrates.

(iii) Determination of Stability of Liquid Crystal Phase

Figure 1B:
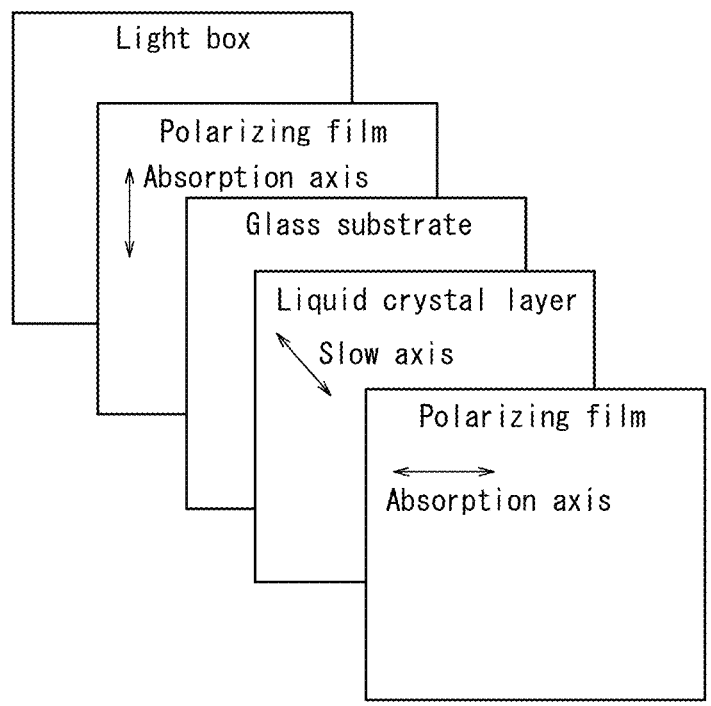

The optically anisotropic products with transparent glass substrates obtained in section (ii) above were each arranged as illustrated in FIGS. 1A and 1B to provide laminates and the state of the surface was visually observed. The surface free from unevenness is good. The degree of unevenness was evaluated on the scale of 1 to 5 with no unevenness being 5 and the presence of unevenness being 1. The evaluation results are summarized in Table 2.

Figure 2A:
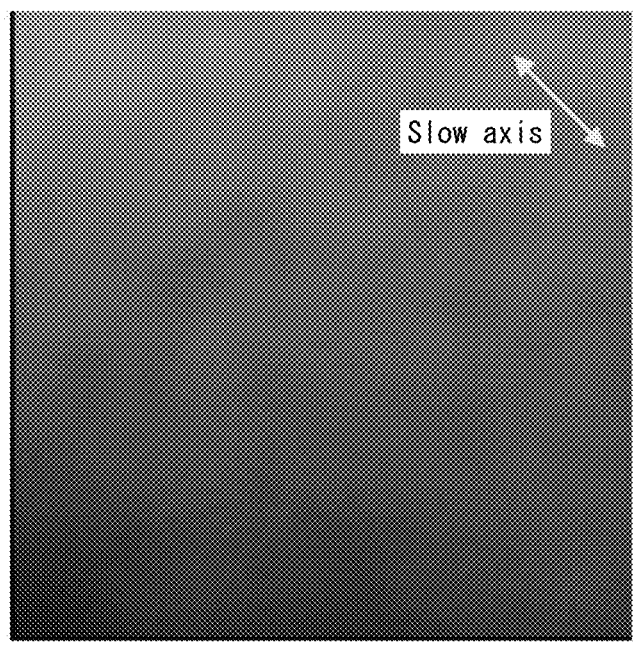
FIGS. 2A and 2B are pictures of laminates used for a stability evaluation test of a liquid crystal phase, taken from the side opposite to a light box, where
Figure 2B:
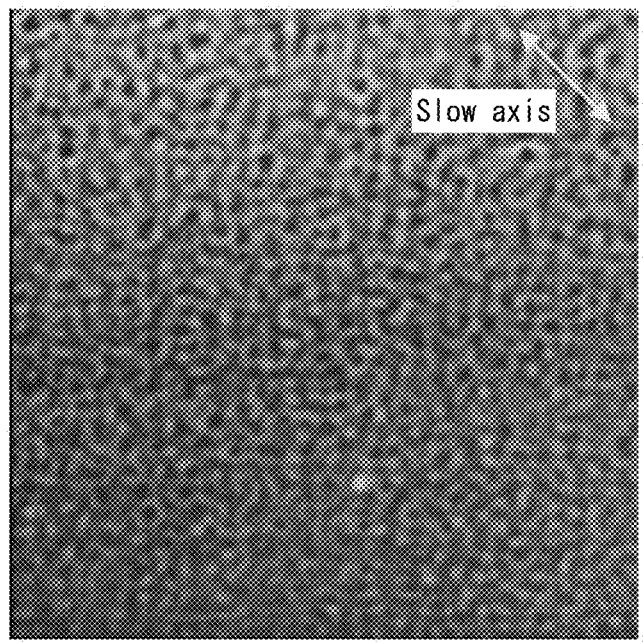

The polarizing films illustrated in FIGS. 1A and 1B are PVA polarizing films (Sumitomo Chemical Co., Ltd.). A picture of surface without unevenness (evaluation index: 5) and a picture of surface with unevenness (evaluation index: 1) are given in FIGS. 2A and 2B, respectively.

<Measurement of Optical Characteristics>

The optically anisotropic products with transparent glass substrates obtained in section (ii) above were measured for phase differences at wavelengths from 245.9 nm to 998.4 nm using an ellipsometer (M2000U, J.A. Woollam). Wavelength dispersion was also evaluated based on α and β values calculated as described below using the measured phase differences. The results are shown in Table 3.

$\alpha$=(phase difference at 449.9 nm)/(phase difference at 548.5 nm)

$\beta$=(phase difference at 650.2 nm)/(phase difference at 548.5 nm)

When the optically anisotropic product shows ideal wavelength dispersion showing a broad band property, i.e., reverse wavelength dispersion, α value becomes less than 1 and β value becomes greater than 1. When the optically anisotropic product shows flat wavelength dispersion α value and β values are similar. When the optically anisotropic product shows general (typical) wavelength dispersion, α value becomes greater than 1 and β value becomes less than 1. Namely, flat wavelength dispersion where α value and β value are similar is preferred, and reverse wavelength dispersion where α value becomes less than 1 and β value becomes greater than 1 is particularly preferred.

The thickness of the optically anisotropic product was measured as follows: the surface of the optically anisotropic product with a transparent glass substrate was scratched using a needle and the step height was measured by DEK-TAK 150 surface profilometer (ULVAC, Inc.).

TABLE 2

| | Polymerizable composition | Polymerizable compound (III) | | Polymerizable compound (IV) | | Drying temp. (° C.) | Alignment treatment temp. (° C.) | Retention temp. (° C.) | Light exposure temp. (° C.) | Evaluation of unevenness after 1 min retention | Evaluation of unevenness after 15 min retention |
|---|---|---|---|---|---|---|---|---|---|---|---|
| | | Compound used | Ratio (%) | Compound used | Ratio (%) | | | | | | |
| Example 3 | 1 | Compound X | 1 | Compound 1 | 99 | 180 | 23 | 23 | 23 | 4 | 4 |
| Example 4 | 2 | Compound X | 1 | Compound 2 | 99 | 120 | 23 | 23 | 23 | 5 | 5 |
| Example 5 | 3 | Compound X | 1 | Compound 3 | 99 | 120 | 23 | 23 | 23 | 5 | 5 |
| Example 6 | 4 | Compound X | 1 | Compound 4 | 99 | 120 | 23 | 23 | 23 | 5 | 5 |
| Example 7 | 5 | Compound X | 1 | Compound 5 | 99 | 120 | 23 | 23 | 23 | 5 | 5 |
| Example 8 | 6 | Compound X | 1 | Compound 6 | 99 | 130 | 70 | 65 | 65 | 4 | 4 |
| Example 9 | 7 | Compound X | 1 | Compound 7 | 99 | 130 | 23 | 23 | 23 | 5 | 5 |
| Example 10 | 8 | Compound X | 1 | Compound 8 | 99 | 130 | 23 | 23 | 23 | 4 | 4 |
| Example 11 | 9 | Compound X | 1 | Compound 9 | 99 | 130 | 23 | 23 | 23 | 5 | 5 |
| Example 12 | 10 | Compound X | 10 | Compound 1 | 90 | 170 | 23 | 23 | 23 | 5 | 4 |
| Example 13 | 11 | Compound X | 10 | Compound 2 | 90 | 100 | 23 | 23 | 23 | 5 | 5 |
| Example 14 | 12 | Compound X | 10 | Compound 3 | 90 | 100 | 23 | 23 | 23 | 5 | 5 |
| Example 15 | 13 | Compound X | 10 | Compound 4 | 90 | 100 | 23 | 23 | 23 | 5 | 5 |
| Example 16 | 14 | Compound X | 10 | Compound 5 | 90 | 100 | 23 | 23 | 23 | 5 | 5 |
| Example 17 | 15 | Compound X | 10 | Compound 6 | 90 | 110 | 70 | 65 | 65 | 5 | 4 |
| Example 18 | 16 | Compound X | 10 | Compound 7 | 90 | 120 | 23 | 23 | 23 | 5 | 5 |
| Example 19 | 17 | Compound X | 10 | Compound 8 | 90 | 120 | 23 | 23 | 23 | 5 | 4 |
| Example 20 | 18 | Compound X | 10 | Compound 9 | 90 | 120 | 23 | 23 | 23 | 5 | 5 |
| Example 21 | 19 | Compound X | 98.8 | Compound 2 | 1.2 | 120 | 23 | 23 | 23 | 5 | 5 |
| Comparative Example 1 | 1r | — | — | Compound 1 | 100 | 180 | 23 | 23 | 23 | 4 | 2 |
| Comparative Example 2 | 2r | — | — | Compound 2 | 100 | 120 | 23 | 23 | 23 | 5 | 4 |
| Comparative Example 3 | 3r | — | — | Compound 3 | 100 | 120 | 23 | 23 | 23 | 5 | 4 |
| Comparative Example 4 | 4r | — | — | Compound 4 | 100 | 120 | 23 | 23 | 23 | 5 | 4 |
| Comparative Example 5 | 5r | — | — | Compound 5 | 100 | 120 | 23 | 23 | 23 | 5 | 4 |
| Comparative Example 6 | 6r | — | — | Compound 6 | 100 | 130 | 70 | 65 | 65 | 4 | 2 |
| Comparative Example 7 | 7r | — | — | Compound 7 | 100 | 130 | 23 | 23 | 23 | 5 | 4 |
| Comparative Example 8 | 8r | — | — | Compound 8 | 100 | 130 | 23 | 23 | 23 | 4 | 2 |
| Comparative Example 9 | 9r | — | — | Compound 9 | 100 | 130 | 23 | 23 | 23 | 5 | 4 |

From Table 2, it can be seen that the polymerizable liquid crystal compositions containing compound X can provide coating films which can retain liquid crystal phase more stably over long periods of time and have less coating unevenness. It can also been from Table 2 that when compound X is added at an amount of 10% (Examples 12 to 20), it is possible to lower drying temperature and thus to provide liquid crystal compositions which are more easy to handle.

time, have low melting points suitable for practical use, and allow for low-cost manufacture of optical film etc. which are capable of uniform polarized light conversion over a wide wavelength range with a wide process margin.

The present disclosure also provides polymerizable compounds useful for the preparation of the polymerizable liquid crystal compositions and mixtures containing the polymer-

TABLE 3

| | Polymerizable composition | Polymerizable compound (III) | | Polymerizable compound (IV) | | Film thickness (μm) | Re (548.5 nm) | α | β |
|---|---|---|---|---|---|---|---|---|---|
| | | Compound used | Ratio (%) | Compound used | Ratio (%) | | | | |
| Example 3 | 1 | Compound X | 1 | Compound 1 | 99 | 1.568 | 93.49 | 0.791 | 1.043 |
| Example 4 | 2 | Compound X | 1 | Compound 2 | 99 | 1.612 | 118.82 | 0.842 | 1.045 |
| Example 5 | 3 | Compound X | 1 | Compound 3 | 99 | 1.489 | 116.19 | 0.880 | 1.031 |
| Example 6 | 4 | Compound X | 1 | Compound 4 | 99 | 1.599 | 123.24 | 0.835 | 1.027 |
| Example 7 | 5 | Compound X | 1 | Compound 5 | 99 | 1.673 | 124.28 | 0.847 | 1.035 |
| Example 8 | 6 | Compound X | 1 | Compound 6 | 99 | 1.524 | 122.65 | 0.854 | 1.032 |
| Example 9 | 7 | Compound X | 1 | Compound 7 | 99 | 1.495 | 113.73 | 0.836 | 1.020 |
| Example 10 | 8 | Compound X | 1 | Compound 8 | 99 | 1.503 | 129.09 | 0.888 | 1.004 |
| Example 11 | 9 | Compound X | 1 | Compound 9 | 99 | 1.624 | 124.59 | 0.845 | 1.057 |
| Example 12 | 10 | Compound X | 10 | Compound 1 | 90 | 1.567 | 93.39 | 0.795 | 1.041 |
| Example 13 | 11 | Compound X | 10 | Compound 2 | 90 | 1.606 | 118.36 | 0.837 | 1.035 |
| Example 14 | 12 | Compound X | 10 | Compound 3 | 90 | 1.519 | 118.53 | 0.884 | 1.032 |
| Example 15 | 13 | Compound X | 10 | Compound 4 | 90 | 1.612 | 124.28 | 0.832 | 1.029 |
| Example 16 | 14 | Compound X | 10 | Compound 5 | 90 | 1.657 | 123.11 | 0.844 | 1.033 |
| Example 17 | 15 | Compound X | 10 | Compound 6 | 90 | 1.487 | 119.71 | 0.850 | 1.030 |
| Example 18 | 16 | Compound X | 10 | Compound 7 | 90 | 1.471 | 111.92 | 0.831 | 1.022 |
| Example 19 | 17 | Compound X | 10 | Compound 8 | 90 | 1.526 | 131.04 | 0.887 | 1.022 |
| Example 20 | 18 | Compound X | 10 | Compound 9 | 90 | 1.623 | 124.53 | 0.845 | 1.057 |
| Example 21 | 19 | Compound X | 98.8 | Compound 2 | 1.2 | 1.601 | 117.99 | 0.841 | 1.044 |
| Comparative Example 1 | 1r | — | — | Compound 1 | 100 | 1.557 | 92.83 | 0.792 | 1.044 |
| Comparative Example 2 | 2r | — | — | Compound 2 | 100 | 1.613 | 118.86 | 0.837 | 1.039 |
| Comparative Example 3 | 3r | — | — | Compound 3 | 100 | 1.492 | 116.42 | 0.890 | 1.042 |
| Comparative Example 4 | 4r | — | — | Compound 4 | 100 | 1.588 | 122.44 | 0.832 | 1.023 |
| Comparative Example 5 | 5r | — | — | Compound 5 | 100 | 1.678 | 124.62 | 0.845 | 1.032 |
| Comparative Example 6 | 6r | — | — | Compound 6 | 100 | 1.528 | 122.96 | 0.852 | 1.029 |
| Comparative Example 7 | 7r | — | — | Compound 7 | 100 | 1.474 | 112.17 | 0.831 | 1.014 |
| Comparative Example 8 | 8r | — | — | Compound 8 | 100 | 1.494 | 128.32 | 0.893 | 1.009 |
| Comparative Example 9 | 9r | — | — | Compuond 9 | 100 | 1.632 | 125.24 | 0.847 | 1.057 |

It can be seen from Table 3 that also in Examples 1 to 21, α value becomes less than 1 and β value becomes greater than 1. Thus, it can be seen that even when compound X is added, ideal wavelength dispersion showing a broad band property, i.e., reverse wavelength dispersion was ensured.

INDUSTRIAL APPLICABILITY

The present disclosure provides compositions which can retain liquid crystal phase more stably over long periods of izable compounds, and compounds useful for the preparation of the polymerizable compounds and mixtures containing the compounds.

The present disclosure further provides optical films and optically anisotropic products capable of uniform polarized light conversion over a wide wavelength range, and polarizing plates, flat panel display devices, organic electroluminescence (EL) display devices and anti-reflection films that include the optical film or optically anisotropic product.

The invention claimed is:
1. A mixture comprising:
a polymerizable compound having the following Formula (III):

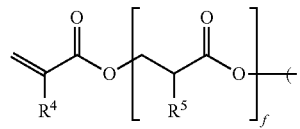

(III)

where $Ar^1$ represents divalent aromatic hydrocarbon ring group having $D^1$ as a substituent, or divalent heteroaromatic ring group having $D^1$ as a substituent, $D^1$ represents C1-C20 organic group having at least one aromatic ring selected from the group consisting of an aromatic hydrocarbon ring and a heteroaromatic ring, $Z^{11}$ and $Z^{12}$ represent each independently —CO—O—, —O—CO—, —NR$^{31}$—CO— or —CO—NR$^{32}$—, where $R^{31}$ and $R^{32}$ represent each independently hydrogen or C1-C6 alkyl group, $A^{11}$, $A^{12}$, $B^{11}$ and $B^{12}$ represent each independently alicyclic group which may have a substituent, or aromatic group which may have a substituent, $Y^{11}$ and $Y^{12}$ represent each independently —O—, —CO—, —CO—O—, —O—CO—, —NR$^{21}$—CO—, —CO—NR$^{22}$—, —O—CO—O—, —NR$^{23}$—CO—O—, —O—CO—NR$^{24}$— or —NR$^{25}$—CO—NR$^{26}$—, where $R^{21}$ to $R^{26}$ represent each independently hydrogen or C1-C6 alkyl group, $L^{11}$ and $L^{12}$ represent each independently single bond, —O—, —CO—, —CO—O—, —O—CO—, —NR$^{21}$—CO—, —CO—NR$^{22}$—, —O—CO—O—, —O—CO—NR$^{24}$— or —NR$^{25}$—CO—NR$^{26}$—, where $R^{21}$ to $R^{26}$ represent each independently hydrogen or C1-C6 alkyl group, $R^4$ to $R^7$ represent each independently hydrogen, methyl group or chlorine, one of f and k is an integer of 1 to 3 with the other being an integer of 0 to 3, g and j represent each independently an integer of 1 to 20, and h and i are each independently 0 or 1; and a polymerizable compound having the following Formula (IV):

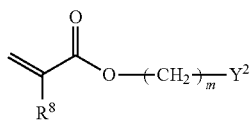

(IV)

where $Ar^2$ represents divalent aromatic hydrocarbon ring group having $D^2$ as a substituent, or divalent heteroaromatic ring group having $D^2$ as a substituent, $D^2$ represents C1-C20 organic group having at least one aromatic ring selected from the group consisting of an aromatic hydrocarbon ring and a heteroaromatic ring, $Z^{21}$ and $Z^{22}$ represent each independently —CO—O—, —O—CO—, —NR$^{31}$—CO— or —CO—NR$^{32}$—, where $R^{31}$ and $R^{32}$ represent each independently hydrogen or C1-C6 alkyl group, $A^{21}$, $A^{22}$, $B^{21}$ and $B^{22}$ represent each independently alicyclic group which may have a substituent, or aromatic group which may have a substituent, $Y^{21}$, $Y^{22}$, $L^{21}$ and $L^{22}$ represent each independently single bond, —O—, —CO—, —CO—O—, —O—CO—, —NR$^{12}$—CO—, —CO—NR$^{22}$—, —O—CO—O—, —NR$^{23}$—CO—O—, —O—CO—NR$^{24}$— or —NR$^{25}$—CO—NR$^{26}$—, where $R^{21}$ to $R^{26}$ represent each independently hydrogen or C1-C6 alkyl group, $R^8$ and $R^9$ represent each independently hydrogen, methyl group or chlorine, m and q represent each independently an integer of 1 to 20, and n and p are each independently 0 or 1, wherein $Ar^1$, $Z^{11}$, $Z^{12}$, $A^{11}$, $A^{12}$, $B^{11}$, $B^{12}$, $Y^{11}$, $Y^{12}$, $L^{11}$, $L^{12}$, $R^4$, $R^7$, g, h and i of the polymerizable compound (III) are the same as $Ar^2$, $Z^{21}$, $Z^{22}$, $A^{21}$, $A^{22}$, $B^{21}$, $B^{22}$, $Y^{21}$, $Y^{22}$, $L^{21}$, $L^{22}$, $R^8$, $R^9$, m, q, n and p of the polymerizable compound (IV), respectively.

2. The mixture of claim 1, wherein $Ar^1$-$D^1$ is a divalent group having the following Formula (V):

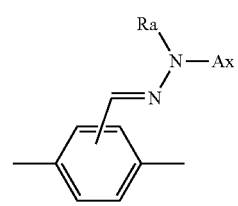

(V)

where Ax represents C2-C20 organic group having at least one aromatic ring selected from the group consisting of an aromatic hydrocarbon ring and a heteroaromatic ring, and Ra represents hydrogen or C1-C20 organic group which may have a substituent, and wherein Ar²-D² is a divalent group having the following Formula (VII):

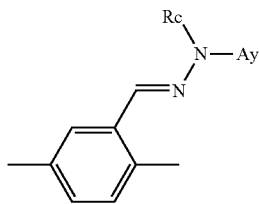
(VII)

where Ay represents C2-C20 organic group having at least one aromatic ring selected from the group consisting of an aromatic hydrocarbon ring and a heteroaromatic ring, and
Rc represents hydrogen or C1-C20 organic group which may have a substituent.

3. The mixture of claim 2, wherein Ax and Ay are each independently a group having the following Formula (VI):

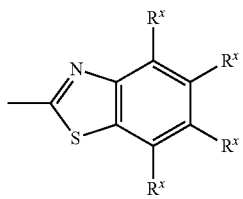
(VI)

where $R^x$ represents hydrogen, halogen, C1-C6 alkyl group, cyano group, nitro group, C1-C6 fluoroalkyl group, C1-C6 alkoxy group, or —C(=O)—O—$R^b$, where $R^b$ represents C1-C20 alkyl group which may have a substituent, C2-C20 alkenyl group which may have a substituent, C3-C12 cycloalkyl group which may have a substituent, or C5-C12 aromatic hydrocarbon ring group which may have a substituent, each $R^x$ may be the same or different, and at least one C—$R^x$ constituting the ring may be replaced by nitrogen.

4. The mixture of claim 2, wherein Ra is C1-C20 alkyl group which may have a substituent, C2-C20 alkenyl group which may have a substituent, C2-20 alkynyl group which may have a substituent, or C6-C18 aromatic group which may have a substituent, and Rc is C1-C20 alkyl group which may have a substituent, C2-C20 alkenyl group which may have a substituent, C2-20 alkynyl group which may have a substituent, or C6-C18 aromatic group which may have a substituent.

5. The mixture of claim 1, wherein a mass ratio of the polymerizable compound having Formula (III) to the polymerizable compound having Formula (IV) is 1:1,000 to 20:100.

* * * * *